US012624094B2

(12) United States Patent
Kuijpers et al.

(10) Patent No.: US 12,624,094 B2
(45) Date of Patent: May 12, 2026

(54) FACTOR H POTENTIATING ANTIBODIES AND USES THEREOF

(71) Applicant: Stichting Sanquin Bloedvoorziening, Amsterdam (NL)

(72) Inventors: Taco Willem Kuijpers, Amsterdam (NL); Diana Wouters, Badhoevedorp (NL); Maria Clara Brouwer, Blokker (NL); Richard Benjamin Pouw, Lörrach (DE)

(73) Assignee: STICHTING SANQUIN BLOEDVOORZIENING, Amsterdam (NL)

( * ) Notice: Subject to any disclaimer, the term of this patent is extended or adjusted under 35 U.S.C. 154(b) by 977 days.

(21) Appl. No.: 17/829,688

(22) Filed: Jun. 1, 2022

(65) Prior Publication Data

US 2022/0356235 A1 Nov. 10, 2022

Related U.S. Application Data

(63) Continuation of application No. 16/961,737, filed as application No. PCT/NL2019/050018 on Jan. 15, 2019, now Pat. No. 11,377,487.

(30) Foreign Application Priority Data

Jan. 15, 2018 (EP) .................................... 18151726

(51) Int. Cl.
*C07K 16/18* (2006.01)

(52) U.S. Cl.
CPC .......... *C07K 16/18* (2013.01); *C07K 2317/33* (2013.01); *C07K 2317/52* (2013.01); *C07K 2317/55* (2013.01); *C07K 2317/565* (2013.01); *C07K 2317/92* (2013.01)

(58) Field of Classification Search
None
See application file for complete search history.

(56) References Cited

U.S. PATENT DOCUMENTS 11,377,487 B2 * 7/2022 Kuijpers ................ C07K 16/18
11,820,814 B2 * 11/2023 Lauder ................... C07K 16/18

FOREIGN PATENT DOCUMENTS

| | | | | |
|---|---|---|---|---|
| JP | 2013508287 A | 3/2013 | | |
| JP | 2013510164 A | 3/2013 | | |
| JP | 2017525362 A | 9/2017 | | |
| JP | 2017532952 A | 11/2017 | | |
| WO | 2011047146 A2 | 4/2011 | | |
| WO | 2011056997 A1 | 5/2011 | | |
| WO | WO-2016028150 A1 * | 2/2016 | ................ | A61P 7/00 |
| WO | 2016033225 A1 | 3/2016 | | |

OTHER PUBLICATIONS

Bowers et al., J Biol Chem. Mar. 15, 2013;288(11):7688-7696. doi:10.1074/jbc.M112.445502. Epub Jan. 25, 2013. PMID: 23355464 PMCID: PMC3597809.*

Csincsi et al. "FHR-1 Binds to C-Reactive Protein and Enhances Rather than Inhibits Complement Activation", The Journal of Immunology, US, (Jul. 1, 2017), vol. 199, No. 1, doi:10.4049/jimmunol.1600483, ISSN 0022-1767, pp. 292-303.

Simon et al. "Malaria Parasites Co-opt Human Factor H to Prevent Complement-Mediated Lysis in the Mosquito Midgut", Cell Host & Microbe, NL, (Jan. 1, 2013), vol. 13, No. 1, doi:10.1016/j.chom.2012.11.013, ISSN 1931-3128, pp. 29-41.

Prodinger et al. "The C-terminus of factor H: monoclonal antibodies inhibit heparin binding and identify epitopes common to factor H and factor H-related proteins", The Biochemical journal, England, (Apr. 1, 1998), pp. 41-47, URL: https://www.ncbi.nlm.nih.gov/pmc/articles/PMC1219319/pdf/9512460.pdf, pp. 41-47.

Cheng et al. "Complement Factor H as a Marker for Detection of Bladder Cancer", Clinical Chemistry, (May 1, 2005), vol. 51, No. 5, doi:10.1373/clinchem.2004.042192, ISSN 0009-9147, pp. 856-863.

International Search Report and Written Opinion in corresponding International Patent Application No. PCT/NL2019/050018 mailed Jun. 13, 2019. 10 pages.

Mayo "glomerulonephritis" access from mayoclinic.org on Jul. 23, 2021 (Year:2021).

* cited by examiner

*Primary Examiner* — Michael Szperka
(74) *Attorney, Agent, or Firm* — Leason Ellis LLP

(57) ABSTRACT

The invention relates to novel isolated, synthetic or recombinant antibodies and fragments thereof specific for factor H. The invention further relates to the use of such antibodies and fragments for inhibiting complement activation and treatment of disorders associated with complement activation.

17 Claims, 10 Drawing Sheets

Specification includes a Sequence Listing.

A.

Competing fragment

FH
CCP 15-18
CCP 15-19
CCP 18-20
CCP 19-20

B.

C.

A.

B.

$k_a = 8.33*10^5 M^{-1}s^{-1}$
$k_d = 2.70*10^{-4} s^{-1}$
$K_D = 0.32*10^{-9} M$ $k_a = 2.39*10^6 M^{-1}s^{-1}$
$k_d = 1.27*10^{-5} s^{-1}$
$K_D = 5.44*10^{-12} M$ $k_a = 1.58*10^6 M^{-1}s^{-1}$
$k_d = 4.96*10^{-5} s^{-1}$
$K_D = 3.13*10^{-11} M$

C.

D.

A.

B.

A.

B.

SEQUENCE LISTING

<160> NUMBER OF SEQ ID NOS: 100

<210> SEQ ID NO 1
<211> LENGTH: 5
<212> TYPE: PRT
<213> ORGANISM: Artificial Sequence
<220> FEATURE:
<223> OTHER INFORMATION: FH.07 LC CDR1

```
<400> SEQUENCE: 1

Ser Ser Val Lys Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: FH.07 LC CDR2

<400> SEQUENCE: 2

Ala Thr Ser
1

<210> SEQ ID NO 3
<211> LENGTH: 9
<212> TYPE: PRT
<213> ORGANISM: Artificial Sequence
<220> FEATURE:
<223> OTHER INFORMATION: FH.07 LC CDR3

<400> SEQUENCE: 3

Gln Gln Trp Ser Ile Ile Pro Pro Thr
1               5

<210> SEQ ID NO 4
<211> LENGTH: 106
<212> TYPE: PRT
<213> ORGANISM: Artificial Sequence
<220> FEATURE:
<223> OTHER INFORMATION: FH.07 VL

<400> SEQUENCE: 4

Gln Ile Val Leu Ser Gln Ser Pro Thr Phe Leu Ser Ala Ser Pro Gly
1               5                   10                  15

Glu Lys Val Thr Val Thr Cys Arg Ala Ser Ser Ser Val Lys Tyr Met
            20                  25                  30

His Trp Tyr Gln Gln Lys Pro Gly Ala Ser Pro Lys Pro Trp Ile Phe
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ile Ile Pro Pro Thr
                85                  90                  95

Phe Gly Asn Gly Thr Lys Leu Glu Leu Lys
            100                 105

<210> SEQ ID NO 5
<211> LENGTH: 8
<212> TYPE: PRT
<213> ORGANISM: Artificial Sequence
<220> FEATURE:
<223> OTHER INFORMATION: FH.07 HC CDR1

<400> SEQUENCE: 5

Asp Phe Ser Leu Ala Arg Tyr Gly
1               5

<210> SEQ ID NO 6
<211> LENGTH: 7
```

```
<212> TYPE: PRT
<213> ORGANISM: Artificial Sequence
<220> FEATURE:
<223> OTHER INFORMATION: FH.07 HC CDR2

<400> SEQUENCE: 6

Ile Trp Ser Gly Gly Thr Ala
1               5

<210> SEQ ID NO 7
<211> LENGTH: 11
<212> TYPE: PRT
<213> ORGANISM: Artificial Sequence
<220> FEATURE:
<223> OTHER INFORMATION: FH.07 HC CDR3

<400> SEQUENCE: 7

Ala Arg Asn Phe Gly Asn Tyr Ala Val Asp Tyr
1               5                   10

<210> SEQ ID NO 8
<211> LENGTH: 112
<212> TYPE: PRT
<213> ORGANISM: Artificial Sequence
<220> FEATURE:
<223> OTHER INFORMATION: FH.07 VH

<400> SEQUENCE: 8

Gln Val Gln Leu Gln Gln Ser Gly Pro Gly Leu Val Gln Pro Ser Gln
1               5                   10                  15

Ser Leu Ser Ile Thr Cys Thr Val Ser Asp Phe Ser Leu Ala Arg Tyr
                20                  25                  30

Gly Val His Trp Ile Arg Gln Ser Pro Gly Lys Gly Leu Glu Trp Leu
            35                  40                  45

Gly Val Ile Trp Ser Gly Gly Thr Ala Asp Tyr Asn Ala Ala Phe Ile
        50                  55                  60

Ser Arg Leu Asn Ile Asn Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Phe Gly Asn Tyr Ala Val Asp Tyr Trp Gly Gln Gly Thr Ser
            100                 105                 110

<210> SEQ ID NO 9
<211> LENGTH: 15
<212> TYPE: DNA
<213> ORGANISM: Artificial Sequence
<220> FEATURE:
<223> OTHER INFORMATION: FH.07 LC CDR1

<400> SEQUENCE: 9
tcaagtgtca aatac                                                    15

<210> SEQ ID NO 10
<211> LENGTH: 9
<212> TYPE: DNA
<213> ORGANISM: Artificial Sequence
<220> FEATURE:
<223> OTHER INFORMATION: FH.07 LC CDR2

<400> SEQUENCE: 10 gccacatcc                                                           9
```

-continued

```
<210> SEQ ID NO 11
<211> LENGTH: 27
<212> TYPE: DNA
<213> ORGANISM: Artificial Sequence
<220> FEATURE:
<223> OTHER INFORMATION: FH.07 LC CDR3

<400> SEQUENCE: 11
cagcagtgga gtattatccc acccacg                                          27

<210> SEQ ID NO 12
<211> LENGTH: 319
<212> TYPE: DNA
<213> ORGANISM: Artificial Sequence
<220> FEATURE:
<223> OTHER INFORMATION: FH.07 VL

<400> SEQUENCE: 12
caaattgttc tctcccagtc tccaacattc ctgtctgcat ctccaggtga gaaggtcaca     60
gtgacttgca gggccagttc aagtgtcaaa tacatgcact ggtatcagca gaaaccagga    120
gcctccccca aaccctggat ttttgccaca tccaacctgg cttctggagt ccctgctcgc    180
ttcagtggca gtgggtctgg gacctcttat tctctcacaa tcagcagagt ggaggctgaa    240
gatgctgcca cttattactg ccagcagtgg agtattatcc acccacgtt  cggtaatggg     300 accaagctgg agctgaaac                                                 319

<210> SEQ ID NO 13
<211> LENGTH: 24
<212> TYPE: DNA
<213> ORGANISM: Artificial Sequence
<220> FEATURE:
<223> OTHER INFORMATION: FH.07 HC CDR1

<400> SEQUENCE: 13
gatttctcat tagctaggta tggt                                            24

<210> SEQ ID NO 14
<211> LENGTH: 21
<212> TYPE: DNA
<213> ORGANISM: Artificial Sequence
<220> FEATURE:
<223> OTHER INFORMATION: FH.07 HC CDR2

<400> SEQUENCE: 14
atatggagtg gtggaaccgc a                                               21

<210> SEQ ID NO 15
<211> LENGTH: 33
<212> TYPE: DNA
<213> ORGANISM: Artificial Sequence
<220> FEATURE:
<223> OTHER INFORMATION: FH.07 HC CDR3

<400> SEQUENCE: 15
gccagaaatt ttggtaacta cgctgtggac tac                                  33

<210> SEQ ID NO 16
<211> LENGTH: 337
<212> TYPE: DNA
<213> ORGANISM: Artificial Sequence
<220> FEATURE:
<223> OTHER INFORMATION: FH.07 VH

<400> SEQUENCE: 16
```

-continued

```
caggtgcagc tgcagcagtc aggacctggc ctagtgcagc cctctcagag cctgtccatt      60
acctgcacag tctctgattt ctcattagct aggtatggtg tacactggat tcgccagtct     120
ccaggaaagg gtctggagtg gctgggagtg atatggagtg gtggaaccgc agactataat     180
gcagctttca tatccagact gaacatcaac aaggacaatt ccaagagcca agttttcttt     240
aaaatgaaca gtctccaagc taatgacaca gccatatatt actgtgccag aaattttggt     300
aactacgctg tggactactg gggtcaagga acctcag                              337
```

```
<210> SEQ ID NO 17
<211> LENGTH: 5
<212> TYPE: PRT
<213> ORGANISM: Artificial Sequence
<220> FEATURE:
<223> OTHER INFORMATION: FHR-1.8E4 LC CDR1

<400> SEQUENCE: 17

Ser Ser Val Arg Tyr
1               5

<210> SEQ ID NO 18
<211> LENGTH: 3
<212> TYPE: PRT
<213> ORGANISM: Artificial Sequence
<220> FEATURE:
<223> OTHER INFORMATION: FHR-1.8E4 LC CDR2

<400> SEQUENCE: 18

Ala Thr Ser
1

<210> SEQ ID NO 19
<211> LENGTH: 9
<212> TYPE: PRT
<213> ORGANISM: Artificial Sequence
<220> FEATURE:
<223> OTHER INFORMATION: FHR-1.8E4 LC CDR3

<400> SEQUENCE: 19

Gln Gln Trp Gly Thr Lys Pro Pro Thr
1               5

<210> SEQ ID NO 20
<211> LENGTH: 106
<212> TYPE: PRT
<213> ORGANISM: Artificial Sequence
<220> FEATURE:
<223> OTHER INFORMATION: FHR-1.8E4 VL

<400> SEQUENCE: 20

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Arg Tyr Met
            20                  25                  30

His Trp Tyr Gln Gln Lys Ala Gly Ser Ser Pro Thr Ala Trp Ile Phe
        35                  40                  45

Ala Thr Ser Asn Leu Ala Ser Gly Val Pro Pro Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Gly Thr Lys Pro Pro Thr
                85                  90                  95
```

-continued

```
Phe Gly Ala Gly Thr Lys Leu Glu Leu Lys
            100                 105

<210> SEQ ID NO 21
<211> LENGTH: 8
<212> TYPE: PRT
<213> ORGANISM: Artificial Sequence
<220> FEATURE:
<223> OTHER INFORMATION: FHR-1.8E4 HC CDR1

<400> SEQUENCE: 21

Asp Phe Ser Leu Thr Asn Ser Gly
1               5

<210> SEQ ID NO 22
<211> LENGTH: 7
<212> TYPE: PRT
<213> ORGANISM: Artificial Sequence
<220> FEATURE:
<223> OTHER INFORMATION: FHR-1.8E4 HC CDR2

<400> SEQUENCE: 22

Ile Trp Ser Gly Gly Thr Thr
1               5

<210> SEQ ID NO 23
<211> LENGTH: 11
<212> TYPE: PRT
<213> ORGANISM: Artificial Sequence
<220> FEATURE:
<223> OTHER INFORMATION: FHR-1.8E4 HC CDR3

<400> SEQUENCE: 23

Ala Arg Asn Phe Gly Asn Tyr Ala Val Asp Tyr
1               5                   10

<210> SEQ ID NO 24
<211> LENGTH: 117
<212> TYPE: PRT
<213> ORGANISM: Artificial Sequence
<220> FEATURE:
<223> OTHER INFORMATION: FHR-1.8E4 VH

<400> SEQUENCE: 24

Gln Val Gln Leu Lys Gln Ser Gly Pro Gly Leu Val Gln Pro Ser Gln
1               5                   10                  15

Ser Leu Ser Ile Thr Cys Thr Val Ser Asp Phe Ser Leu Thr Asn Ser
                20                  25                  30

Gly Val His Trp Val Arg Gln Ser Pro Gly Lys Gly Leu Glu Trp Leu
            35                  40                  45

Gly Val Ile Trp Ser Gly Gly Thr Thr Glu Tyr Asn Ala Ala Phe Met
        50                  55                  60

Ser Arg Leu Thr Ile Thr Lys Asp Asn Ser Lys Ser Gln Val Phe Phe
65                  70                  75                  80

Lys Met Asn Ser Leu Leu Val Asp Asp Thr Gly Ile Tyr Tyr Cys Ala
                85                  90                  95

Arg Asn Phe Gly Asn Tyr Ala Val Asp Tyr Trp Gly Gln Gly Thr Ser
                100                 105                 110

Val Thr Val Ser Ser
            115

<210> SEQ ID NO 25
<211> LENGTH: 18
```

```
<212> TYPE: DNA
<213> ORGANISM: Artificial Sequence
<220> FEATURE:
<223> OTHER INFORMATION: fake sequence to correct numbering

<400> SEQUENCE: 25
aaaaaaaaaa aaaaaaaa                                                 18

<210> SEQ ID NO 26
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 26
aaaaaaaaaa aaaaaaaa                                                 18

<210> SEQ ID NO 27
<211> LENGTH: 23
<212> TYPE: DNA
<213> ORGANISM: Artificial Sequence
<220> FEATURE:
<223> OTHER INFORMATION: fake sequence to correct numbering

<400> SEQUENCE: 27
aaaaaaaaaa aaaaaaaaaa aaa                                           23

<210> SEQ ID NO 28
<211> LENGTH: 319
<212> TYPE: DNA
<213> ORGANISM: Artificial Sequence
<220> FEATURE:
<223> OTHER INFORMATION: FHR-1.8E4 VL

<400> SEQUENCE: 28
ccaattgttc tctcccagtc tccagcaatc ctgtctgcat ctccagggga gaaggtcaca   60
atgacttgca gggccagctc aagtgttagg tacatgcact ggtaccagca gaaggcagga  120 tcctcccca cagcctggat ttttgccaca tccaacctgg cttctggagt ccctcctcgc  180
ttcagtggca gtgggtctgg gacctcttac tctctcacaa tcagcagagt ggaggctgaa  240
gatgctgcca cttattactg ccagcagtgg ggtactaagc cacccacgtt cggtgctggg  300
accaagctgg agctgaaac                                               319

<210> SEQ ID NO 29
<211> LENGTH: 15
<212> TYPE: DNA
<213> ORGANISM: Artificial Sequence
<220> FEATURE:
<223> OTHER INFORMATION: fake sequence to correct numbering

<400> SEQUENCE: 29
aaaaaaaaaa aaaaa                                                    15

<210> SEQ ID NO 30
<211> LENGTH: 16
<212> TYPE: DNA
<213> ORGANISM: Artificial Sequence
<220> FEATURE:
<223> OTHER INFORMATION: fake sequence to correct numbering

<400> SEQUENCE: 30
aaaaaaaaaa aaaaaa                                                   16
```

```
<210> SEQ ID NO 31
<211> LENGTH: 16
<212> TYPE: DNA
<213> ORGANISM: Artificial Sequence
<220> FEATURE:
<223> OTHER INFORMATION: fake sequence to correct numbering

<400> SEQUENCE: 31
aaaaaaaaaa aaaaaa                                                     16

<210> SEQ ID NO 32
<211> LENGTH: 352
<212> TYPE: DNA
<213> ORGANISM: Artificial Sequence
<220> FEATURE:
<223> OTHER INFORMATION: FHR-1.8E4 VH

<400> SEQUENCE: 32
caggtgcagc tgaagcagtc aggacctggc ctagtgcagc cctcacagag cctgtccatc    60
acctgcacag tctctgattt ctcattaact aattctggtg tacactgggt tcgccagtct   120
ccaggaaagg gtctggagtg gctgggagtg atatggagtg gtggaaccac agagtataat   180
gcagctttca tgtccagact gaccatcacc aaggacaact ccaagagcca gttttcttt    240 aaaatgaaca gtctgctagt tgatgataca ggcatatatt actgtgccag aaattttggt   300
aattatgctg tggactactg gggtcaagga acctcagtca ccgtctcctc ag           352

<210> SEQ ID NO 33
<211> LENGTH: 5
<212> TYPE: PRT
<213> ORGANISM: Artificial Sequence
<220> FEATURE:
<223> OTHER INFORMATION: FHR-1.3B4 LC CDR1

<400> SEQUENCE: 33

Ser Ser Val Thr Tyr
1               5

<210> SEQ ID NO 34
<211> LENGTH: 3
<212> TYPE: PRT
<213> ORGANISM: Artificial Sequence
<220> FEATURE:
<223> OTHER INFORMATION: FHR-1.3B4 LC CDR2

<400> SEQUENCE: 34

Ala Thr Ser
1

<210> SEQ ID NO 35
<211> LENGTH: 10
<212> TYPE: PRT
<213> ORGANISM: Artificial Sequence
<220> FEATURE:
<223> OTHER INFORMATION: FHR-1.3B4 LC CDR3

<400> SEQUENCE: 35

Gln Gln Arg Ser Ser Ser Asn Pro Leu Thr
1               5                   10

<210> SEQ ID NO 36
<211> LENGTH: 107
<212> TYPE: PRT
<213> ORGANISM: Artificial Sequence
<220> FEATURE:
```

-continued

<223> OTHER INFORMATION: FHR-1.3B4 VL

<400> SEQUENCE: 36

```
Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Ser Val Thr Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Arg Ser Ser Ser Asn Pro Leu
                85                  90                  95

Thr Phe Gly Ala Gly Thr Lys Leu Glu Leu Lys
            100                 105
```

<210> SEQ ID NO 37
<211> LENGTH: 8
<212> TYPE: PRT
<213> ORGANISM: Artificial Sequence
<220> FEATURE:
<223> OTHER INFORMATION: FHR-1.3B4 HC CDR1

<400> SEQUENCE: 37

```
Gly Phe Ser Leu Thr Asn Tyr Gly
1               5
```

<210> SEQ ID NO 38
<211> LENGTH: 7
<212> TYPE: PRT
<213> ORGANISM: Artificial Sequence
<220> FEATURE:
<223> OTHER INFORMATION: FHR-1.3B4 HC CDR2

<400> SEQUENCE: 38

```
Ile Trp Ser Gly Gly Thr Thr
1               5
```

<210> SEQ ID NO 39
<211> LENGTH: 11
<212> TYPE: PRT
<213> ORGANISM: Artificial Sequence
<220> FEATURE:
<223> OTHER INFORMATION: FHR-1.3B4 HC CDR3

<400> SEQUENCE: 39

```
Ala Arg Asn Phe Gly Asn Tyr Ala Met Asp Tyr
1               5                   10
```

<210> SEQ ID NO 40
<211> LENGTH: 117
<212> TYPE: PRT
<213> ORGANISM: Artificial Sequence
<220> FEATURE:
<223> OTHER INFORMATION: FHR-1.3B4 VH

<400> SEQUENCE: 40

```
Gln Val Gln Leu Arg Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30
```

Gly Val Tyr Trp Val Arg Gln Ser Pro Gly Lys Gly Leu Glu Trp Leu
        35                  40                  45

Gly Val Ile Trp Ser Gly Gly Thr Thr Asp Tyr Ser Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Phe Gly Asn Tyr Ala Met Asp Tyr Trp Gly Gln Gly Thr Ser
            100                 105                 110

Val Thr Val Ser Ser
        115

<210> SEQ ID NO 41
<211> LENGTH: 16
<212> TYPE: DNA
<213> ORGANISM: Artificial Sequence
<220> FEATURE:
<223> OTHER INFORMATION: fake sequence to correct numbering

<400> SEQUENCE: 41
aaaaaaaaaa aaaaaa                                                    16

<210> SEQ ID NO 42
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 42
aaaaaaaaaa aaaaaaaa                                                  18

<210> SEQ ID NO 43
<211> LENGTH: 22
<212> TYPE: DNA
<213> ORGANISM: Artificial Sequence
<220> FEATURE:
<223> OTHER INFORMATION: fake sequence to correct numbering

<400> SEQUENCE: 43
aaaaaaaaaa aaaaaaaaaa aa                                             22

<210> SEQ ID NO 44
<211> LENGTH: 322
<212> TYPE: DNA
<213> ORGANISM: Artificial Sequence
<220> FEATURE:
<223> OTHER INFORMATION: FHR-1.3B4 VL

<400> SEQUENCE: 44
caaattgttc tctcccagtc tccaacaatc ctgtctgcat ctccagggga gaaggtcaca    60
atgacttgca gggccagctc aagtgtaact tacatgcact ggtaccagca gaagccagga   120 tcctcccca aaccctggat ttatgccaca tccaacctgg cttctggagt ccctgctcgc   180
ttcagtggca gtgggtctgg gacctcttac tctctcacaa tcagcagagt ggaggctgaa   240
gatgctgcca cttattactg ccagcagcgc agtagtagta acccgctcac gttcggtgct   300
gggaccaagc tggagctgaa at                                             322

<210> SEQ ID NO 45

```
<211> LENGTH: 17
<212> TYPE: DNA
<213> ORGANISM: Artificial Sequence
<220> FEATURE:
<223> OTHER INFORMATION: fake sequence to correct numbering

<400> SEQUENCE: 45
aaaaaaaaaa aaaaaaa                                                    17

<210> SEQ ID NO 46
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 46
aaaaaaaaaa aaaaaaaa                                                   18

<210> SEQ ID NO 47
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 47
aaaaaaaaaa aaaaaaaa                                                   18

<210> SEQ ID NO 48
<211> LENGTH: 349
<212> TYPE: DNA
<213> ORGANISM: Artificial Sequence
<220> FEATURE:
<223> OTHER INFORMATION: FHR-1.3B4 VH

<400> SEQUENCE: 48
caggtgcagc tgaggcagtc aggacctggc ctagtgcagc cctcacagag cctgtccatc    60
acctgcacag tctctggttt ctcattaact aactatggtg tatattgggt tcgccagtct   120
ccaggaaagg gtctggagtg gctgggagtg atatggagtg gaggaaccac tgactatagt   180
gcagctttca tatccagact gagcatcagc aaggacaact ccaagagcca agttttcttt   240
aaaatgaaca gtctgcaagc tgatgacaca gccatatact actgtgccag aatttggcac   300
tacgctatgg actacatggg gtcaaggaac ctcacaccgg tctccacag                349

<210> SEQ ID NO 49
<211> LENGTH: 11
<212> TYPE: PRT
<213> ORGANISM: Artificial Sequence
<220> FEATURE:
<223> OTHER INFORMATION: FHR-1.11E1 LC CDR1

<400> SEQUENCE: 49

Gln Ser Leu Val His Ser Asn Gly Asn Thr Tyr
1               5                   10

<210> SEQ ID NO 50
<211> LENGTH: 3
<212> TYPE: PRT
<213> ORGANISM: Artificial Sequence
<220> FEATURE:
<223> OTHER INFORMATION: FHR-1.11E1 LC CDR2

<400> SEQUENCE: 50
```

-continued

```
Lys Leu Ser
1

<210> SEQ ID NO 51
<211> LENGTH: 9
<212> TYPE: PRT
<213> ORGANISM: Artificial Sequence
<220> FEATURE:
<223> OTHER INFORMATION: FHR-1.11E1 LC CDR3

<400> SEQUENCE: 51

Ser Gln Ser Thr His Val Pro Phe Thr
1               5

<210> SEQ ID NO 52
<211> LENGTH: 112
<212> TYPE: PRT
<213> ORGANISM: Artificial Sequence
<220> FEATURE:
<223> OTHER INFORMATION: FHR-1.11E1 VL

<400> SEQUENCE: 52

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 53
<211> LENGTH: 8
<212> TYPE: PRT
<213> ORGANISM: Artificial Sequence
<220> FEATURE:
<223> OTHER INFORMATION: FHR-1.11E1 HC CDR1

<400> SEQUENCE: 53

Gly Phe Ser Leu Thr Asn Tyr Gly
1               5

<210> SEQ ID NO 54
<211> LENGTH: 7
<212> TYPE: PRT
<213> ORGANISM: Artificial Sequence
<220> FEATURE:
<223> OTHER INFORMATION: FHR-1.11E1 HC CDR2

<400> SEQUENCE: 54

Ile Trp Ser Gly Gly Asn Thr
1               5

<210> SEQ ID NO 55
<211> LENGTH: 12
<212> TYPE: PRT
<213> ORGANISM: Artificial Sequence
<220> FEATURE:
```

<223> OTHER INFORMATION: FHR-1.11E1 HC CDR3

<400> SEQUENCE: 55

Ala Lys Asn Gly Asp Tyr Gly Tyr Thr Met Asp Tyr
1               5                   10

<210> SEQ ID NO 56
<211> LENGTH: 118
<212> TYPE: PRT
<213> ORGANISM: Artificial Sequence
<220> FEATURE:
<223> OTHER INFORMATION: FHR-1.11E1 VH

<400> SEQUENCE: 56

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Pro Pro Gly Lys Gly Leu Glu Trp Leu
            35                  40                  45

Gly Val Ile Trp Ser Gly Gly Asn Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Gly Asp Tyr Gly Tyr Thr Met Asp Tyr Trp Gly Gln Gly Thr
            100                 105                 110

Ser Val Thr Val Ser Ser
        115

<210> SEQ ID NO 57
<211> LENGTH: 19
<212> TYPE: DNA
<213> ORGANISM: Artificial Sequence
<220> FEATURE:
<223> OTHER INFORMATION: fake sequence to correct numbering

<400> SEQUENCE: 57
aaaaaaaaaa aaaaaaaaa                                                    19

<210> SEQ ID NO 58
<211> LENGTH: 16
<212> TYPE: DNA
<213> ORGANISM: Artificial Sequence
<220> FEATURE:
<223> OTHER INFORMATION: fake sequence to correct numbering

<400> SEQUENCE: 58
aaaaaaaaaa aaaaaa                                                       16

<210> SEQ ID NO 59
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 59
aaaaaaaaaa aaaaaaaa                                                     18

<210> SEQ ID NO 60

```
<211> LENGTH: 337
<212> TYPE: DNA
<213> ORGANISM: Artificial Sequence
<220> FEATURE:
<223> OTHER INFORMATION: FHR-1.11E1 VL

<400> SEQUENCE: 60
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaactttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttcca     300
ttcacgttcg gctcggggac aaagttggaa ataaaac                              337

<210> SEQ ID NO 61
<211> LENGTH: 14
<212> TYPE: DNA
<213> ORGANISM: Artificial Sequence
<220> FEATURE:
<223> OTHER INFORMATION: fake sequence to correct numbering

<400> SEQUENCE: 61
aaaaaaaaaa aaaa                                                        14

<210> SEQ ID NO 62
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 62
aaaaaaaaaa aaaaaaaa                                                    18

<210> SEQ ID NO 63
<211> LENGTH: 23
<212> TYPE: DNA
<213> ORGANISM: Artificial Sequence
<220> FEATURE:
<223> OTHER INFORMATION: fake sequence to correct numbering

<400> SEQUENCE: 63
aaaaaaaaaa aaaaaaaaaa aaa                                              23

<210> SEQ ID NO 64
<211> LENGTH: 355
<212> TYPE: DNA
<213> ORGANISM: Artificial Sequence
<220> FEATURE:
<223> OTHER INFORMATION: FHR-1.11E1 VH

<400> SEQUENCE: 64
caggtgcagc tgaagcagtc aggacctggc ctagtgcagc cctcacagag cctgtccatc      60
acctgcacag tctctggttt ttcattaact aactatggtg tacactgggt tcgccagcct     120
ccaggaaagg gtctggagtg gctgggagtg atatggagtg gtggaaacac agactataat     180
gctgctttca tatccagact gagcatcagc aaggacaact ccaagagcca gttttctttt     240
aaaatgaaca gtctgcaagc tgatgacaca gccatatact actgtgccaa aaatgggggat    300 tacggctata ctatggacta ctggggtcaa ggaacctcag tcaccgtctc ctcag          355
```

-continued

```
<210> SEQ ID NO 65
<211> LENGTH: 5
<212> TYPE: PRT
<213> ORGANISM: Artificial Sequence
<220> FEATURE:
<223> OTHER INFORMATION: FHR-1.12F4 LC CDR1

<400> SEQUENCE: 65

Ser Ser Val Asn Tyr
1               5

<210> SEQ ID NO 66
<211> LENGTH: 3
<212> TYPE: PRT
<213> ORGANISM: Artificial Sequence
<220> FEATURE:
<223> OTHER INFORMATION: FHR-1.12F4 LC CDR2

<400> SEQUENCE: 66

Tyr Thr Ser
1

<210> SEQ ID NO 67
<211> LENGTH: 9
<212> TYPE: PRT
<213> ORGANISM: Artificial Sequence
<220> FEATURE:
<223> OTHER INFORMATION: FHR-1.12F4 LC CDR3

<400> SEQUENCE: 67

Gln Gln Phe Thr Ser Ser Pro Leu Thr
1               5

<210> SEQ ID NO 68
<211> LENGTH: 106
<212> TYPE: PRT
<213> ORGANISM: Artificial Sequence
<220> FEATURE:
<223> OTHER INFORMATION: FHR-1.12F4 VL

<400> SEQUENCE: 68

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
                20                  25                  30

Tyr Trp Tyr Gln Gln Lys Ser Asp Ala Ser Lys Leu Ser Trp Ile Tyr
            35                  40                  45

Tyr Thr Ser Asn Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Leu Thr
                85                  90                  95

Phe Gly Ala Gly Thr Lys Leu Glu Leu Lys
            100                 105

<210> SEQ ID NO 69
<211> LENGTH: 8
<212> TYPE: PRT
<213> ORGANISM: Artificial Sequence
<220> FEATURE:
<223> OTHER INFORMATION: FHR-1.12F4 HC CDR1

<400> SEQUENCE: 69
```

-continued

```
Gly Phe Ser Leu Thr Ser Tyr Gly
1               5

<210> SEQ ID NO 70
<211> LENGTH: 7
<212> TYPE: PRT
<213> ORGANISM: Artificial Sequence
<220> FEATURE:
<223> OTHER INFORMATION: FHR-1.12F4 HC CDR2

<400> SEQUENCE: 70

Ile Trp Ser Gly Gly Ser Thr
1               5

<210> SEQ ID NO 71
<211> LENGTH: 11
<212> TYPE: PRT
<213> ORGANISM: Artificial Sequence
<220> FEATURE:
<223> OTHER INFORMATION: FHR-1.12F4 HC CDR3

<400> SEQUENCE: 71

Ala Arg Asn Gly Gly Asn Tyr Tyr Phe Asp Tyr
1               5                   10

<210> SEQ ID NO 72
<211> LENGTH: 117
<212> TYPE: PRT
<213> ORGANISM: Artificial Sequence
<220> FEATURE:
<223> OTHER INFORMATION: FHR-1.12F4 VH

<400> SEQUENCE: 72

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Val Ile Trp Ser Gly Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Gly Gly Asn Tyr Tyr Phe Asp Tyr Trp Gly Gln Gly Thr Thr
            100                 105                 110

Leu Thr Val Ser Ser
        115

<210> SEQ ID NO 73
<211> LENGTH: 19
<212> TYPE: DNA
<213> ORGANISM: Artificial Sequence
<220> FEATURE:
<223> OTHER INFORMATION: fake sequence to correct numbering

<400> SEQUENCE: 73
aaaaaaaaaa aaaaaaaaa                                            19

<210> SEQ ID NO 74
<211> LENGTH: 20
<212> TYPE: DNA
```

<213> ORGANISM: Artificial Sequence
<220> FEATURE:
<223> OTHER INFORMATION: fake sequence to correct numbering

<400> SEQUENCE: 74
aaaaaaaaaa aaaaaaaaaa                                             20

<210> SEQ ID NO 75
<211> LENGTH: 18
<212> TYPE: DNA
<213> ORGANISM: Artificial Sequence
<220> FEATURE:
<223> OTHER INFORMATION: fake sequence to correct numbering

<400> SEQUENCE: 75
aaaaaaaaaa aaaaaaaa                                               18

<210> SEQ ID NO 76
<211> LENGTH: 319
<212> TYPE: DNA
<213> ORGANISM: Artificial Sequence
<220> FEATURE:
<223> OTHER INFORMATION: FHR-1.12F4 VL

<400> SEQUENCE: 76
gaaaatgtgc tcacccagtc tccagcaatc atgtctgcat ctctagggga gaaggtcacc    60
atgagctgca gggccagctc aagtgtaaat tacatgtact ggtaccagca gaagtcagat   120
gcctccccca actcatggat ttattacaca tccaacctgg ctcctggagt cccagctcgc   180
ttcagtggca gtgggtctgg gaactcttat tctctcacaa tcagcagcat ggagggtgaa   240
gatgctgcca cttattactg ccagcagttt actagttccc cactcacgtt cggtgctggg   300
accaagctgg agctgaaac                                              319

<210> SEQ ID NO 77
<211> LENGTH: 15
<212> TYPE: DNA
<213> ORGANISM: Artificial Sequence
<220> FEATURE:
<223> OTHER INFORMATION: fake sequence to correct numbering

<400> SEQUENCE: 77
aaaaaaaaaa aaaaa                                                  15

<210> SEQ ID NO 78
<211> LENGTH: 16
<212> TYPE: DNA
<213> ORGANISM: Artificial Sequence
<220> FEATURE:
<223> OTHER INFORMATION: fake sequence to correct numbering

<400> SEQUENCE: 78
aaaaaaaaaa aaaaaa                                                 16

<210> SEQ ID NO 79
<211> LENGTH: 17
<212> TYPE: DNA
<213> ORGANISM: Artificial Sequence
<220> FEATURE:
<223> OTHER INFORMATION: fake sequence to correct numbering

<400> SEQUENCE: 79
aaaaaaaaaa aaaaaaa                                                17

-continued

```
<210> SEQ ID NO 80
<211> LENGTH: 352
<212> TYPE: DNA
<213> ORGANISM: Artificial Sequence
<220> FEATURE:
<223> OTHER INFORMATION: FHR-1.12F4 VH

<400> SEQUENCE: 80
caggtgcagc tgaagcagtc aggacctggc ctagtgcagc cctcacagag cctgtccatc       60
acctgcacag tctctggttt ctcattaact agctatggtg tacactgggt tcgccagtct      120
ccaggaaagg gtctggagtg gctgggagtg atatggagtg gtggaagcac agactataat      180
gcagctttca tatccagact gagcatcagc aaggacaatt ccaagagcca gttttctttt      240
aaaatgaaca gtctgcaagc taatgacaca gccatatatt actgtgccag aaacggaggt      300
aactactact ttgactactg gggccaaggc accactctca cagtctcctc ag             352

<210> SEQ ID NO 81
<211> LENGTH: 12
<212> TYPE: PRT
<213> ORGANISM: Artificial Sequence
<220> FEATURE:
<223> OTHER INFORMATION: FHR-1.14C4 LC CDR1

<400> SEQUENCE: 81

Gln Ser Leu Phe Asn Ser Gly Asn Gln Lys Asn Tyr
1               5                   10

<210> SEQ ID NO 82
<211> LENGTH: 3
<212> TYPE: PRT
<213> ORGANISM: Artificial Sequence
<220> FEATURE:
<223> OTHER INFORMATION: FHR-1.14C4 LC CDR2

<400> SEQUENCE: 82

Trp Ala Ser
1

<210> SEQ ID NO 83
<211> LENGTH: 9
<212> TYPE: PRT
<213> ORGANISM: Artificial Sequence
<220> FEATURE:
<223> OTHER INFORMATION: FHR-1.14C4 LC CDR3

<400> SEQUENCE: 83

Gln Asn Asp Tyr Ser Tyr Pro Leu Thr
1               5

<210> SEQ ID NO 84
<211> LENGTH: 113
<212> TYPE: PRT
<213> ORGANISM: Artificial Sequence
<220> FEATURE:
<223> OTHER INFORMATION: FHR-1.14C4 VL

<400> SEQUENCE: 84

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
                20                  25                  30

Gly Asn Gln Lys Asn Tyr Leu Thr Trp Tyr Gln Gln Lys Pro Gly Gln
            35                  40                  45
```

```
Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                    85                  90                  95

Asp Tyr Ser Tyr Pro Leu Thr Phe Gly Ala Gly Thr Lys Leu Glu Leu
                100                 105                 110

Lys
```

```
<210> SEQ ID NO 85
<211> LENGTH: 8
<212> TYPE: PRT
<213> ORGANISM: Artificial Sequence
<220> FEATURE:
<223> OTHER INFORMATION: FHR-1.14C4 HC CDR1

<400> SEQUENCE: 85

Gly Tyr Ser Phe Thr Gly Tyr Asn
1               5
```

```
<210> SEQ ID NO 86
<211> LENGTH: 8
<212> TYPE: PRT
<213> ORGANISM: Artificial Sequence
<220> FEATURE:
<223> OTHER INFORMATION: FHR-1.14C4 HC CDR2

<400> SEQUENCE: 86

Ile Asp Pro Tyr Tyr Gly Asp Thr
1               5
```

```
<210> SEQ ID NO 87
<211> LENGTH: 12
<212> TYPE: PRT
<213> ORGANISM: Artificial Sequence
<220> FEATURE:
<223> OTHER INFORMATION: FHR-1.14C4 HC CDR3

<400> SEQUENCE: 87

Ala Arg Ala Phe Tyr Arg Asp Tyr Ala Leu Asp Tyr
1               5                   10
```

```
<210> SEQ ID NO 88
<211> LENGTH: 119
<212> TYPE: PRT
<213> ORGANISM: Artificial Sequence
<220> FEATURE:
<223> OTHER INFORMATION: FHR-1.14C4 VH

<400> SEQUENCE: 88

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Asn Met His Trp Val Lys Gln Ser Asn Gly Thr Ser Leu Glu Trp Ile
        35                  40                  45

Gly Lys Ile Asp Pro Tyr Tyr Gly Asp Thr Ser Tyr Asn Gln Arg Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
```

-continued

```
                      85            90              95
Ala Arg Ala Phe Tyr Arg Asp Tyr Ala Leu Asp Tyr Trp Gly Arg Gly
               100             105             110

Thr Ser Val Thr Val Ser Ser
        115

<210> SEQ ID NO 89
<211> LENGTH: 340
<212> TYPE: DNA
<213> ORGANISM: Artificial Sequence
<220> FEATURE:
<223> OTHER INFORMATION: FHR-1.14C4 VL

<400> SEQUENCE: 89
gacattgtga tgacacagtc tccatcctcc ctgactgtga cagcaggaga gaaggtcact      60
atgagctgca agtccagtca gagtctgttt aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
ccgctcacgt tcggtgctgg gaccaagctg gagctgaaac                           340

<210> SEQ ID NO 90
<211> LENGTH: 360
<212> TYPE: DNA
<213> ORGANISM: Artificial Sequence
<220> FEATURE:
<223> OTHER INFORMATION: FHR-1.14C4 VH

<400> SEQUENCE: 90
vhgaggtcca gctgcagcag tctggacctg agctggagaa gcctggcgct tcagtgaaga      60
tatcctgcaa ggcttctggt tactcattca ctggctacaa catgcactgg gtgaagcaga     120
gcaatggaac gagccttgag tggattggaa aaattgatcc ttactatggt gatactagct     180
acaaccagag gttcaagggc aaggccacat tgactgtaga caaatcctcc agcacagcct     240
acatgcagct caagagcctg acatctgagg actctgcagt ctattactgt gcaagagcgt     300
tctatagaga ctatgctttg gactactggg gtcgaggaac ctcagtcacc gtctcttcag     360

<210> SEQ ID NO 91
<211> LENGTH: 5
<212> TYPE: PRT
<213> ORGANISM: Artificial Sequence
<220> FEATURE:
<223> OTHER INFORMATION: LC CDR1 consensus sequence
<220> FEATURE:
<221> NAME/KEY: VARIANT
<222> LOCATION: (4)..(4)
<223> OTHER INFORMATION: may be T or N

<400> SEQUENCE: 91

Ser Ser Val Arg Tyr
1               5

<210> SEQ ID NO 92
<211> LENGTH: 3
<212> TYPE: PRT
<213> ORGANISM: Artificial Sequence
<220> FEATURE:
<223> OTHER INFORMATION: LC CDR2 consensus sequence
<220> FEATURE:
<221> NAME/KEY: VARIANT
<222> LOCATION: (1)..(1)
```

```
<223> OTHER INFORMATION: may be K or Y
<220> FEATURE:
<221> NAME/KEY: VARIANT
<222> LOCATION: (2)..(2)
<223> OTHER INFORMATION: may be L

<400> SEQUENCE: 92

Ala Thr Ser
1

<210> SEQ ID NO 93
<211> LENGTH: 8
<212> TYPE: PRT
<213> ORGANISM: Artificial Sequence
<220> FEATURE:
<223> OTHER INFORMATION: HC CDR consensus sequence
<220> FEATURE:
<221> NAME/KEY: VARIANT
<222> LOCATION: (1)..(1)
<223> OTHER INFORMATION: may be G
<220> FEATURE:
<221> NAME/KEY: VARIANT
<222> LOCATION: (6)..(6)
<223> OTHER INFORMATION: may be S
<220> FEATURE:
<221> NAME/KEY: VARIANT
<222> LOCATION: (7)..(7)
<223> OTHER INFORMATION: may be Y

<400> SEQUENCE: 93

Asp Phe Ser Leu Thr Asn Ser Gly
1               5

<210> SEQ ID NO 94
<211> LENGTH: 7
<212> TYPE: PRT
<213> ORGANISM: Artificial Sequence
<220> FEATURE:
<223> OTHER INFORMATION: HC CDR2 consensus sequence
<220> FEATURE:
<221> NAME/KEY: VARIANT
<222> LOCATION: (6)..(6)
<223> OTHER INFORMATION: May be N or S

<400> SEQUENCE: 94

Ile Trp Ser Gly Gly Thr Thr
1               5

<210> SEQ ID NO 95
<211> LENGTH: 11
<212> TYPE: PRT
<213> ORGANISM: Artificial Sequence
<220> FEATURE:
<223> OTHER INFORMATION: HC CDR3 consensus sequence
<220> FEATURE:
<221> NAME/KEY: VARIANT
<222> LOCATION: (4)..(4)
<223> OTHER INFORMATION: May be G
<220> FEATURE:
<221> NAME/KEY: VARIANT
<222> LOCATION: (8)..(8)
<223> OTHER INFORMATION: May be Y
<220> FEATURE:
<221> NAME/KEY: VARIANT
<222> LOCATION: (9)..(9)
<223> OTHER INFORMATION: May be M or F

<400> SEQUENCE: 95

Ala Arg Asn Phe Gly Asn Tyr Ala Val Asp Tyr
1               5                   10
```

```
<210> SEQ ID NO 96
<211> LENGTH: 5
<212> TYPE: PRT
<213> ORGANISM: Artificial Sequence
<220> FEATURE:
<223> OTHER INFORMATION: LC CDR1 concensus sequence
<220> FEATURE:
<221> NAME/KEY: VARIANT
<222> LOCATION: (4)..(4)
<223> OTHER INFORMATION: May be T

<400> SEQUENCE: 96

Ser Ser Val Arg Tyr
1               5

<210> SEQ ID NO 97
<211> LENGTH: 3
<212> TYPE: PRT
<213> ORGANISM: Artificial Sequence
<220> FEATURE:
<223> OTHER INFORMATION: LC CDR2 consensus sequence

<400> SEQUENCE: 97

Ala Thr Ser
1

<210> SEQ ID NO 98
<211> LENGTH: 8
<212> TYPE: PRT
<213> ORGANISM: Artificial Sequence
<220> FEATURE:
<223> OTHER INFORMATION: HC CDR1 consensus sequence
<220> FEATURE:
<221> NAME/KEY: VARIANT
<222> LOCATION: (1)..(1)
<223> OTHER INFORMATION: May be G
<220> FEATURE:
<221> NAME/KEY: VARIANT
<222> LOCATION: (7)..(7)
<223> OTHER INFORMATION: May be Y

<400> SEQUENCE: 98

Asp Phe Ser Leu Thr Asn Ser Gly
1               5

<210> SEQ ID NO 99
<211> LENGTH: 7
<212> TYPE: PRT
<213> ORGANISM: Artificial Sequence
<220> FEATURE:
<223> OTHER INFORMATION: HC CDR2 consensus sequence

<400> SEQUENCE: 99

Ile Trp Ser Gly Gly Thr Thr
1               5

<210> SEQ ID NO 100
<211> LENGTH: 11
<212> TYPE: PRT
<213> ORGANISM: Artificial Sequence
<220> FEATURE:
<223> OTHER INFORMATION: HC CDR3 consensus sequence
```

-continued

```
<220> FEATURE:
<221> NAME/KEY: VARIANT
<222> LOCATION: (9)..(9)
<223> OTHER INFORMATION: May be M

<400> SEQUENCE: 100

Ala Arg Asn Phe Gly Asn Tyr Ala Val Asp Tyr
1               5                   10
```

FACTOR H POTENTIATING ANTIBODIES AND USES THEREOF

CROSS-REFERENCE TO RELATED PATENT APPLICATIONS

This application is a Continuation Application of U.S. application Ser. No. 16/961,737, filed on Jul. 13, 2020, which is a U.S. National Stage Application under 35 U.S.C. § 371 of International Patent Application No. PCT/NL2019/050018 filed Jan. 15, 2019, which claims the benefit of priority of European Patent Application No. EP 18151726.9 filed Jan. 15, 2018, each of which are incorporated by reference in their entireties.

FIELD OF THE INVENTION

The invention relates to the field of immunology and medicine. In particular, the invention relates to factor H specific antibodies and uses thereof.

BACKGROUND

The complement system is an important element of innate immunity that contributes to the protection of many organisms such as mammals against invading pathogens. The complement system consists of over 30 different components which are mainly synthesized in the liver. Activation of the complement system occurs by three different pathways, the classical pathway, the lectin pathway and the alternative pathway. The three pathways converge at the formation of a C3 convertase, which are different for each pathway but have similar activity.

In the classical complement pathway, activation of the complement component (C) 1 complex, consisting of C1q, C1r and C1s, occurs upon binding to antibody-antigen complexes. The C1 complex cleaves C4 and C2 leading to the formation of a C3 convertase consisting of C4bC2a. The C3 convertase cleaves C3 into the active components C3a and C3b. In the lectin pathway, mannose binding lectin binds to mannose residues on pathogenic surfaces which activates serine proteases MASP-1 and MASP-2 that are able to cleave C4 and C2. As in the classical pathway, this leads to the formation of the C4bC2a C3 convertase. This C3 convertase can bind C3b to form a C5 convertase. Contrary to the classical and lectin pathways, the alternative pathway has a low level of continuous activity due to spontaneous hydrolysis of C3 to C3($H_2O$) in plasma. This C3b-like C3($H_2O$) can form a fluid phase C3 convertase by binding factor B (FB) which in turn is activated into Bb by factor D. Similarly, when C3b binds to a surface, it may bind FB to form C3bB. This complex is cleaved by factor D to C3bBb which is the C3 convertase of the alternative pathway that can be stabilized by properdin (factor P) to C3bBbP. This C3 convertase is able to cleave C3 into C3a and C3b. In addition to this process the alternative pathway acts as amplification loop for the classical and lectin activation pathways as C3b generated in these pathways may act as starting point for the alternative pathway. Thereby, the amplification loop results in a reinforcement of the classical and lectin pathway. The C3 convertase formed in one of the three activation pathways can bind C3b to form a C5 convertase. The C5 convertases of all three complement pathways activate C5 into C5a and C5b which initiates the terminal pathway of the complement system. C5b binds C6, C7, C8 and C9 to form the membrane attack complex (MAC) which forms a transmembrane channel and causes cell lysis.

Next to forming a pore in the membrane of pathogens, complement helps clearing pathogens or altered self-cells by opsonisation with C3b molecules and production of pro-inflammatory peptides such as C3a and C5a that attract and activate immune cells to the site of infection. Because of the strong pro-inflammatory nature of complement, host cells are well protected by several membrane and soluble complement-regulating proteins.

The alternative pathway contributes for 80-90% to total complement activity. Regulation of this pathway is therefore crucial. C3($H_2O$) that is formed by spontaneous hydrolysis of C3, and C3b are generally, if not bound by a pathogen, rapidly inactivated by factor H (FH), factor I (FI) and host cell surface molecules thereby inhibiting the formation of the C3 convertases. CD55 (also termed decay accelerating factor or DAF) binds C3b at the host cell surface. FI cleaves C3b to an inactive form but is dependent on co-factors either expressed on cell surfaces (CD46, MCP) or circulating in plasma (FH). FH is a plasma glycoprotein that is essential for controlling the alternative pathway of complement both in solution and on cell surfaces. FH binds C3b at the same position as FB, thereby preventing the formation of C3 convertases. FH also has decay accelerating activity, i.e. it promotes the dissociation of alternative pathway C3 convertases once they have been formed. Whether FH binds to C3b is determined by the carbohydrates present on the cell surface. Sialic acid, glycosaminoglycans and heparin present on the host cell surface promotes binding of FH to C3b, whereas binding of C3b to molecules expressed on the surface of pathogens results in binding of FB. FH thus exerts its complement inhibitory activity on host cells but not on the surface of pathogenic cells because the cell surface molecules that bind FH are expressed on host cells but generally not on pathogenic cells. FH contains 20 complement control protein (CCP) domains, numbered 1-20 starting at the N-terminus of FH. The CCP domains are also referred to as short consensus repeats (SCR) or sushi domains. CCPs 1~4 are domains involved in regulation and CCPs 19-20 are involved in binding C3b and CCP s 6, 7, 8, 19 and 20 bind to GAGs and sialic acid expressed at the surface of cells. Antibodies that bind CCP19 and/or CCP20 inhibit activity of FH.

Factor H-related proteins (CFHRs) are plasma glycoproteins related in structure and antigenicity to FH. The FHR proteins are also composed of CCP domains and these bear varying degrees of homology to the CCP domains found in FH. For instance, FHR1 comprises domains corresponding to CCP6, CCP7, CCP18, CCP19 and CCP20. In contrast to FH, CFHRs have no strong complement inhibitory activity. A common feature of CFHRs is that they bind to the C3b component of complement, thereby competing with FH for binding to C3b and are thus considered to be positive regulators of the alternative pathway of complement.

FH deficiency or impaired recognition of host surfaces due to mutations is associated with complement-mediated tissue damage and disease. Next to controlling complement activation during normal hemostasis, FH also plays an important role in limiting complement mediated damage of diseased cells and tissues. Multiple mutations in the FH gene have been described that may lead to loss of function of the FH protein. The C-terminal region of FH is a hotspot for mutations in disease. This is a critical region for binding of FH to host cells. Most disease-associated mutations in this region interfere with FH binding. Most patients with a mutated FH gene have heterozygous mutations, meaning that approximately half of the circulating FH has normal function. However, this apparently is not sufficient to protect self surfaces in certain conditions in which complement is activated. FH deficiency may lead to kidney disease such as membranoproliferative glomerulenephritis (MPGN) and atypical hemolytic uremic syndrome (aHUS). More recently a relationship has been described between FH mutations and age-related macular disease (AMD).

Currently the standard treatment for FH deficiency, such as in aHUS, is plasma supplementation or plasma exchange therapy. With such therapy deficient complement regulators are supplemented. Plasma exchange therapy in addition removes mutant complement factors and/or autoantibodies directed against complement factors. However, plasma therapy also has some limitations. No prospective clinical studies have shown that plasma exchange therapy is safe or effective in treating aHUS and efficiency of plasma therapy may depend on the underlying mutations. Some patients develop anaphylactic reactions to fresh frozen plasma, which may require cessation of any form of plasma therapy. Moreover, plasma exchange may worsen the clinical picture of aHUS due to the administration of plasma-derived active pathogenic complement components.

Recently the therapeutic monoclonal antibody eculizumab has been approved for treatment of aHUS and paroxysmal nocturnal hemoglobinuria (PNH) in several countries, among which the US and European countries. Eculizumab is a humanized mouse monoclonal antibody specific for C5 that prevents cleavage of C5 to C5a and C5b. It thus prevents activation of the terminal pathway and decreases the influx of immune cells. However, the use of eculizumab is associated with unwanted side effects. As it blocks C5, which is a crucial component for the initiation of the terminal pathway, patients treated with eculizumab become vulnerable to infection with encapsulated bacteria (such as *Neisseria meningitidis*), the clearance of which is very dependent on MAC formation. Therefore, vaccination against the meningococcus is required for patients prior to receiving treatment with eculizumab. Further, since eculizumab acts downstream of C3, C3 deposition is maintained, which is detrimental in several disorders involving unwanted or excessive complement activation. In addition, high costs are involved with eculizumab treatment and the availability of the antibody is limited.

A mouse monoclonal antibody that binds CCP18 is described by Cheng et al. (Clinical Chemistry, 2005). It is described that this antibody, called X52.1, increases binding of FH to C3b and C3d which is thought to be caused by dimerization of FH. The increased binding of FH to C3b and C3d induced by X52.1 results in an increased complement mediated lysis of cells, including RBCs and several types of cancer cells as shown by Corey et al. (J Biol Chem. 2000). This demonstrates that antibody X52.1 inhibits the complement inhibitory activity of FH. Indeed, Corey et al. suggests that the antibody can be used in the treatment of cancer by enhancing complement-mediated lysis of cancer cells.

WO 2016/028150 describes an agonistic anti-FH antibody referred to as FH.07, which inhibits alternative pathway activation as shown by an increased binding of FH to C3b, inhibition of mediated C3 deposition and inhibition of hemolytic activity. Fab' and F(ab')2 fragments of the antibody were shown to have the same FH potentiating effect.

There is a continuous need for novel and improved therapeutic agents that bind FH, such as agent that are useful in the treatment of disorders associated with unwanted or excessive complement activation.

SUMMARY OF THE INVENTION

It is an object of the invention to provide novel antibodies that bind FH. It is a further object to provide antibodies that specifically recognize an epitope in FH binding of which results in potentiation of FH activity, in particular an epitope located in domain CCP18 of FH. It is a further object of the invention to provide antibodies that have a high binding affinity for FH.

The invention therefore provides an isolated, synthetic or recombinant antibody or antigen binding fragment thereof that specifically binds to factor H (FH) and potentiates FH activity, wherein the antibody or fragment has a binding affinity for FH with a $K_D$ of $2.5\times10^{-8}$ M or less and/or a binding affinity for a FH fragment comprised of CCP18-20 with a $K_D$ of $0.1\times10^{-9}$ M or less, preferably wherein said antibody or fragment has a binding affinity for FH with a $K_D$ of $1.25\times10^{-8}$ M or less and/or a binding affinity for a FH fragment comprised of CCP18-20 with a $K_D$ of $0.04\times10^{-9}$M or less, more preferably wherein said antibody or fragment has a binding affinity for FH with a $K_D$ of $1.25\times10^{-8}$ M or less and/or a binding affinity for a FH fragment comprised of CCP18-20 with a $K_D$ of $0.04\times10^{-9}$ M or less of $0.1\times10^{-9}$ M or less. A preferred antibody or fragment preferably has a binding affinity for FH with a $K_D$ of $0.6\times10^{-8}$ M or less and/or a binding affinity for a FH fragment comprised of CCP18-20 with a $K_D$ of $0.6\times10^{-11}$ M or less. Said antibody or fragment preferably inhibits C3 deposition on LPS in vitro with an $IC_{50}$ value of 38 nM or less and/or inhibits hemolytic activity in vitro with an $IC_{50}$ value of 150 nM or less. The antibody or fragment preferably increases binding affinity ($K_D$) of FH for C3b in vitro to at most 2 μM and/or increases binding affinity of FH for C3b in vitro at least 3 times. The binding affinity is determined using surface plasmon resonance (SPR).

In a further aspect, the invention provides an isolated, synthetic or recombinant antibody or antigen binding fragment thereof that specifically binds to factor H (FH) and potentiates FH activity, wherein the antibody or fragment inhibits C3 deposition on LPS in vitro with an $IC_{50}$ value of 38 nM or less.

In a further aspect, the invention provides an isolated, synthetic or recombinant antibody or antigen binding fragment thereof that specifically binds to factor H (FH) and potentiates FH activity, wherein the antibody or fragment increases binding affinity ($K_D$) of FH for C3b in vitro to at most 2 μM and/or increases binding affinity of FH for C3b in vitro at least 3 times.

In a further aspect, the invention provides an isolated, synthetic or recombinant antibody or antigen binding fragment thereof that specifically binds to factor H (FH) and potentiates FH activity, wherein the antibody or fragment inhibits hemolytic activity in vitro with an $IC_{50}$ value of 150 nM or less, preferably 130 nM or less, more preferably 115 nM or less more preferably 105 nM or less, more preferably 100 nM or less.

The antibody or fragment according to the invention preferably binds to complement control protein domain 18 (CCP18) of factor H (FH). Said FH activity is preferably inhibition of alternative complement activation. inhibition of alternative complement activation comprises: an inhibition of hemolytic activity, an inhibition of complement component 3 (C3) deposition on cells, and/or an increase of binding of FH to C3b, iC3b and/or C3d.

In a further aspect, the invention provides an isolated, synthetic or recombinant antibody or antigen binding fragment thereof that specifically binds to complement control protein domain 18 (CCP18) of factor H (FH) comprising:
a light chain CDR1 sequence having the sequence SSVXY, wherein X is R, T or N (SEQ ID NO:91) or the sequence QSLVHSNGNTY (SEQ ID NO:49), a light chain CDR2 sequence having the sequence $X_1X_2S$ wherein $X_1$=A, K or Y and $X_2$=T or L (SEQ ID NO:92), a light chain CDR3 having a sequence selected from the group consisting of QQWGTKPPT (SEQ ID NO:19), QQRSSSNPLT (SEQ ID NO:35), SQSTHVPFT (SEQ ID NO:51) and QQFTSSPLT (SEQ ID NO:67), a heavy chain CDR1 having the sequence $X_1FSLTX_2X_3G$, wherein $X_1$=D or G, $X_2$=N or S and $X_3$=S or Y (SEQ ID NO:93), a heavy chain CDR2 having the sequence IWSGGXT, wherein x=T, N or S (SEQ ID NO:94), and a heavy chain CDR3 sequence having the sequence $ARNX_1GNYX_2X_3DY$, wherein $X_1$=F or G, $X_2$=A or Y and $X_3$=V, M or F (SEQ ID NO:95) or AKNGDYGYTMDY (SEQ ID NO:55).

In a further aspect, the invention provides an isolated, synthetic or recombinant antibody or antigen binding fragment thereof that specifically binds to complement control protein domain 18 (CCP18) of factor H (FH) comprising:

a light chain CDR1 sequence having the sequence SSVXY, wherein X is R or T (SEQ ID NO:96), a light chain CDR2 sequence having the sequence ATS (SEQ ID NO:97), a light chain CDR3 having a sequence selected from the group consisting of QQWGTKPPT (SEQ ID NO:19) and QQRSSSNPLT (SEQ ID NO:35), a heavy chain CDR1 having the sequence $X_1FSLTNX_2G$, wherein $X_1$=D or G and $X_2$=S or Y (SEQ ID NO:98), a heavy chain CDR2 having the sequence IWSGGTT (SEQ ID NO:99), and a heavy chain CDR3 sequence having the sequence ARNFGNYAXDY, wherein X=V or M (SEQ ID NO:100).

In a further aspect, the invention provides an isolated, synthetic or recombinant antibody or antigen binding fragment thereof that specifically binds to complement control protein domain 18 (CCP18) of factor H (FH) comprising a light chain CDR1 sequence having the sequence SSVTY (SEQ ID NO:17), a light chain CDR2 sequence having the sequence ATS (SEQ ID NO:18) and a light chain CDR3 having the sequence QQWGTKPPT (SEQ ID NO:19), a heavy chain CDR1 having the sequence DFSLTNSG (SEQ ID NO:21), a heavy chain CDR2 having the sequence IWSGGTT (SEQ ID NO:22), and a heavy chain CDR3 sequence having the sequence ARNFGNYAVDY (SEQ ID NO:23). The antibody or fragment preferably has a binding affinity for FH with a $K_D$ of $2.5 \times 10^{-8}$M or less and/or a binding affinity for a FH fragment comprised of CCP18-20 with a $K_D$ of $0.1 \times 10^{-9}$ M or less, preferably wherein said antibody or fragment has a binding affinity for FH with a $K_D$ of $1.25 \times 10^{-8}$ M or less and/or a binding affinity for a FH fragment comprised of CCP18-20 with a $K_D$ of $0.04 \times 10^{-9}$M or less. The antibody or fragment preferably inhibits C3 deposition on LPS in vitro with an $IC_{50}$ value of 38 nM or less, preferably with an $C_{50}$ value of 30 nM or less, more preferably with an $C_{50}$ value of 27 nM or less. The antibody or fragment preferably inhibits hemolytic activity in vitro with an $IC_{50}$ value of 150 nM or less, preferably with an $IC_{50}$ value of 130 nM or less, more preferably with an $IC_{50}$ value of 100 nM or less. The antibody or fragment preferably increases binding affinity ($K_D$) of FH for C3b in vitro to at most 2 µM, more preferably 1.8 µM and/or increases binding affinity of FH for C3b in vitro at least 3 times, more preferably 3.5 times.

In a further aspect, the invention provides an isolated, synthetic or recombinant antibody or antigen binding fragment thereof that specifically binds to factor H (FH) comprising a light chain CDR1 sequence having the sequence SSVTY (SEQ ID NO:33), a light chain CDR2 sequence having the sequence ATS (SEQ ID NO:34) and a light chain CDR3 having the sequence QQRSSSNPLT (SEQ ID NO:35), a heavy chain CDR1 having the sequence GFSLTNYG (SEQ ID NO:37), a heavy chain CDR2 having the sequence IWSGGTT (SEQ ID NO:38), and a heavy chain CDR3 sequence having the sequence ARNFGNYAMDY (SEQ ID NO:39). The antibody or fragment preferably has a binding affinity for FH with a $K_D$ of $2.5 \times 10^{-8}$ M or less and/or a binding affinity for a FH fragment comprised of CCP18-20 with a $K_D$ of $0.1 \times 10^{-9}$M or less, preferably wherein said antibody or fragment has a binding affinity for FH with a $K_D$ of $0.6 \times 10^{-8}$ M or less and/or a binding affinity for a FH fragment comprised of CCP18-20 with a $K_D$ of $0.6 \times 10^{-11}$ M or less. The antibody or fragment preferably increases binding affinity ($K_D$) of FH for C3b in vitro to at most 2 µM, more preferably 1.95 µM and/or increases binding affinity of FH for C3b in vitro at least 3 times, more preferably 3.1 times.

In a further aspect, the invention provides an isolated, synthetic or recombinant antibody or antigen binding fragment thereof that specifically binds to factor H (FH) comprising a light chain CDR1 sequence having the sequence QSLVHSNGNTY (SEQ ID NO:49), a light chain CDR2 sequence having the sequence KLS (SEQ ID NO:50) and a light chain CDR3 having the sequence SQSTHVPFT (SEQ ID NO:51), a heavy chain CDR1 having the sequence GFSLTNYG (SEQ ID NO:53), a heavy chain CDR2 having the sequence IWSGGNT (SEQ ID NO:54), and a heavy chain CDR3 sequence having the sequence AKNGDYGYTMDY (SEQ ID NO:55).

In a further aspect, the invention provides an isolated, synthetic or recombinant antibody or antigen binding fragment thereof that specifically binds to factor H (FH) comprising a light chain CDR1 sequence having the sequence SSVNY (SEQ ID NO:65), a light chain CDR2 sequence having the sequence YTS (SEQ ID NO:66) and a light chain CDR3 having the sequence of QQFTSSPLT (SEQ ID NO:67), a heavy chain CDR1 having the sequence GFSLT-SYG (SEQ ID NO:69), a heavy chain CDR2 having the sequence IWSGGST (SEQ ID NO:70), and a heavy chain CDR3 sequence having the sequence ARNGGNYYFDY (SEQ ID NO:71).

In a further aspect, the invention provides an isolated, synthetic or recombinant antibody or antigen binding fragment thereof that specifically binds to factor H (FH) comprising a variable light chain sequence comprising a sequence which has at least 80% sequence identity to a sequence selected from the group consisting of QIVLSQ-SPAILSASPGEKVTMTCRASSSVRYMHWYQQK-AGSSPTAWIFATSNLA SGVPPRFSGSGSGTSYS-LTISRVEAEDAATYYCQQWGTKPPTFGAGTKLELK (SEQ ID NO:20) and a variable heavy chain sequence comprising a sequence which has at least 80% sequence identity to the sequence

```
                                    (SEQ ID NO: 24)
QVQLKQSGPGLVQPSQSLSITCTVSDFSLTNSGVHWVRQSPGKGLEWLG

VIWSGGTTEYNAAFMSRLTITKDNSKSQVFFKMNSLLVDDTGIYYCARN

FGNYAVDYWGQGTSVTVSS.
```

In a further aspect, the invention provides an isolated, synthetic or recombinant antibody or antigen binding fragment thereof that specifically binds to factor H (FH) comprising a variable light chain sequence comprising a sequence which has at least 80% sequence identity to the sequence QIVLSQSPTILSASPGEKVTMT-CRASSSVTYMHWYQQKPGSSPKPWIYATSNLAS GVPARFSGSGSGTSYSLTISRVEAE-DAATYYCQQRSSSNPLTFGAGTKLELK (SEQ ID NO:36) and a variable heavy chain sequence comprising a sequence which has at least 80% sequence identity to the sequence

```
                                   (SEQ ID NO: 40)
QVQLRQSGPGLVQPSQSLSITCTVSGFSLTNYGVYWVRQSPGKGLEWLG

VIWSGGTTDYSAAFISRLSISKDNSKSQVFFKMNSLQADDTAIYYCARN

FGNYAMDYWGQGTSVTVSS.
```

In a further aspect, the invention provides an isolated, synthetic or recombinant antibody or antigen binding fragment thereof that specifically binds to factor H (FH) comprising a variable light chain sequence comprising a sequence which has at least 80% sequence identity to the sequence DVVMTQTPLSLPVSLGDQASIS-CRSSQSLVHSNGNTYLHWYLQKPGQSPKLLIY KLSNRFSGVPDRFSGSGSGTDFTLKISRVEAE-DLGVYFCSQSTHVPFTFGSGTKL EIK (SEQ ID NO:52) and a variable heavy chain sequence comprising a sequence which has at least 80% sequence identity to the sequence

```
                                   (SEQ ID NO: 56)
QVQLKQSGPGLVQPSQSLSITCTVSGFSLTNYGVHWVRQPPGKGLEWLG

VIWSGGNTDYNAAFISRLSISKDNSKSQVFFKMNSLQADDTAIYYCAKN

GDYGYTMDYWGQGTSVTVSS.
```

In a further aspect, the invention provides an isolated, synthetic or recombinant antibody or antigen binding fragment thereof that specifically binds to factor H (FH) comprising a variable light chain sequence comprising a sequence which has at least 80% sequence identity to the sequence ENVLTQSPAIM-SASLGEKVTMSCRASSSVNYMYWYQQKSDASK-LSWIYYTSNL APGVPARFSGSGSGNSYSLTISSMEGE-DAATYYCQQFTSSPLTFGAGTKLELK (SEQ ID NO:68) and a variable heavy chain sequence comprising a sequence which has at least 80% sequence identity to the sequence

```
                                   (SEQ ID NO: 72)
QVQLKQSGPGLVQPSQSLSITCTVSGFSLTSYGVHWVRQSPGKGLEWLG

VIWSGGSTDYNAAFISRLSISKDNSKSQVFFKMNSLQANDTAIYYCARN

GGNYYFDYWGQGTTLTVSS
```

An antibody or fragment according to the invention comprising the light chain CDR1-3 sequences and heavy chain CDR1-3 sequences specified herein or a variable light chain sequence and variable heavy chain sequence specified herein preferably potentiates FH activity. Said FH activity is preferably inhibition of alternative complement activation. Said inhibition of alternative complement activation comprises an inhibition of hemolytic activity, an inhibition of complement component 3 (C3) deposition, and/or an increase of binding of FH to C3b, iC3b and/or C3d.

In a further aspect, the invention provides an isolated, synthetic or recombinant nucleic acid molecule comprising a nucleic acid sequence encoding the antibody or fragment according to the invention.

In a further aspect, the invention provides a vector comprising a nucleic acid molecule according to the invention.

In a further aspect, the invention provides a recombinant cell comprising a nucleic acid molecule or vector according to the invention.

In a further aspect, the invention provides a pharmaceutical composition comprising an antibody or fragment according to the invention and a pharmaceutically acceptable carrier, diluent and/or excipient.

In a further aspect, the invention provides a pharmaceutical composition comprising a nucleic acid molecule according to the invention and a pharmaceutically acceptable carrier, diluent and/or excipient.

In a further aspect, the invention provides a pharmaceutical composition comprising a vector according to the invention and a pharmaceutically acceptable carrier, diluent and/or excipient.

In a further aspect, the invention provides an antibody or fragment according to the invention for use in therapy.

In a further aspect, the invention provides a nucleic acid molecule according to the invention for use in therapy.

In a further aspect, the invention provides a vector according to the invention for use in therapy.

In a further aspect, the invention provides an antibody or fragment according to the invention for use in inhibiting alternative complement activation.

In a further aspect, the invention provides a nucleic acid molecule according to the invention for use in inhibiting alternative complement activation.

In a further aspect, the invention provides a vector according to the invention for use in inhibiting alternative complement activation.

In a further aspect, the invention provides an antibody or fragment according to the invention for use in the treatment, alleviation or prevention of a disorder associated with alternative pathway complement activation.

In a further aspect, the invention provides a nucleic acid molecule according to the invention for use in the treatment, alleviation or prevention of a disorder associated with alternative pathway complement activation.

In a further aspect, the invention provides a vector according to the invention for use in the treatment, alleviation or prevention of a disorder associated with alternative pathway complement activation.

In a further aspect, the invention provides a use of nucleic acid molecule according to the invention for the preparation of a medicament for the treatment, alleviation or prevention of a disorder associated with alternative pathway complement activation.

In a further aspect, the invention provides a use of a vector according to the invention for the preparation of a medicament for the treatment, alleviation or prevention of a disorder associated with alternative pathway complement activation.

In a further aspect, the invention provides a use of an antibody or fragment according to the invention for the preparation of a medicament for the treatment, alleviation or prevention of a disorder associated with alternative pathway complement activation.

In a further aspect, the invention provides a method for treating, alleviating or preventing a disorder associated with alternative pathway complement activation comprising administering to an individual in need thereof a therapeutically effective amount of an antibody or fragment according to the invention.

In a further aspect, the invention provides a method for treating, alleviating or preventing a disorder associated with alternative pathway complement activation comprising administering to an individual in need thereof a therapeutically effective amount of a nucleic acid molecule according to the invention.

In a further aspect, the invention provides a method for treating, alleviating or preventing a disorder associated with alternative pathway complement activation comprising administering to an individual in need thereof a therapeutically effective amount of a vector according to the invention.

In a further aspect, the invention provides a method for treating, alleviating or preventing a disorder associated with alternative pathway complement activation comprising administering to an individual in need thereof a therapeutically effective amount of a pharmaceutical composition according to the invention.

In a further aspect, the invention provides a method for inhibiting alternative complement activation comprising administering to an individual an antibody or fragment according to the invention.

In a further aspect, the invention provides a method for inhibiting alternative complement activation comprising administering to an individual a nucleic acid molecule according to the invention.

In a further aspect, the invention provides a method for inhibiting alternative complement activation comprising administering to an individual a vector according to the invention.

In a further aspect, the invention provides a method for producing an antibody or fragment according to the invention, the method comprising providing a cell with a nucleic acid molecule or a vector according to the invention, and allowing said cell to translate the nucleic acid sequence comprised by said nucleic acid molecule or vector, thereby producing said antibody or fragment according to the invention.

DETAILED DESCRIPTION

In one aspect, the present invention provides agonistic anti-FH antibodies and fragments thereof, i.e. antibodies and fragments that potentiate FH activity. In one aspect, these antibodies compete with antibody FH.07 for binding to the same epitope in domain CCP18 of FH. Potentiating anti-FH antibodies are potent inhibitors of activation of the alternative complement pathway and therefor useful in the treatment of disorders associated with unwanted or excessive activation of the alternative pathway of the complement system. FH specifically inhibits the amplification loop of the alternative pathway wherein the cleavage of C3 into C3b and subsequent binding thereof to FB at the cell surface and formation of the C3 convertase promotes cleavage of further C3 molecules into C3b. The main advantage of the fact that the antibodies and fragments of the invention interfere with complement activation at the level of C3 is that accumulation of C3b on the surface and release of C3a is avoided. Contrary, if complement activation is inhibited at the C5 level, such as with eculizumab, accumulation of C3b and release of C3a is not inhibited. C3b acts as an opsonin and C3a is an anaphylatoxin. Accumulation of C3b and C3a formation is thus preferably prevented, because these processes result in the attraction of immune cells and opsonophagocytosis of the target. This means that for instance PNH patients receiving eculizumab still need transfusions because accumulation of C3b results in opsonisation of red blood cells, which are subsequently removed in the liver and spleen. Further, treatment with anti-05 antibodies results in accumulation of C3b and C3a formation on cells that would otherwise be lysed by the MAC. An important disadvantage of anti-05 antibodies is that patients become vulnerable for infections because the antibodies interfere with complement activation induced by pathogens as well. By targeting a regulator of the complement system that protects host cells, this is avoided.

The term "antibody" as used herein, refers to an immunoglobulin protein comprising at least a heavy chain variable region (VH), paired with a light chain variable region (VL), that is specific for a target epitope. The term covers both polyclonal and monoclonal antibodies. It refers to any form of antibody that specifically binds to CCP18, preferably to CCP18, of FH, including full length immunoglobulins. An antibody or fragment thereof according to the invention comprises at least one antigen binding site. The term "antigen binding site" as used herein refers to a site of an antibody or fragment thereof comprising at least one CDR sequence, preferably at least two CDR sequences, more preferably at least three CDR sequences. For instance, an antigen binding site comprises light chain CDRs 1-3 or heavy chain CDRs 1-3. A particularly preferred antigen binding site comprises light chain CDRs 1-3 and heavy chain CDRs 1-3.

As is well known by the skilled person, antibodies contain two heavy chains and two light chains. A heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain of the light chain is often, but not always, together with the variable domain of the heavy chain involved in antigen binding. Complementary-determining regions (CDRs) are the hypervariable regions present in heavy chain variable domains and light chain variable domains. In case of full length antibodies, the CDRs 1-3 of a heavy chain and the CDRs 1-3 of the connected light chain together form the antigen-binding site.

An "antigen binding fragment of an antibody" is defined herein as a part of an antibody that is capable of specifically binding the same antigen as the antibody, i.e. CCP18 of FH, although not necessarily to the same extent. A fragment of an FH activity potentiating antibody further also potentiates FH activity, although not necessarily to the same extent. A fragment of an FH activity inhibiting antibody further also inhibits FH activity, although not necessarily to the same extent. An antibody fragment according to the invention of preferably comprises the heavy chain CDR1, CDR2 and CDR3 sequences of an antibody, as well as the light chain CDR1, CDR2 and CDR3 sequence of said antibody. Non-limiting examples of a fragment of an antibody are a single domain antibody, a single chain antibody, a nanobody, an unibody, a single chain variable fragment (scFv), a Fab fragment, a Fab' fragment, a F(ab')2 fragment and a F(ab)$_2$ fragment. A preferred fragment of an antibody comprises at least a heavy chain variable domain (VH) and/or a light chain variable domain (VL). A more preferred fragment comprises at least a Fab fragment. Fab' fragments of potentiating anti-FH antibody FH.07, which competes with the antibodies of the present invention for binding to the same epitope, has been demonstrated to retain the ability to potentiate the function of FH. Particularly preferred fragments of an antibody of the invention are therefore a Fab fragment, a Fab' fragment, a F(ab')2 fragment and a F(ab)$_2$ fragment of antibodies according to the invention. In another embodiment, a fragment of an antibody according to the invention comprises an immunoglobulin heavy chain variable region, an immunoglobulin heavy chain constant region, an immunoglobulin light chain variable region and an immunoglobulin light chain constant region.

As used herein the terms "specific for" and "specifically binds" or "capable of specifically binding" refer to the non-covalent interaction between an antibody and its epitope. It indicates that the antibody or fragment preferentially binds to said epitope over other binding sites or other antigens. Hence, although the antibody or fragment may non-specifically bind to other binding sites or antigens, the binding affinity of said antibody or fragment for its epitope is significantly higher than the binding affinity of said antibody or fragment for any other binding site or antigen.

The percentage of identity of an amino acid sequence or nucleic acid sequence, or the term "% sequence identity", is defined herein as the percentage of residues of the full length of an amino acid sequence or nucleic acid sequence that is identical with the residues in a reference amino acid sequence or nucleic acid sequence after aligning the two sequences and introducing gaps, if necessary, to achieve the maximum percent identity. Methods and computer programs for the alignment are well known in the art, for example "Align 2".

In amino acid sequences as depicted herein amino acids are denoted by single-letter symbols. These single-letter symbols and three-letter symbols are well known to the person skilled in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine.

Preferred antibodies and fragments according to the invention are able to potentiate the activity of FH, preferably of human FH. With the term "potentiating FH activity" is meant that the activity of FH is increased if an antibody or fragment according to the invention binds to FH. The activity of FH that is potentiated by antibodies and fragments of the invention is preferably inhibition of alternative complement activation, preferably in an individual. As used herein the term "alternative complement activation" refers to activation of the complement system via the alternative pathway, i.e. involving at least the formation of the C3 convertase of the alternative pathway, i.e. C3bBb/C3bBbP, or involving an increase in the formation of this C3 convertase. Alternative complement activation may further involve cleavage of C3 into C3a and C3b by the alternative pathway C3 convertase, formation of the alternative pathway C5 convertase, i.e. C3bBbC3b/C3bBbC3b, and/or cleavage of C5 and subsequent binding of C6, C7, C8 and C9 to form the MAC. Alternative complement activation may further include an increase in the alternative pathway amplification loop. Said alternative complement activation is preferably inhibited in an individual, preferably in a bodily fluid of an individual, preferably in blood, interstitial fluid or cerebrospinal fluid, more preferably in blood. As used herein, an "individual" is a human or an animal that comprises a complement system as part of its immune system. Preferably said individual is a mammal, more preferably a human.

As used herein "inhibition of alternative complement activation" comprises any alteration in the amount or activity of a component, factor or activity of the alternative complement system that causes or is the result of inhibition thereof. Inhibition of alternative complement activation for instance comprises an inhibition of hemolytic activity, an inhibition of complement component 3 (C3) deposition on cells of said individual, an increase of binding of FH to C3b, iC3b and/or C3d, an inhibition of the formation of the alternative complement pathway C3 convertase C3bBb/C3bBbP, an inhibition of binding of factor B to C3b and/or inhibition of the interaction between C3b and factor B, an inhibition of the cleavage of C3 into C3a and C3b by the alternative pathway C3 convertase, an increase in the binding of fH to host cells, in particular to sialic acid, glycosaminoglycans and/or heparin expressed on host cells, an inhibition of the amplification loop of the alternative complement pathway, and inhibition of the formation of the alternative complement pathway C5 convertase C3bBbC3bP/C3bBbC3bP, an inhibition of the cleavage of C5 to C5a and C5b by the alternative pathway C5 convertase, an increase in the decay accelerating activity of FH, i.e. promotion of the dissociation of alternative pathway C3 convertases once they have formed, and/or an increase in FI co-factor activity resulting in degradation of C3b. Inhibition of alternative complement activation by FH that is potentiated by the anti-FH antibodies and fragments of the invention preferably comprises an inhibition of hemolytic activity, an inhibition of C3 deposition on cells of said individual, and/or an increase of binding of FH to C3b, iC3b and/or C3d.

"Inhibition" as used herein preferably means that the indicated activity is reduced by at least about 25%, more preferably at least about 50%, more preferably at least about 75%, more preferably at least about 80%, more preferably at least about 85%, more preferably at least about 90%, most preferably at least about 95%. Thus, "inhibition of alternative complement activation" preferably means that the activity of the alternative complement pathway is reduced by at least about 25%, more preferably at least about 50%, 75%, 80%, 85%, 90% or 95%. Similarly, "an inhibition of hemolytic activity" preferably means that hemolytic activity is reduced by at least about 25%, more preferably at least about 50%, 75%, 80%, 85%, 90% or 95%.

"Increase" as used herein preferably means that the indicated activity is increased by at least about 25%, more preferably at least about 50%, more preferably at least about 75%, more preferably at least about 80%, more preferably at least about 85%, more preferably at least about 90%, most preferably at least about 95%. Thus, "an increase of binding of FH to C3b" preferably means that the binding of FH to C3b is increased by at least about 25%, more preferably at least about 50%, 75%, 80%, 85%, 90% or 95%. Similarly, "an increase in binding of FH to host cells" preferably means that binding of FH to host cells is increased by at least about 25%, more preferably at least about 50%, 75%, 80%, 85%, 90% or 95%.

As used herein "hemolytic activity" refers to the rupture of red blood cells and the subsequent release of the cell's content into e.g. the circulation induced by activation of the complement system, preferably as a result of the formation of MAC at the cell surface. Hemolytic activity is for instance measured as described herein in the Examples by using a hemolytic assay as described by Sanchez-Corral et al. (2004) and Wouters et al. (2008), optionally with some modifications. In this assay, red blood cells such as sheep red blood cells (SRBCs) are incubated with serum, e.g. human serum, e.g. at 37° C. for 1.25 hours while shaking. Sera with low levels of FH or dysfunctional FH lead to lysis of the SRBCsLysis can stopped by addition of veronal buffer containing 20 mM EDTA followed by centrifugation in a pre-chilled centrifuge (e.g. 7° C.) for 2.5 minutes. The percentage of red blood cell lysis is determined by measuring the absorbance of the supernatants at 412 nm. The serum can for instance be from healthy human individuals or from human individuals suffering from a disorder associated with unwanted or excessive alternative pathway complement activation, such as aHUS. The ability of an antibody or fragment to inhibit hemolytic activity can be determined by incubating the red blood cells with serum in the presence of the antibody or fragment.

Inhibition of C3 deposition is for instance measured using a C3 deposition assay as described herein in the Examples. This assay involves the coating of microtiterplates with LPS. The plates are subsequently incubated with serum, e.g. from healthy individuals or from individuals suffering from a disorder associated with unwanted or excessive alternative complement activation as indicated above, in the presence or absence of antibody or fragments. C3 deposition on LPS can be detected with an anti-C3 antibody.

An increase of binding of FH to C3b is for instance measured using a ELISA as described herein in the Examples. This assay involves coating of microtiter ELISA plate with C3b and incubation of the plate with serum, e.g. from healthy individuals or from individuals suffering from a disorder associated with unwanted or excessive alternative complement activation as indicated above. Bound FH can be detected with an anti-FH antibody, such as peroxidase-labeled polyclonal anti-FH. The ability of an antibody or fragment to enhance FH binding to C3b can be determined by preincubating the serum in the presence of the antibody or fragment before incubation with the coated C3b. As another example, binding of FH to C3b can be determined using Surface Plasmon Resonance (SPR) for instance as described herein in the Examples. SPR is a technique to measure biomolecular interactions in real-time in a label free environment. One of the interactants, for instance C3b, is immobilized to a sensor surface, and the other, for instance FH, is free in solution and passed over the surface, e.g. in the presence or absence of (different concentrations of) an antibody or fragment of the invention. Preferred antibodies or fragments thereof according to the present invention increase binding affinity ($K_D$) of FH for C3b in vitro to at most 2 µM, more preferably at most 1.95 µM, more preferably at most 1.8 µM, more preferably at most 1.7 µM and/or increases binding affinity of FH for C3b in vitro at least 3 times, more preferably at least 3.1 times, more preferably at least 3.2 times, more preferably at least 3.3 times, more preferably at least 3.5 times, more preferably at least 3.6 times.

Preferred antibodies or fragments thereof provided by the present invention have a low in vitro $IC_{50}$ value in one or more functional assay's, more preferably an in vitro $IC_{50}$ value that is lower than the in vitro $IC_{50}$ value of antibody FH.07 for the same functional assay. "$IC_{50}$" is a term well known in the art and refers to the concentration of an antibody or fragment that is necessary to inhibit or reduce a certain functional activity by 50%. The lower the $IC_{50}$ value of an antibody or fragment, the stronger the inhibiting activity of the antibody or fragment, and the greater its potential as a therapeutic agent. Said functional assay preferably is a C3b deposition assay and/or a hemolytic assay as described herein above. In a preferred aspect, an antibody or fragment thereof according to the invention inhibits C3 deposition on LPS in vitro with an $IC_{50}$ value of 38 nM or less, more preferably 35 nM or less, more preferably 32 nM or less, more preferably 30 nM or less, more preferably 28 nM or less, more preferably 27 nM or less. In a further preferred aspect, an antibody or fragment thereof according to the invention inhibits hemolytic activity in vitro with an $IC_{50}$ value of 150 nM or less, more preferably 130 nM or less, more preferably 115 nM or less, more preferably 105 nM or less, more preferably 100 nM or less, more preferably 95 nM or less.

Further preferred antibodies or fragment of the invention inhibit C3 deposition on LPS in vitro with a low $IC_{50}$ value as described herein above and inhibit hemolytic activity in vitro with a low $IC_{50}$ value as described herein above. Hence, a preferred antibody or fragment according to the invention inhibits C3 deposition on LPS in vitro with an $IC_{50}$ value of 38 nM or less and inhibits hemolytic activity in vitro with an $IC_{50}$ value of 150 nM or less, more preferably inhibits C3 deposition on LPS in vitro with an $IC_{50}$ value of 30 nM or less and inhibits hemolytic activity in vitro with an $IC_{50}$ value of 150 nM or less, more preferably inhibits C3 deposition on LPS in vitro with an $IC_{50}$ value of 27 nM or less and inhibits hemolytic activity in vitro with an $IC_{50}$ value of 100 nM or less. The $IC_{50}$ value for C3 deposition on LPS in vitro is preferably determined in a C3 deposition assay as described herein above. The $IC_{50}$ value for hemolytic activity is preferably determined in a hemolytic activity assay as described herein above.

"Binding affinity" refers to the strength of the total sum of the noncovalent interactions between a single binding site of an antibody or functional part or functional equivalent and its binding partner (e.g., an antigen). Unless indicated otherwise, as used herein, "binding affinity" refers to intrinsic binding affinity which reflects a 1:1 interaction between members of a binding pair (antibody and antigen in the present application). Binding affinity is herein represented by the equilibrium dissociation constant ($K_D$), which is calculated as the $k_a$ to $k_d$ ratio, see, e.g., Chen, Y., et al., 1999. Affinity can be measured by common methods known in the art, such as for instance a surface plasmon resonance (SPR) assay such as BiaCore (GE Healthcare Life Sciences GE Healthcare Life Sciences) or IBIS-iSPR instrument at IBIS Technologies BV (Hengelo, the Netherlands) or solution phase assays, such as Kinexa.

Preferred antibodies or fragments thereof provided by the present invention have a high binding affinity for FH and/or a FH fragment comprising domains CCP18-20, more preferably a binding affinity that is higher than the binding affinity of antibody FH.07. In vivo therapeutic activity of an antibody or fragment typically requires high binding affinity, e.g. to minimize binding of the antibody or fragment to binding sites and/or antigens other than the epitope or antigen it is specific for and to minimize the amount of antibody or fragment that needs to be administered in vivo. Hence, antibodies with a high binding affinity are preferred. An antibody or fragment thereof preferably has a binding affinity for FH with a dissociation constant ($K_D$) of $2.5 \times 10^{-8}$ M or less and/or a binding affinity for a FH fragment comprised of CCP18-20 with a $K_D$ of $0.1 \times 10^{-9}$ M or less. In one embodiment, the invention therefore provides an isolated, synthetic or recombinant antibody or antigen binding fragment thereof that specifically binds to factor H (FH) and potentiates FH activity, wherein the antibody has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less. Preferably an antibody or fragment according to the invention has a binding affinity for FH with a $K_D$ of $2.25 \times 10^{-8}$ M or less, more preferably $2 \times 10^{-8}$ M or less, more preferably $1.75 \times 10^{-8}$ M or less, more preferably $1.5 \times 10^{-8}$ M or less, more preferably $1.25 \times$ $10^{-8}$ M or less, more preferably $1\times10^{-8}$ M or less, more preferably $0.9\times10^{-8}$ M or less, more preferably $0.8\times10^{-8}$ M or less, more preferably $0.7\times10^{-8}$ M or less, more preferably $0.6\times10^{-8}$ M or less, and/or a binding affinity for a FH fragment comprised of CCP18-20 with a $K_D$ of $0.09\times10^{-9}$M or less, more preferably $0.08\times10^{-9}$ M or less, more preferably $0.07\times10^{-9}$ M or less, more preferably $0.06\times10^{-9}$M or less, more preferably $0.05\times10^{-9}$ M or less, more preferably $0.04\times10^{-9}$ M or less, more preferably $0.03\times10^{-9}$ M or less, more preferably $0.02\times10^{-9}$ M, or less more preferably $1\times10^{-11}$ M or less, more preferably $0.9\times10^{-11}$ M or less, more preferably $0.8\times10^{-11}$ M or less, more preferably $0.7\times10^{-11}$ M or less, more preferably $0.6\times10^{-11}$ M or less. In a preferred aspect, an antibody or fragment thereof preferably has a binding affinity for FH with a $K_D$ of $1.25\times10^{-8}$ M or less and/or a binding affinity for a FH fragment comprised of CCP18-20 with a $K_D$ of $0.04\times10^{-9}$ M or less. In a further preferred aspect, an antibody or fragment thereof preferably has a binding affinity for FH with a $K_D$ of $0.6\times10^{-8}$ M or less and/or a binding affinity for a FH fragment comprised of CCP18-20 with a $K_D$ of $0.6\times10^{-11}$M or less. Said binding affinity is preferably determined using surface plasmon resonance (SPR), more preferably using SPR in an assay as described herein, i.e. in an assay wherein binding affinity is determined by SPR on a ProtA chip, capturing the antibody or fragment before flowing either full length FH (for binding affinity for FH) or a fragment of FH comprised of domain 18-20 (for binding affinity for CCP18-20) over the surface.

Further preferred antibodies or fragments according to the invention have a high binding affinity and inhibit C3 deposition on LPS in vitro with a low $IC_{50}$ value and/or inhibit hemolytic activity in vitro with a low $IC_{50}$ value. Hence, a preferred antibody or fragment according to the invention has a binding affinity for FH with a $K_D$ of $2.5\times10^{-8}$ M or less and/or a binding affinity for a FH fragment comprised of CCP18-20 with a $K_D$ of $0.1\times10^{-9}$ M or less and inhibits C3 deposition on LPS in vitro with an $IC_{50}$ value of 38 nM or less and/or inhibits hemolytic activity in vitro with an $IC_{50}$ value of 150 nM or less. More preferably the antibody or fragment has a binding affinity for FH with a $K_D$ of $1.25\times10^{-8}$ M or less and/or a binding affinity for a FH fragment comprised of CCP18-20 with a $K_D$ of $0.04\times10^{-9}$ M or less and inhibits C3 deposition on LPS in vitro with an $IC_{50}$ value of 30 nM or less and inhibits hemolytic activity in vitro with an $IC_{50}$ value of 115 nM or less. Even more preferably the antibody or fragment has a binding affinity for FH with a $K_D$ of $1.25\times10^{-8}$ M or less and/or a binding affinity for a FH fragment comprised of CCP18-20 with a $K_D$ of $0.04\times10^{-9}$ M or less and inhibits C3 deposition on LPS in vitro with an $IC_{50}$ value of 27 nM or less and inhibits hemolytic activity in vitro with an $IC_{50}$ value of 100 nM or less. Said binding affinity, is preferably determined by SPR as described herein. The $IC_{50}$ value for C3 deposition on LPS in vitro is preferably determined in a C3 deposition assay as described herein above. The $IC_{50}$ value for hemolytic activity is preferably determined in a hemolytic activity assay as described herein above.

A particularly preferred antibody according to the invention is antibody anti-FHR-1.8E4, the preparation and identification of which is described in the Examples. Table 1 provides an overview of the variable heavy and light chain sequences, as well as the individual CDR sequences, of antibody anti-FHR-1.8E4. Even more preferred are monoclonal chimeric or humanized antibodies or fragments thereof comprising the heavy chain CDR sequences and light chain CDR sequences of antibody anti-FHR-1.8E4 or the heavy chain variable region and the light chain variable region of antibody anti-FHR-1.8E4. The term "anti-FHR-1.8E4" as used herein encompass all antibodies and fragments having at least the heavy chain and light chain CDR1, CDR2 and CDR3 region as depicted in Table 1, such as for instance isolated and/or purified antibodies or recombinantly produced antibodies. Antibody anti-FHR-1.8E4 competes for binding to the same epitope in CCP18 of FH as antibody FH.07. Antibody anti-FHR-1.8E4 has a low $IC_{50}$ value for inhibition of C3 deposition on LPS in vitro of 26.3 nM and a low $IC_{50}$ value for inhibition of hemolytic activity in vitro of 94.0 nM. Antibody anti-FHR-1.8E4 further has a high binding affinity for full length FH with a $K_D$ of $1.04\times10^{-8}$ and a high binding affinity for a fragment of FH comprised of CCP18-20 with a $K_D$ of $3.13\times10^{-11}$. Antibody anti-FHR-1.8E4 further increases binding affinity ($K_D$) of FH for C3b in vitro from 6 µM to 1.66 µM, i.e. 3.6 times.

A further particularly preferred antibody according to the invention is antibody anti-FHR-1.3B4, the preparation and identification of which is described in the Examples. Table 1 provides an overview of the variable heavy and light chain sequences, as well as the individual CDR sequences, of antibody anti-FHR-1.3B4. Even more preferred are monoclonal chimeric or humanized antibodies or fragments thereof comprising the heavy chain CDR sequences and light chain CDR sequences of antibody anti-FHR-1.3B4 or the heavy chain variable region and the light chain variable region of antibody anti-FHR-1.3B4. The term "anti-FHR-1.3B4" as used herein encompass all antibodies and fragments having at least the heavy chain and light chain CDR1, CDR2 and CDR3 region as depicted in Table 1, such as for instance isolated and/or purified antibodies or recombinantly produced antibodies. Antibody anti-FHR-1.3B4 competes for binding to the same epitope in CCP18 of FH as antibody FH.07. Antibody anti-FHR-1.3B4 has a low $IC_{50}$ value for inhibition of C3 deposition on LPS in vitro of 38.41 nM and a low $IC_{50}$ value for inhibition of hemolytic activity in vitro of 127.5 nM. Antibody anti-FHR-1.3B4 further has a high binding affinity for full length FH with a $K_D$ of $0.58\times10^{-8}$ and a high binding affinity for a fragment of FH comprised of CCP18-20 with a $K_D$ of $5.44\times10^{-12}$. Antibody anti-FHR-1.3B4 further increases binding affinity ($K_D$) of FH for C3b in vitro from 6 µM to 1.9 µM, i.e. 3.2 times.

A further particularly preferred antibody according to the invention is antibody anti-FHR-1.11E1, the preparation and identification of which is described in the Examples. Table 1 provides an overview of the variable heavy and light chain sequences, as well as the individual CDR sequences, of antibody anti-FHR-1.11E1. Even more preferred are monoclonal chimeric or humanized antibodies or fragments thereof comprising the heavy chain CDR sequences and light chain CDR sequences of antibody anti-FHR-1.11E1 or the heavy chain variable region and the light chain variable region of antibody anti-FHR-1.11E1. The term "anti-FHR-1.11E1" as used herein encompass all antibodies and fragments having at least the heavy chain and light chain CDR1, CDR2 and CDR3 region as depicted in Table 1, such as for instance isolated and/or purified antibodies or recombinantly produced antibodies. Antibody anti-FHR-1.11E1 competes for binding to the same epitope in CCP18 of FH as antibody FH.07. Antibody anti-FHR-1.11E1 has a low $IC_{50}$ value for inhibition of C3 deposition on LPS in vitro of 25.04 nM.

A further particularly preferred antibody according to the invention is antibody anti-FHR-1.12F4, the preparation and identification of which is described in the Examples. Table 1 provides an overview of the variable heavy and light chain sequences, as well as the individual CDR sequences, of antibody anti-FHR-1.12F4. Even more preferred are monoclonal chimeric or humanized antibodies or fragments thereof comprising the heavy chain CDR sequences and light chain CDR sequences of antibody anti-FHR-1.12F4 or the heavy chain variable region and the light chain variable region of antibody anti-FHR-1.12F4. The term "anti-FHR-1.12F4" as used herein encompass all antibodies and fragments having at least the heavy chain and light chain CDR1, CDR2 and CDR3 region as depicted in Table 1, such as for instance isolated and/or purified antibodies or recombinantly produced antibodies. Antibody anti-FHR-1.12F4 competes for binding to the same epitope in CCP18 of FH as antibody FH.07. Antibody anti-FHR-1.12F4 has a low $IC_{50}$ value for inhibition of C3 deposition on LPS in vitro of 345.2 nM.

Provided is therefore an isolated, synthetic or recombinant antibody or antigen binding fragment thereof that specifically binds to complement control protein domain 18 (CCP18) of factor H (FH) comprising:
 a light chain CDR1 sequence having the sequence SSVXY, wherein X is R, T or N (SEQ ID NO:91) or the sequence QSLVHSNGNTY (SEQ ID NO:49),
 a light chain CDR2 sequence having the sequence $X_1X_2S$ wherein $X_1$=A, K or Y and $X_2$=T or L (SEQ ID NO:92),
 a light chain CDR3 having a sequence selected from the group consisting of

QQWGTKPPT,     (SEQ ID NO: 19)

QQRSSSNPLT,     (SEQ ID NO: 35)

SQSTHVPFT     (SEQ ID NO: 51)
and

QQFTSSPLT,     (SEQ ID NO: 67)

a heavy chain CDR1 having the sequence $X_1FSLTX_2X_3G$, wherein $X_1$=D or G, $X_2$=N or S and $X_3$=S or Y (SEQ ID NO:93),
 a heavy chain CDR2 having the sequence IWSGGXT, wherein x=T, N or S (SEQ ID NO:94), and
 a heavy chain CDR3 sequence having the sequence $ARNX_1GNYX_2X_3DY$, wherein $X_1$=F or G, $X_2$=A or Y and $X_3$=V, M or F (SEQ ID NO:95) or AKNGDYGYTMDY (SEQ ID NO:55).
In a preferred embodiment, said antibody comprises:
 a light chain CDR1 sequence having the sequence SSVXY, wherein X is R or T (SEQ ID NO:96),
 a light chain CDR2 sequence having the sequence ATS (SEQ ID NO:97),
 a light chain CDR3 having a sequence selected from the group consisting of QQWGTKPPT (SEQ ID NO:19) and QQRSSSNPLT (SEQ ID NO:35),
 a heavy chain CDR1 having the sequence $X_1FSLTNX_2G$, wherein $X_1$=D or G and $X_2$=S or Y (SEQ ID NO:98),
 a heavy chain CDR2 having the sequence IWSGGTT (SEQ ID NO:99), and
 a heavy chain CDR3 sequence having the sequence ARNFGNYAXDY, wherein X=V or M (SEQ ID NO:100).
Said antibody or fragment preferably potentiates FH activity, preferably inhibition of alternative complement activation, such as inhibition of hemolytic activity, inhibition of complement component 3 (C3) deposition, and/or an increase of binding of FH to C3b, iC3b and/or C3d. Said fragment preferably comprises at least a heavy chain variable domain (VH) and/or a light chain variable domain (VL). A more preferred fragment comprises at least a Fab fragment.

Said antibody or fragment preferably has a binding affinity for FH with a $K_D$ of $2.5 \times 10^{-8}$ M or less and/or a binding affinity for a FH fragment comprised of CCP18-20 with a $K_D$ of $0.1 \times 10^{-9}$ M or less, preferably wherein said antibody or fragment has a binding affinity for FH with a $K_D$ of $1.25 \times 10^{-8}$ M or less and/or a binding affinity for a FH fragment comprised of CCP18-20 with a $K_D$ of $0.04 \times 10^{-9}$ M or less.

In a further preferred embodiment, the invention provides an isolated, synthetic or recombinant antibody or antigen binding fragment thereof that specifically binds to CCP18 of FH comprising a light chain CDR1 sequence having the sequence SSVRY (SEQ ID NO:17), a light chain CDR2 sequence having the sequence ATS (SEQ ID NO:18) and a light chain CDR3 having the sequence QQWGTKPPT (SEQ ID NO:19), a heavy chain CDR1 having the sequence DFSLTNSG (SEQ ID NO:21), a heavy chain CDR2 having the sequence IWSGGTT (SEQ ID NO:22), and a heavy chain CDR3 sequence having the sequence ARNFGNYAVDY (SEQ ID NO:23). In one embodiment, said antibody comprises a variable light chain sequence comprising a sequence which has at least 80% sequence identity to the sequence QIVLSQSPAILSASPGEKVTMT-CRASSSVRYMHWYQQKAGSSPTAWIFATSNLA SGVPPRFSGSGSGTSYSLTISRVEAE-DAATYYCQQWGTKPPTFGAGTKLELK (SEQ ID NO:20) and a variable heavy chain sequence comprising a sequence which has at least 80% sequence identity to the sequence QVQLKQSGPGLVQPSQSL-SITCTVSDFSLTNSGVHWVRQSPGKGLEWLGVIWS GGTTEYNAAFMSRLTITKDNSKSQVFFKMNSLL-VDDTGIYYCARNFGNYAVDY WGQGTSVTVSS (SEQ ID NO:24). In a further embodiment, said antibody or fragment comprises a variable light chain sequence comprising a sequence which has at least 85%, more preferably at least 90%, more preferably at least 95%, more preferably at least 96%, more preferably at least 97%, more preferably at least 98%, more preferably at least 99% sequence identity with said sequence of SEQ ID NO: 20 and a variable heavy chain sequence comprising a sequence which has at least 85%%, more preferably at least 90%, more preferably at least 95%, more preferably at least 96%, more preferably at least 97%, more preferably at least 98%, more preferably at least 99% sequence identity with said sequence of SEQ ID NO: 24. In a particular embodiment said antibody or fragment comprises a variable light chain sequence comprising the sequence of SEQ ID NO: 20 and a variable light chain sequence comprising the sequence of SEQ ID NO: 24. Said antibody or fragment preferably potentiates FH activity, preferably inhibition of alternative complement activation, such as inhibition of hemolytic activity, inhibition of complement component 3 (C3) deposition, and/or an increase of binding of FH to C3b, iC3b and/or C3d. Said fragment preferably comprises at least a heavy chain variable domain (VH) and/or a light chain variable domain (VL). A more preferred fragment comprises at least a Fab fragment.

Said antibody or fragment comprising a light chain CDR1 sequence having the sequence SSVRY (SEQ ID NO:17), a light chain CDR2 sequence having the sequence ATS (SEQ ID NO:18) and a light chain CDR3 having the sequence QQWGTKPPT (SEQ ID NO:19), a heavy chain CDR1 having the sequence DFSLTNSG (SEQ ID NO:21), a heavy chain CDR2 having the sequence IWSGGTT (SEQ ID NO:22), and a heavy chain CDR3 sequence having the sequence ARNFGNYAVDY (SEQ ID NO:23) preferably has a binding affinity for FH with a $K_D$ of $2.5 \times 10^{-8}$ M or less and/or a binding affinity for a FH fragment comprised of CCP18-20 with a $K_D$ of $0.1 \times 10^{-9}$M or less. Preferably said antibody or fragment has a binding affinity for FH with a $K_D$ of $2.25 \times 10^{-8}$ M or less, more preferably $2 \times 10^{-8}$ M or less, more preferably $1.75 \times 10^{-8}$ M or less, more preferably $1.5 \times 10^{-8}$ M or less, more preferably $1.25 \times 10^{-8}$ M or less, and/or a binding affinity for a FH fragment comprised of CCP18-20 with a $K_D$ of $0.09 \times 10^{-9}$ M or less, more preferably $0.08 \times 10^{-9}$M or less, more preferably $0.07 \times 10^{-9}$M or less, more preferably $0.06 \times 10^{-9}$ M or less, more preferably $0.05 \times 10^{-9}$ M or less, more preferably $0.04 \times 10^{-9}$M or less.

Said antibody or fragment comprising a light chain CDR1 sequence having the sequence SSVRY (SEQ ID NO:17), a light chain CDR2 sequence having the sequence ATS (SEQ ID NO:18) and a light chain CDR3 having the sequence QQWGTKPPT (SEQ ID NO:19), a heavy chain CDR1 having the sequence DFSLTNSG (SEQ ID NO:21), a heavy chain CDR2 having the sequence IWSGGTT (SEQ ID NO:22), and a heavy chain CDR3 sequence having the sequence ARNFGNYAVDY (SEQ ID NO:23) preferably inhibits C3 deposition on LPS in vitro with an $IC_{50}$ value of 38 nM or less. Preferably said antibody or fragment inhibits C3 deposition on LPS in vitro with an $IC_{50}$ value of 35 nM or less, more preferably 32 nM or less, more preferably 30 nM or less, more preferably 28 nM or less, more preferably 27 nM or less.

Said antibody or fragment comprising a light chain CDR1 sequence having the sequence SSVRY (SEQ ID NO:17), a light chain CDR2 sequence having the sequence ATS (SEQ ID NO:18) and a light chain CDR3 having the sequence QQWGTKPPT (SEQ ID NO:19), a heavy chain CDR1 having the sequence DFSLTNSG (SEQ ID NO:21), a heavy chain CDR2 having the sequence IWSGGTT (SEQ ID NO:22), and a heavy chain CDR3 sequence having the sequence ARNFGNYAVDY (SEQ ID NO:23) preferably inhibits hemolytic activity in vitro with an $IC_{50}$ value of 150 nM or less. Preferably said antibody or fragment inhibits hemolytic activity in vitro with an $IC_{50}$ value of 115 nM or less, more preferably 105 nM or less.

Said antibody or fragment comprising a light chain CDR1 sequence having the sequence SSVRY (SEQ ID NO:17), a light chain CDR2 sequence having the sequence ATS (SEQ ID NO:18) and a light chain CDR3 having the sequence QQWGTKPPT (SEQ ID NO:19), a heavy chain CDR1 having the sequence DFSLTNSG (SEQ ID NO:21), a heavy chain CDR2 having the sequence IWSGGTT (SEQ ID NO:22), and a heavy chain CDR3 sequence having the sequence ARNFGNYAVDY (SEQ ID NO:23) preferably increases binding affinity ($K_D$) of FH for C3b in vitro to at most 2 μM, more preferably 1.8 μM and/or increases binding affinity of FH for C3b in vitro at least 3 times, more preferably 3.5 times.

In a further preferred embodiment, the invention provides an isolated, synthetic or recombinant antibody or antigen binding fragment thereof that specifically binds to CCP18 of FH comprising a light chain CDR1 sequence having the sequence SSVTY (SEQ ID NO:33), a light chain CDR2 sequence having the sequence ATS (SEQ ID NO:34) and a light chain CDR3 having the sequence QQRSSSNPLT (SEQ ID NO:35), a heavy chain CDR1 having the sequence GFSLTNYG (SEQ ID NO:37), a heavy chain CDR2 having the sequence IWSGGTT (SEQ ID NO:38), and a heavy chain CDR3 sequence having the sequence ARNFGNYAMDY (SEQ ID NO:39). In one embodiment, said antibody comprises a variable light chain sequence comprising a sequence which has at least 80% sequence identity to the sequence QIVLSQSPTILSASPGEKVTMT-CRASSSVTYMHWYQQKPGSSPKPWIYATSNLAS GVPARFSGSGSGTSYSLTISRVEAE-DAATYYCQQRSSSNPLTFGAGTKLELK (SEQ ID NO:36) and a variable heavy chain sequence comprising a sequence which has at least 80% sequence identity to the sequence QVQLRQSGPGLVQPSQSL-SITCTVSGFSLTNYGVYWVRQSPGKGLEWLGVIWSG GTTDYSAAFISRLSISKDNSKSQVFFKMNSLQADD-TAIYYCARNFGNYAMDYWG QGTSVTVSS (SEQ ID NO:40). In a further embodiment, said antibody or fragment comprises a variable light chain sequence comprising a sequence which has at least 85%, more preferably at least 90%, more preferably at least 95%, more preferably at least 96%, more preferably at least 97%, more preferably at least 98%, more preferably at least 99% sequence identity with said sequence of SEQ ID NO: 36 and a variable heavy chain sequence comprising a sequence which has at least 85%%, more preferably at least 90%, more preferably at least 95%, more preferably at least 96%, more preferably at least 97%, more preferably at least 98%, more preferably at least 99% sequence identity with said sequence of SEQ ID NO: 40. In a particular embodiment said antibody or fragment comprises a variable light chain sequence comprising the sequence of SEQ ID NO: 36 and a variable light chain sequence comprising the sequence of SEQ ID NO: 40. Said antibody or fragment preferably potentiates FH activity, preferably inhibition of alternative complement activation, such as inhibition of hemolytic activity, inhibition of complement component 3 (C3) deposition, and/or an increase of binding of FH to C3b, iC3b and/or C3d. Said fragment preferably comprises at least a heavy chain variable domain (VH) and/or a light chain variable domain (VL). A more preferred fragment comprises at least a Fab fragment.

Said antibody or fragment comprising a light chain CDR1 sequence having the sequence SSVTY (SEQ ID NO:33), a light chain CDR2 sequence having the sequence ATS (SEQ ID NO:34) and a light chain CDR3 having the sequence QQRSSSNPLT (SEQ ID NO:35), a heavy chain CDR1 having the sequence GFSLTNYG (SEQ ID NO:37), a heavy chain CDR2 having the sequence IWSGGTT (SEQ ID NO:38), and a heavy chain CDR3 sequence having the sequence ARNFGNYAMDY (SEQ ID NO:39) preferably has a binding affinity for FH with a $K_D$ of $2.5 \times 10^{-8}$ M or less and/or a binding affinity for a FH fragment comprised of CCP18-20 with a $K_D$ of $0.1 \times 10^{-9}$M or less. Preferably said antibody or fragment has a binding affinity for FH with a $K_D$ of $2.25 \times 10^{-8}$ M or less, more preferably $2 \times 10^{-8}$ M or less, more preferably $1.75 \times 10^{-8}$ M or less, more preferably $1.5 \times 10^{-8}$ M or less, more preferably $1.25 \times 10^{-8}$ M or less, more preferably $1 \times 10^{-8}$ M or less, more preferably $0.9 \times 10^{-8}$ M or less, more preferably $0.8 \times 10^{-8}$ M or less, more preferably $0.7 \times 10^{-8}$ M or less, more preferably $0.6 \times 10^{-8}$ M or less, and/or a binding affinity for a FH fragment comprised of CCP18-20 with a $K_D$ of $0.09 \times 10^{-9}$ M or less, more preferably $0.08 \times 10^{-9}$ M or less, more preferably $0.07 \times 10^{-9}$ M or less, more preferably $0.06 \times 10^{-9}$M or less, more preferably $0.05 \times 10^{-9}$ M or less, more preferably $0.04 \times 10^{-9}$ M or less, more preferably $0.03 \times 10^{-9}$ M or less, more preferably $0.02 \times 10^{-9}$ M, or less more preferably $1 \times 10^{-11}$M or less, more preferably $0.9 \times 10^{-11}$ M or less, more preferably $0.8 \times 10^{-11}$ M or less, more preferably $0.7 \times 10^{-11}$ M or less, more preferably $0.6 \times 10^{-11}$ M or less.

Said antibody or fragment comprising a light chain CDR1 sequence having the sequence SSVTY (SEQ ID NO:33), a light chain CDR2 sequence having the sequence ATS (SEQ ID NO:34) and a light chain CDR3 having the sequence QQRSSSNPLT (SEQ ID NO:35), a heavy chain CDR1 having the sequence GFSLTNYG (SEQ ID NO:37), a heavy chain CDR2 having the sequence IWSGGTT (SEQ ID NO:38), and a heavy chain CDR3 sequence having the sequence ARNFGNYAMDY (SEQ ID NO:39) preferably inhibits hemolytic activity in vitro with an $IC_{50}$ value of 150 nM or less. Preferably said antibody or fragment inhibits hemolytic activity in vitro with an $IC_{50}$ value of 105 nM or less.

Said antibody or fragment comprising a light chain CDR1 sequence having the sequence SSVTY (SEQ ID NO:33), a light chain CDR2 sequence having the sequence ATS (SEQ ID NO:34) and a light chain CDR3 having the sequence QQRSSSNPLT (SEQ ID NO:35), a heavy chain CDR1 having the sequence GFSLTNYG (SEQ ID NO:37), a heavy chain CDR2 having the sequence IWSGGTT (SEQ ID NO:38), and a heavy chain CDR3 sequence having the sequence ARNFGNYAMDY (SEQ ID NO:39) preferably increases binding affinity ($K_D$) of FH for C3b in vitro to at most 2 µM, more preferably 1.95 µM and/or increases binding affinity of FH for C3b in vitro at least 3 times, more preferably 3.1 times.

In a further preferred embodiment, the invention provides an isolated, synthetic or recombinant antibody or antigen binding fragment thereof that specifically binds to CCP18 of FH comprising a light chain CDR1 sequence having the sequence QSLVHSNGNTY (SEQ ID NO:49), a light chain CDR2 sequence having the sequence KLS (SEQ ID NO:50) and a light chain CDR3 having the sequence SQSTHVPFT (SEQ ID NO:51), a heavy chain CDR1 having the sequence GFSLTNYG (SEQ ID NO:53), a heavy chain CDR2 having the sequence IWSGGNT (SEQ ID NO:54), and a heavy chain CDR3 sequence having the sequence AKNGDYGYTMDY (SEQ ID NO:55). In one embodiment, said antibody comprises a variable light chain sequence comprising a sequence which has at least 80% sequence identity to the sequence DVVMTQTPLSLPVSLGDQASIS-CRSSQSLVHSNGNTYLHWYLQKPGQSPKLLIY KLSNRFSGVPDRFSGSGSGTDFTLKISRVEAE-DLGVYFCSQSTHVPFTFGSGTKL EIK (SEQ ID NO:52) and a variable heavy chain sequence comprising a sequence which has at least 80% sequence identity to the sequence QVQLKQSGPGLVQPSQSL-SITCTVSGFSLTNYGVHWVRQPPGKGLEWLGVIWS GGNTDYNAAFISRLSISKDNSKSQVFFKMNSLQADD-TAIYYCAKNGDYGYTMD YWGQGTSVTVSS (SEQ ID NO:56). In a further embodiment, said antibody or fragment comprises a variable light chain sequence comprising a sequence which has at least 85%, more preferably at least 90%, more preferably at least 95%, more preferably at least 96%, more preferably at least 97%, more preferably at least 98%, more preferably at least 99% sequence identity with said sequence of SEQ ID NO: 52 and a variable heavy chain sequence comprising a sequence which has at least 85%%, more preferably at least 90%, more preferably at least 95%, more preferably at least 96%, more preferably at least 97%, more preferably at least 98%, more preferably at least 99% sequence identity with said sequence of SEQ ID NO: 56. In a particular embodiment said antibody or fragment comprises a variable light chain sequence comprising the sequence of SEQ ID NO: 52 and a variable light chain sequence comprising the sequence of SEQ ID NO: 56. Said antibody or fragment preferably potentiates FH activity, preferably inhibition of alternative complement activation, such as inhibition of hemolytic activity, inhibition of complement component 3 (C3) deposition, and/or an increase of binding of FH to C3b, iC3b and/or C3d. Said fragment preferably comprises at least a heavy chain variable domain (VH) and/or a light chain variable domain (VL). A more preferred fragment comprises at least a Fab fragment.

In a further preferred embodiment, the invention provides an isolated, synthetic or recombinant antibody or antigen binding fragment thereof that specifically binds to CCP18 of FH comprising a light chain CDR1 sequence having the sequence SSVNY (SEQ ID NO:65), a light chain CDR2 sequence having the sequence Yr S (SEQ ID NO:66) and a light chain CDR3 having the sequence of QQFTSSPLT (SEQ ID NO:67), a heavy chain CDR1 having the sequence GFSLTSYG (SEQ ID NO:69), a heavy chain CDR2 having the sequence IWSGGGST (SEQ ID NO:70), and a heavy chain CDR3 sequence having the sequence ARNGG-NYYFDY (SEQ ID NO:71). In one embodiment, said antibody comprises a variable light chain sequence comprising a sequence which has at least 80% sequence identity to the sequence ENVLTQSPAIM-SASLGEKVTMSCRASSSVNYMYWYQQKSDASK-LSWIYYTSNL APGVPARFSGSGSGNSYSLTISSMEGE-DAATYYCQQFTSSPLTFGAGTKLELK (SEQ ID NO:68) and a variable heavy chain sequence comprising a sequence which has at least 80% sequence identity to the sequence QVQLKQSGPGLVQPSQSLSITCTVSGFSLT-SYGVHWVRQSPGKGLEWLGVIWSG GSTDYNAAF-ISRLSISKDNSKSQVFFKMNSLQANDTAIYYCAR-NGGNYYFDYWG QGTTLTVSS (SEQ ID NO:72). In a further embodiment, said antibody or fragment comprises a variable light chain sequence comprising a sequence which has at least 85%, more preferably at least 90%, more preferably at least 95%, more preferably at least 96%, more preferably at least 97%, more preferably at least 98%, more preferably at least 99% sequence identity with said sequence of SEQ ID NO: 68 and a variable heavy chain sequence comprising a sequence which has at least 85%%, more preferably at least 90%, more preferably at least 95%, more preferably at least 96%, more preferably at least 97%, more preferably at least 98%, more preferably at least 99% sequence identity with said sequence of SEQ ID NO: 72. In a particular embodiment said antibody or fragment comprises a variable light chain sequence comprising the sequence of SEQ ID NO: 68 and a variable light chain sequence comprising the sequence of SEQ ID NO: 72. Said antibody or fragment preferably potentiates FH activity, preferably inhibition of alternative complement activation, such as inhibition of hemolytic activity, inhibition of complement component 3 (C3) deposition, and/or an increase of binding of FH to C3b, iC3b and/or C3d. Said fragment preferably comprises at least a heavy chain variable domain (VH) and/or a light chain variable domain (VL). A more preferred fragment comprises at least a Fab fragment.

Optionally, the sequence of at least one of said CDR is optimized, thereby generating a variant antibody or fragment, for instance to (further) improve binding affinity, selectivity, FH potentiating ability and/or in vivo or storage stability. In a preferred embodiment, antibodies or fragments according to the invention have a high storage stability, in particular an improved storage stability as compared to antibody FH.07. In a further preferred embodiment, antibodies or fragments according to the invention have a high in vivo stability, in particular an improved in vivo stability as compared to antibody FH.07. In a further preferred embodiment, antibodies or fragments according to the invention have a high selectivity, in particular an increased selectivity as compared to antibody FH.07.

In addition, optionally at least one sequence in at least one of the framework regions of an antibody or fragment of the invention is optimized, for instance to improve binding efficacy or stability of the antibody or fragment or to reduce side-effects of non-human sequences after administration thereof to a human. This is for instance done by mutagenesis procedures. A skilled person is capable of generating antibody variants comprising at least one altered CDR or framework sequence. CDR and/or framework sequences are for instance optimized by mutating a nucleic acid molecule encoding such framework sequence. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine. In order to select an improved antibody or fragment, the binding affinity, FH potentiating ability and/or stability of the resulting variant antibodies or fragments are preferably tested, e.g. using test described herein. Once antibodies or fragments specific for FH, in particular for CCP18 of FH, have been obtained, the desired biological activity thereof, i.e. their ability to potentiate the activity of FH, can be tested by several methods known to the skilled person. As described herein before, potentiating the activity of FH preferably encompasses inhibition of hemolytic activity, inhibition of C3 deposition on cells, and/or an increase of binding of FH to C3b. Functional assay's to test these activities are described herein before and detailed in the Examples. Typically, up to three amino acid residues of a CDR sequence may vary while retaining the same specificity, depending on the number of amino acids the CDR is composed of. Hence, an antibody or fragment according to the invention preferably contains a heavy chain and light chain CDR1, CDR2 and CDR3 sequence wherein at most 3, preferably at most 2, more preferably at most 1 amino acid of each CDR is varied as compared to the heavy and light chain CDR1, CDR2 and CDR3 sequences of Table 1. It is further preferred that the antibody or fragment comprises a light chain CDR3 and a heavy chain CDR3 of the same antibody as depicted in table 1, a light chain CDR2 of said antibody wherein at most 1 amino acid is varied, and a light chain CDR1, heavy chain CDR1 and heavy chain CDR2 wherein at most 3 amino acids are varied. More preferably, the antibody or fragment comprises a light chain CDR2 and CDR3 and a heavy chain CDR3 of the same antibody as depicted in table 1, and a light chain CDR1, heavy chain CDR1 and heavy chain CDR2 wherein at most 2 amino acids, more preferably at most 1 amino acid, are varied.

The invention therefore further provides an isolated, synthetic or recombinant antibody or fragment thereof that specifically binds to complement control protein domain 18 (CCP18) of factor H (FH) comprising:

a light chain CDR1 sequence having a sequence which is at least 80% identical to the sequence SSVRY (SEQ ID NO:17), a light chain CDR2 sequence having a sequence ATS (SEQ ID NO:18) and a light chain CDR3 having a sequence which is at least 80% identical to the sequence QQWGTKPPT (SEQ ID NO:19), a heavy chain CDR1 having a sequence which is at least 80% identical to the sequence DFSLTNSG (SEQ ID NO:21), a heavy chain CDR2 having a sequence which is at least 80% identical to the sequence IWSGGTT (SEQ ID NO:22), and a heavy chain CDR3 sequence having a sequence which is at least 80% identical to the sequence ARNFGNYAVDY (SEQ ID NO:23), a light chain CDR1 sequence having a sequence which is at least 80% identical to the sequence SSVTY (SEQ ID NO:33), a light chain CDR2 sequence having a sequence ATS (SEQ ID NO:34) and a light chain CDR3 having a sequence which is at least 80% identical to the sequence QQRSSSNPLT (SEQ ID NO:35), a heavy chain CDR1 having a sequence which is at least 80% identical to the sequence GFSLTNYG (SEQ ID NO:37), a heavy chain CDR2 having a sequence which is at least 80% identical to the sequence IWSGGTT (SEQ ID NO:38), and a heavy chain CDR3 sequence having a sequence which is at least 80% identical to the sequence ARNFGNYAMDY (SEQ ID NO:39), a light chain CDR1 sequence having a sequence which is at least 80% identical to the sequence QSLVHSNG-NTY (SEQ ID NO:49), a light chain CDR2 sequence having a sequence KLS (SEQ ID NO:50) and a light chain CDR3 having a sequence which is at least 80% identical to the sequence SQSTHVPFT (SEQ ID NO:51), a heavy chain CDR1 having a sequence which is at least 80% identical to the sequence GFSLTNYG (SEQ ID NO:53), a heavy chain CDR2 having a sequence which is at least 80% identical to the sequence IWSGGNT (SEQ ID NO:54), and a heavy chain CDR3 sequence having a sequence which is at least 80% identical to the sequence AKNGDYGYTMDY (SEQ ID NO:55), a light chain CDR1 sequence having a sequence which is at least 80% identical to the sequence SSVNY (SEQ ID NO:65), a light chain CDR2 sequence having a sequence YTS (SEQ ID NO:66) and a light chain CDR3 having a sequence which is at least 80% identical to the sequence of QQFTSSPLT (SEQ ID NO:67), a heavy chain CDR1 having a sequence which is at least 80% identical to the sequence GFSLTSYG (SEQ ID NO:69), a heavy chain CDR2 having a sequence which is at least 80% identical to the sequence IWSGGST (SEQ ID NO:70), and a heavy chain CDR3 sequence having a sequence which is at least 80% identical to the sequence ARNGGNYYFDY (SEQ ID NO:71).

Said antibody preferably potentiates FH activity. Preferably, said antibody or fragment comprises heavy chain CDR1, CDR2 and/or CDR3 sequences and/or light chain CDR1, CDR2 and/or CDR3 sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to the indicated sequences.

The invention further provides an isolated, synthetic or recombinant antibody or fragment thereof that specifically binds to complement control protein domain 18 (CCP18) of factor H (FH) comprising:

a light chain CDR1 sequence having a sequence SSVTY (SEQ ID NO:17) optionally having 1 amino acid substitution, a light chain CDR2 sequence having a sequence ATS (SEQ ID NO:18) and a light chain CDR3 having a sequence QQWGTKPPT (SEQ ID NO:19)

optionally having 2 amino acid substitutions, preferably 1 amino acid substitution, a heavy chain CDR1 having a sequence DFSLTNSG (SEQ ID NO:21) optionally having 2 amino acid substitutions, preferably 1 amino acid substitution, a heavy chain CDR2 having a sequence IWSGGTT (SEQ ID NO:22) optionally having 2 amino acid substitutions, preferably 1 amino acid substitution, and a heavy chain CDR3 sequence ARNFGNYAVDY (SEQ ID NO:23) optionally having 2 amino acid substitutions, preferably 1 amino acid substitution, a light chain CDR1 sequence having a sequence SSVTY (SEQ ID NO:33) optionally having 1 amino acid substitution, a light chain CDR2 sequence having a sequence ATS (SEQ ID NO:34) and a light chain CDR3 having a sequence QQRSSSNPLT (SEQ ID NO:35) optionally having 2 amino acid substitutions, preferably 1 amino acid substitution, a heavy chain CDR1 having a sequence GFSLTNYG (SEQ ID NO:37) optionally having 2 amino acid substitutions, preferably 1 amino acid substitution, a heavy chain CDR2 having a sequence IWSGGTT (SEQ ID NO:38) optionally having 2 amino acid substitutions, preferably 1 amino acid substitution, and a heavy chain CDR3 sequence ARNFGNYAMDY (SEQ ID NO:39) optionally having 2 amino acid substitutions, preferably 1 amino acid substitution, a light chain CDR1 sequence having a sequence QSLVHSNGNTY (SEQ ID NO:49) optionally having 2 amino acid substitutions, preferably 1 amino acid substitution, a light chain CDR2 sequence KLS (SEQ ID NO:50) and a light chain CDR3 having a sequence SQSTHVPFT (SEQ ID NO:51) optionally having 2 amino acid substitutions, preferably 1 amino acid substitution, a heavy chain CDR1 having a sequence GFSLTNYG (SEQ ID NO:53) optionally having 2 amino acid substitutions, preferably 1 amino acid substitution, a heavy chain CDR2 having a sequence IWSGGNT (SEQ ID NO:54) optionally having 2 amino acid substitutions, preferably 1 amino acid substitution, and a heavy chain CDR3 sequence AKNGDYGYTMDY (SEQ ID NO:55) optionally having 2 amino acid substitutions, preferably 1 amino acid substitution, a light chain CDR1 sequence having a sequence SSVNY (SEQ ID NO:65) optionally having 1 amino acid substitution, a light chain CDR2 sequence having a sequence YTS (SEQ ID NO:66) and a light chain CDR3 having a sequence QQFTSSPLT (SEQ ID NO:67) optionally having 2 amino acid substitutions, preferably 1 amino acid substitution, a heavy chain CDR1 having a sequence GFSLTSYG (SEQ ID NO:69) optionally having 2 amino acid substitutions, preferably 1 amino acid substitution, a heavy chain CDR2 having a sequence IWSGGST (SEQ ID NO:70) optionally having 2 amino acid substitutions, preferably 1 amino acid substitution, and a heavy chain CDR3 sequence having a sequence ARNGGNYYFDY (SEQ ID NO:71) optionally having 2 amino acid substitutions, preferably 1 amino acid substitution.

Antibodies or fragments thereof according to the invention are preferably monoclonal antibodies or fragments. A monoclonal antibody is an antibody consisting substantially of a single molecular species. Monoclonal antibodies re obtained from a population of homogeneous antibodies, having the same sequence and binding the same epitope, with the exception of possible variant antibodies or fragments that have one or more mutations that have occurred spontaneously, e.g. during production. Monoclonal antibodies can be advantageously produced recombinantly so that amounts of the antibody can be obtained that are significantly higher than that of polyclonal antibodies present in an antiserum. However, polyclonal antibodies and fragments are also encompassed by the invention. An antibody or fragment according to the present invention further preferably is a chimeric or humanized antibody. Said antibody or fragment thus preferably comprises at least human light chain and heavy chain constant regions. More preferably said antibody or fragment also comprises human framework regions in the heavy and light chain variable regions. Further preferred are human antibodies or fragments, which consist entirely of human sequences. The use of chimeric, humanized or human antibodies is preferred over the use of non-human antibodies because the use of non-human antibodies or fragments for treatment of human diseases is hampered by a number of factors. The human body may recognize non-human antibodies as foreign, which will result in an immune response against the non-human antibodies or fragments, resulting in adverse side effects and/or rapid clearance of the antibodies or fragments from the circulation. The chance of side-effects is reduced when chimeric, humanized or human antibodies are administered to humans. In addition generally a longer half-life in the circulation is achieved when chimeric, humanized or human antibodies are used because of reduced clearance when compared to non-human antibodies. Preferably, human germline sequences are used for framework regions in antibodies or fragments according to the invention. The use of human germline sequences minimizes the risk of immunogenicity of said antibodies or fragments, because these sequences are less likely to contain somatic alterations which are unique to individuals from which the framework regions are derived, and may cause an immunogenic response when applied to another human individual.

Procedures for humanization of antibodies or the provide chimeric antibodies are well known in the art. Various recombinant DNA-based approaches have been established that are aimed at increasing the content of amino acid residues in antibodies that also occur at the same of similar position in human antibodies while retaining the specificity and affinity of the parental non-human antibody. For example, the framework regions of the variable regions of mouse antibodies are substituted by the corresponding human framework regions having the highest degree of homology, leaving the non-human CDR intact. Further methods suitable for humanizing antibodies according to the invention include, but are not limited to, grafting of CDRs (Queen, C et. al. 1989; Carter, P et al. 1992); resurfacing (Padlan, E A, et. al. 1991), superhumanization (Tan, P D A, et. al. 2002), human string content optimization (Lazar, G. A. et. al. 2007) and humaneering (Almagro, J C, et. al. 2008).

In one embodiment, an antibody or fragment according to the invention is a multispecific antibody, such as a bispecific antibody. Multispecific antibodies are monoclonal antibodies that have binding specificities for at least two different antigens and/or epitopes. In one embodiment, a bispecific antibody has binding specificity for FH, preferably comprising one variable light chain and at one variable heavy chain that specifically binds to CCP18 of FH as described herein, and has binding specificity for another antigen. In another embodiments, bispecific antibodies may bind to two different epitopes of FH.

An antibody or fragment according to the invention can be of any class. The "class" of an antibody refers to the type of constant domain or constant region possessed by its heavy chain. There are five major classes of antibodies: IgA, IgD, IgE, IgG, and IgM, some of which can be further divided into subclasses or isotypes, such as IgG1, IgG2, IgG3 and IgG4. In a preferred embodiment, an antibody or fragment according to the invention is of the IgG class, preferably IgG1 or IgG3.

Antibodies specific for a particular antigen, such as FH in accordance with the present invention, can be prepared by various methods known in the art. For instance, human FH can be used as an immunogen for eliciting antibodies. As another example, the CCP18 domain of human FH of a FH related protein can be used as an immunogen. One example of such method is by immunization and hybridoma generation as described in the Examples. Mouse monoclonal antibodies to FH can for instance be generated by immunizing mice, e.g. BALB/c mice, intraperitoneally with human factor H or a FH related protein such as FHR-1, optionally in the presence of an adjuvant, such as montanide, for instance at four week intervals. Several days after the fourth immunization, spleen cells can be fused with e.g. the myeloma cell line SP2/0. The presence of factor H specific antibodies in the supernatants of the hybridomas can be tested by ELISA. For instance, microtiterplates are coated with a moAb (e.g. rat anti-mouse kappa moAb RM19) to capture mouse IgG antibodies. Specificity of the antibodies was determined by biotinylated factor H. Another example of a method to provide FH-specific antibodies is by screening phage display libraries expressing recombinant nucleic acid sequences encoding immunoglobulin chains. Methods for antibody phage display have been used in the art and described extensively. Screening of the library for antibodies can be performed with the same antigen used for immunization, e.g. human FH, a FH related protein or the CCP18 domain of human FH.

The invention further provides an isolated, synthetic or recombinant nucleic acid molecule comprising a nucleic acid sequence encoding an antibody or fragment thereof according to the invention. Preferred nucleic acid molecules encode at least the heavy chain CDR1, CDR2 and CDR3 and/or the light chain CDR1, CDR2 and CDR3 of antibody FHR-1.8E4 as depicted in Table 1. Further preferred nucleic acid molecules encode at least the heavy chain CDR1, CDR2 and CDR3 and/or the light chain CDR1, CDR2 and CDR3 of antibody FHR-1.3B4 as depicted in Table 1. Further preferred nucleic acid molecules encode at least the heavy chain CDR1, CDR2 and CDR3 and/or the light chain CDR1, CDR2 and CDR3 of antibody FHR-1.11E1 as depicted in Table 1. Further preferred nucleic acid molecules encode at least the heavy chain CDR1, CDR2 and CDR3 and/or the light chain CDR1, CDR2 and CDR3 of antibody FHR-1.12F4 as depicted in Table 1. Preferably a nucleic acid molecule according to the invention has a length of at least 30 nucleotides, more preferably at least 50 nucleotides, more preferably at least 75 nucleotides. Preferably, a nucleic acid molecule according to the invention encodes a monoclonal chimeric or humanized antibody or fragment thereof comprising the heavy chain CDR sequences and light chain CDR sequences and/or the heavy chain variable region and the light chain variable region of antibody FHR-1.8E4 as depicted in Table 1. A further preferred nucleic acid molecule according to the invention encodes a monoclonal chimeric or humanized antibody or fragment thereof comprising the heavy chain CDR sequences and light chain CDR light chain variable region of antibody FHR-1.3B4 as depicted in Table 1. A further preferred nucleic acid molecule according to the invention encodes a monoclonal chimeric or humanized antibody or fragment thereof comprising the heavy chain CDR sequences and light chain CDR sequences and/or the heavy chain variable region and the light chain variable region of antibody FHR-1.11E1 as depicted in Table 1. A further preferred nucleic acid molecule according to the invention encodes a monoclonal chimeric or humanized antibody or fragment thereof comprising the heavy chain CDR sequences and light chain CDR sequences and/or the heavy chain variable region and the light chain variable region of antibody FHR-1.12F4 as depicted in Table 1. Nucleic acid sequences encoding heavy chain and light chain CDR's of antibodies FHR-1.8E4, FHR-1.3B4, FHR-1.11E1 and FHR-1.12F4 are depicted in table 1. However, nucleic acid molecules encoding a heavy or a light chain CDR of an antibody according to the invention comprising nucleic acid sequences which differ from the CDR nucleic acid sequences depicted in table 1 but comprising nucleic acid codons encoding the amino acid sequence of said heavy chain or light chain CDR sequence depicted in Table 1 are also encompassed by the invention.

Provided is therefore an isolated, synthetic or recombinant nucleic acid molecule comprising a nucleic acid sequence encoding at least the sequences of SEQ ID NO's 17, 18, 19, 21, 22 and 23. Further provided is an isolated, synthetic or recombinant nucleic acid molecule comprising a nucleic acid sequence encoding at least the sequences of SEQ ID NO's 33, 34, 35, 37, 38 and 39. Further provided is an isolated, synthetic or recombinant nucleic acid molecule comprising a nucleic acid sequence encoding at least the sequences of SEQ ID NO's 49, 50, 51, 53, 54 and 55. Further provided is an isolated, synthetic or recombinant nucleic acid molecule comprising a nucleic acid sequence encoding at least the sequences of SEQ ID NO's 65, 66, 67, 69, 70 and 71. Further provided is an isolated, synthetic or recombinant nucleic acid molecule comprising a nucleic acid sequence encoding at least the sequences of SEQ ID NO's 20 and 24. Further provided is an isolated, synthetic or recombinant nucleic acid molecule comprising a nucleic acid sequence encoding at least the sequences of SEQ ID NO's 36 and 40. Further provided is an isolated, synthetic or recombinant nucleic acid molecule comprising a nucleic acid sequence encoding at least the sequences of SEQ ID NO's 52 and 56. Further provided is an isolated, synthetic or recombinant nucleic acid molecule comprising a nucleic acid sequence encoding at least the sequences of SEQ ID NO's 68 and 72. Nucleic acid molecules encoding a heavy and/or light chain CDR or an antibody that is modified for instance by conservative amino acid substitution, are also encompassed by the invention.

A nucleic acid molecule or nucleic acid sequence according to the invention preferably comprises a chain of nucleotides, more preferably DNA and/or RNA. However, a nucleic acid molecule or nucleic acid sequence of the invention may comprise other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence, and are encompassed by the invention. The term "functional equivalent of a nucleic acid sequence" also encompasses a chain comprising non-natural nucleotides, modified nucleotides and/or non-nucleotide building blocks which exhibit the same function as natural nucleotides.

The invention further provides a vector comprising a nucleic acid molecule according to the invention. A preferred vector is a plasmid. A plasmid is defined herein as a circular, preferably double-stranded, DNA molecule. Methods for preparing a vector comprising a nucleic acid molecule according to the invention are well known in the art. Non-limiting examples of vectors suitable for generating a vector of the invention are retroviral and lentiviral vectors. A vector according to the invention can be used for a variety of applications. A vector according to the invention is preferably used for in vitro expression of a nucleic acid molecule according to the invention in a cell, preferably for the generation of antibodies or fragments according to the invention. Further, a vector according to the invention comprising a nucleic acid molecule according to the invention can be used for therapeutically. Administration of such vector to an individual, preferably a human, in need thereof results in expression of an antibody or fragment according to the invention in vivo.

Further provided is a recombinant cell comprising a nucleic acid molecule or vector according to the invention. Such nucleic acid molecule or vector is for preferably introduced into said cell so that the cell's nucleic acid translation machinery will produce the encoded antibodies or fragments. A nucleic acid molecule or vector according to the invention is preferably expressed in so called producer cells, such as for instance cells of a Chinese hamster ovary (CHO), NSO (a mouse myeloma) or 293(T) cell line, some of which are adapted to commercial antibody production. Proliferation of such producer cells results in a producer cell line capable of producing antibodies or fragments according to the invention. Preferably, said producer cell line is suitable for producing antibodies for use in humans. Hence, said producer cell line is preferably free of pathogenic agents such as pathogenic micro-organisms.

The invention further provides a method for producing an antibody or fragment according to the invention comprising providing a cell with a nucleic acid molecule or a vector according to the invention, and allowing said cell to translate the nucleic acid sequence comprised by said nucleic acid molecule or vector, thereby producing said antibody or fragment according to the invention. A method according to the invention preferably further comprises harvesting, purifying and/or isolating said antibody or fragment. Antibodies or fragments obtained with a method for producing an antibody or fragment according to the invention are also provided.

An antibody or fragment according to the invention can be advantageously used in therapeutic applications. Provided is thus a pharmaceutical composition comprising an antibody or fragment according to the invention and a pharmaceutically acceptable carrier, diluent and/or excipient. Also provided are pharmaceutical compositions comprising a nucleic acid molecule or vector according to the invention and at least one pharmaceutically acceptable carrier, diluent and/or excipient. Non-limiting examples of suitable carriers are for instance keyhole limpet haemocyanin (KLH), serum albumin (e.g. BSA or RSA) and ovalbumin. A preferred carrier is a solution, such as an aqueous solution, for example saline, or an oil-based solution. Non-limiting examples of excipients which can be incorporated in tablets, capsules and the like are a binder such as gum tragacanth, acacia, corn starch or gelatin, an excipient such as microcrystalline cellulose, a disintegrating agent such as corn starch, pregelatinized starch and alginic acid, a lubricant such as magnesium stearate, a sweetening agent such as sucrose, lactose or saccharin, and a flavoring agent such as peppermint, oil of wintergreen or cherry. When the dosage unit form is a capsule, it preferably contains, in addition to one or more of the excipients indicated above, a liquid carrier such as fatty oil. Various other materials may be present as coatings or to modify the physical form of the dosage unit. For instance, tablets may be coated with shellac and/or sugar or both. A pharmaceutical composition according to the invention is preferably suitable for human use.

The pharmaceutical compositions described herein can be administered in a variety of different ways. Examples include administering a pharmaceutical composition comprising an antibody according to the invention and containing a pharmaceutically acceptable carrier via oral, intranasal, rectal, topical, intraperitoneal, intravenous, intramuscular, subcutaneous, subdermal, transdermal, intrathecal, and intracranial methods. For oral administration, the active ingredient can be administered in solid dosage forms, such as capsules, tablets, and powders, or in liquid dosage forms, such as elixirs, syrups, and suspensions. Sterile compositions for injection can be formulated according to conventional pharmaceutical practice by dissolving or suspending the antibody or fragment of the invention in a vehicle for injection, such as water or a naturally occurring oil like sesame oil, coconut oil, peanut oil, cottonseed oil, etc., or a synthetic fatty vehicle like ethyl oleate. Buffers, preservatives and/or antioxidants may also be incorporated.

The invention further provides an antibody or fragment according to the invention for use in therapy. Further provided is a nucleic acid molecule according to the invention for use in therapy. Said therapy can be therapeutic or prophylactic. Antibodies or fragments according to the invention are particularly suitable for the treatment, alleviation or prevention of a disorder associated with alternative pathway complement activation. Provided is therefore an antibody or fragment according to the invention for use in the treatment, alleviation or prevention of a disorder associated with alternative pathway complement activation. Also provided is a nucleic acid molecule according to the invention for use in the treatment, alleviation or prevention of a disorder associated with alternative pathway complement activation. As used herein "a disorder associated with alternative complement activation" is herein defined as a disorder wherein unwanted and/or excessive alternative pathway complement activation leads to cell, tissue or extracellular matrix damage. Cells that may be damaged by unwanted and/or excessive alternative pathway activation are any cell that is in contact with blood, for instance red blood cells, epithelial cells, in particular hepatic and/or kidney epithelial cells, platelets, white blood cells, endothelial cells. Said disorder preferably is a disorder associated with impaired FH function or FH deficiency. More preferably, said disorder is a disorder associated with impaired FH function or FH deficiency but not with FH absence. Since the antibodies and fragments of the invention potentiate the function of FH, the antibodies and fragment are particularly suitable to block or reduce the effects of impaired FH function or FH deficiency. However, the potentiating anti-FH antibodies of the invention may also inhibit lysis of red blood cells that are incubated with serum of healthy individuals in which FH is artificially blocked. Hence, antibodies and fragments can also be used to block or reduce unwanted and/or excessive alternative pathway complement activation caused by factors other than impaired FH function or FH deficiency. Non-limiting examples of such orders that can be treated are atypical hemolytic uremic syndrome (aHUS), paroxysmal nocturnal hemoglobinuria (PNH), age-related macular degeneration (AMD), membranoproliferative glomerulonephritis (MPGN).

Atypical hemolytic uremic syndrome (aHUS), also referred to as complement mediated HUS, is characterized by hemolytic anemia, thrombocytopenia, systemic thrombotic microangiopathy (TMA) and renal failure. The onset of aHUS is typically in childhood and episodes of the disease are associated with e.g. infection, pregnancy, other disease, surgery, or trauma. Over 60% of aHUS patients die or develop end stage renal disease (ESRD) despite plasma exchange or plasma supplementation. Several mutations in components or factors of the complement system have been identified in patients with aHUS. Mutations in FH, FI FB, membrane cofactor protein (MCP), thrombomodulin (THBD) or C3 comprise about 50% of the known mutations in patients with aHUS of which mutations of FH are the most frequent (about 20-30% of aHUS patients). The majority of patients are heterozygous for the mutations, which nevertheless results in pathological FH deficiency. In addition, in about 10% of patients aHUS is caused by autoantibodies against FH, also resulting in reduced functional FH. Currently the standard treatment for aHUS is plasma supplementation or plasma exchange therapy. In addition eculizumab is used in the treatment of patients with aHUS. Renal transplantation is associated with a high risk of recurrence which is dependent on the mutation underlying aHUS. Transplantation is contraindicated in children with mutations in FH, FB, FI, C3 or THBD due to the increased risk of recurrence. Antibodies or fragments, preferably comprising at least the Fab fragment, according to the invention are particularly suitable for the treatment, alleviation or prevention of aHUS caused by a mutation in FH or by the presence of anti-FH autoantibodies. The potentiating effect on FH is independent on the CCP domain of FH carrying a mutation. For example, potentiating FH antibodies or fragments thereof are able to inhibit alternative complement activation in aHUS patients carrying a mutation in CCP1, CCP6, CCP7, CCP14, CCP17, CCP18, CCP19 and CCP20 of FH. However, since the antibodies and fragments of the invention may also potentiate the activity of FH in the absence of impaired FH function or FH deficiency, any form of complement dependent aHUS can be advantageously treated, alleviated or prevented with the antibodies or fragments of the invention.

Paroxysmal nocturnal hemoglobinuria (PNH) is caused by a genetic mutation in the X chromosome of a totipotent hematopoietic stem cell. The mutation leads to a deficiency in phosphatidylinositol glycan class A protein, which is critical for the synthesis of glycosylphophatidylinositol membrane anchoring proteins (GPI-AP). Inhibitor of the complement system CD55 is an example of such protein, which binds C3b at the host cell surface thereby preventing the formation of C3 convertase. Hence, a deficiency of these proteins results in unwanted or excessive complement activation. One of the main consequences of PNH is that red blood cells undergo lysis as a result of the excessive activity of the complement system. Recently, eculizumab has been approved for the treatment of PNH in several countries. Other therapies include blood transfusion, erythrocyte-stimulating agent therapy, treatment with corticosteroids and anabolic steroids. Since the antibodies and fragments of the invention may also potentiate the activity of FH independent from the levels of FH or FH function, thereby inhibiting the activation of the alternative pathway of the complement system, the antibodies and fragment can be advantageously used in PNH patients. In addition, because the antibodies and fragments of the invention act at the level of C3 deposition, as opposed to eculizumab that acts more downstream of the activation pathways, depletion of cells in the liver is reduced because less cells are opsonized by C3b.

Age-related macular degeneration (AMD) is damage to the retina affects usually affecting older individuals resulting in a loss of vision in the macula, the center of the visual field. Mutations and SNPs (single nucleotide polymorphisms) in FH have recently been implicated in about 35% of AMD patients. The SNP is located in CCP7 of FH and was demonstrated to influence the binding of FH to heparin thereby compromising the ability of FH to bind the host cell surface as well as the extracellular matrix. Antibodies or fragments, preferably comprising at least the Fab fragment, according to the invention are particularly suitable for the treatment, alleviation or prevention AMD characterized by decreased FH function, preferably by a SNP in the gene encoding FH.

Membranoproliferative glomerulonephritis (MPGN) is an uncommon cause of chronic nephritis that occurs primarily in children and young adults. It causes glomerular injury as a result of proliferation of mesangial and endothelial cells and expansion of the mesangial matrix, thickening of the peripheral capillary walls by subendothelial immune deposits and/or intramembranous dense deposits, and mesangial interposition into the capillary wall. MPGN is often associated with a total absence of FH. MPGN that can be treated with antibodies and/or fragments of the inventions is preferably associated with impaired FH function or FH deficiency but not with FH absence.

The invention thus provides an antibody or fragment or nucleic acid molecule according to the invention for use in the treatment, alleviation or prevention of a disorder associated with alternative pathway complement activation, wherein said disorder is selected from the group consisting of atypical haemolytic uraemic syndrome (aHUS), paroxysmal nocturnal haemoglobinuria (PNH), age-related macular degeneration (AMD), membranoproliferative glomerulonephritis (MPGN). Also provided is the use of an antibody or fragment, a nucleic acid molecule or a vector according to the invention for the preparation of a medicament for the treatment, alleviation or prevention of a disorder associated with alternative pathway complement activation. Said disorder is preferably selected from the group consisting of atypical haemolytic uraemic syndrome (aHUS), paroxysmal nocturnal haemoglobinuria (PNH), age-related macular degeneration (AMD), membranoproliferative glomerulonephritis (MPGN). Preferred antibodies for use as a medicament or prophylactic agent in accordance with the invention are antibodies or fragments thereof, preferably the Fab, Fab' or $F(ab)_2$ or F(ab')2 fragment, that comprise the heavy and light chain CDR1, CDR2 and CDR3 of antibody as depicted in Table 1. Said antibody or fragment is preferably a monoclonal humanized or chimeric antibody or fragment.

The invention further provides a method for inhibiting alternative complement activation comprising administering to an individual an antibody or fragment according to the invention, or a nucleic acid molecule or a vector according to the invention.

The invention further provides a method for treating, alleviating or preventing a disorder associated with alternative pathway complement activation comprising administering to an individual in need thereof a therapeutically effective amount of an antibody or fragment according to the invention. Also provided is a method for treating, alleviating or preventing a disorder associated with alternative pathway complement activation comprising administering to an individual in need thereof a therapeutically effective amount of a nucleic acid molecule or vector according the invention. Further provided is a method for treating, alleviating or preventing a disorder associated with alternative pathway complement activation comprising administering to an individual in need thereof a therapeutically effective amount of a pharmaceutical composition according to the invention. Said disorder is preferably selected from the group consisting of atypical hemolytic uremic syndrome (aHUS), paroxysmal nocturnal hemoglobinuria (PNH), age-related macular degeneration (AMD), membranoproliferative glomerulonephritis (MPGN). As used herein, an "individual" is a human or an animal that has a complement system as part of its immune system, preferably a mammal. In a particularly preferred embodiment the individual is a human. Preferred antibodies for use in the methods of the invention are antibodies or fragments thereof, preferably the Fab, Fab', $F(ab)_2$ or F(ab')2 fragment, that comprise the heavy and light chain CDR1, CDR2 and CDR3 of antibody FHR-1.8E4, that comprise the heavy and light chain CDR1, CDR2 and CDR3 of antibody FHR-1.3B4, that comprise the heavy and light chain CDR1, CDR2 and CDR3 of antibody FHR-1.11E1 or that comprise the heavy and light chain CDR1, CDR2 and CDR3 of antibody FHR-1.12F4 as depicted in Table 1. Said antibody or fragment is preferably a monoclonal humanized or chimeric antibody or fragment.

The compositions containing the antibodies, fragments, nucleic acid molecules of the invention can be administered for prophylactic and/or therapeutic treatments. In therapeutic applications antibodies, fragment, nucleic acid molecules or compositions according to the invention are administered to an individual, preferably a human, already suffering from a disease and/or already showing symptoms of the disease in an amount sufficient to counteract the symptoms of the disease and/or its complications. In prophylactic applications, antibodies, fragment, nucleic acid molecules or compositions according to the invention are administered to an individual, before the individual shows symptoms of the disorder to prevent the development of these symptoms or its complications. For instance, individuals that carry a genetic mutation that may or will cause a disorder associated with alternative complement activation can be prophylactically treated with antibodies, fragment, nucleic acid molecules or compositions according to the invention. The antibodies, fragment, or nucleic acid molecules are typically present in a pharmaceutical composition according to the invention in a therapeutically effective amount, which is an amount sufficient to remedy the disorder associated with unwanted or excessive activation of the alternative pathway of the complement system.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

TABLE 1

Amino acid and nucleotide sequences of antibodies FH.07, FHR-1.8E3, FHR-1.3B4, FHR-1.11E1, FHR-1.12F4 and FHR-1.14C4. (CDR numbering according to the IMGT numbering system (Lefranc 1997, Lefranc 1999 and Lefranc et al. 2003).

| Antibody | Type | Identity | Sequence | SEQ ID NO |
|---|---|---|---|---|
| FH.07 | amino acid | LC CDR1 | SSVKY | 1 |
| FH.07 | amino acid | LC CDR2 | ATS | 2 |
| FH.07 | amino acid | LC CDR3 | QQWSIIPPT | 3 |
| FH.07 | amino acid | VL | QIVLSQSPTFLSASPGEKVTVTC RASSSVKYMHWYQQKPGASPK PWIFATSNLASGVPARFSGSGS GTSYSLTISRVEAEDAATYYCQ QWSIIPPTFGNGTKLELK | 4 |
| FH.07 | amino acid | HC CDR1 | DFSLARYG | 5 |
| FH.07 | amino acid | HC CDR2 | IWSGGTA | 6 |
| FH.07 | amino acid | HC CDR3 | ARNFGNYAVDY | 7 |
| FH.07 | amino acid | VH | QVQLQQSGPGLVQPSQSLSITC TVSDFSLARYGVHWIRQSPGKG LEWLGVIWSGGTADYNAAFISR LNINKDNSKSQVFFKMNSLQA NDTAIYYCARNFGNYAVDYWG QGTS | 8 |
| FH.07 | nucleic acid | LC CDR1 | tcaagtgtcaaatac | 9 |
| FH.07 | nucleic acid | LC CDR2 | gccacatcc | 10 |
| FH.07 | nucleic acid | LC CDR3 | cagcagtggagtattatcccacccacg | 11 |

TABLE 1-continued

Amino acid and nucleotide sequences of antibodies FH.07, FHR-1.8E3,
FHR-1.3B4, FHR-1.11E1, FHR-1.12F4 and FHR-1.14C4. (CDR numbering according to
the IMGT numbering system (Lefranc 1997, Lefranc 1999 and Lefranc et al. 2003).

| Antibody | Type | Identity | Sequence | SEQ ID NO |
|---|---|---|---|---|
| FH.07 | nucleic acid | VL | caaattgttctctcccagtctccaacattcctgt ctgcatctccaggtgagaaggtcacagtgact tgcagggccagttcaagtgtcaaatacatgca ctggtatcagcagaaaccaggagcctccccca aaccctggattttttgccacatccaacctggcttc tggagtccctgctcgcttcagtggcagtgggtc tgggacctcttattctctcacaatcagcagagt ggaggctgaagatgctgccacttattactgcc agcagtggagtattatcccacccacgttcggta atgggaccaagctggagctgaaac | 12 |
| FH.07 | nucleic acid | HC CDR1 | gatttctcattagctaggtatggt | 13 |
| FH.07 | nucleic acid | HC CDR2 | atatggagtggtggaaccgca | 14 |
| FH.07 | nucleic acid | HC CDR3 | gccagaaattttggtaactacgctgtggactac | 15 |
| FH.07 | nucleic acid | VH | caggtgcagctgcagcagtcaggacctggcct agtgcagccctctcagagcctgtccattacctg cacagtctctgatttctcattagctaggtatggt gtacactggattcgccagtctccaggaaaggg tctggagtggctgggagtgatatggagtggtg gaaccgcagactataatgcagctttcatatcca gactgaacatcaacaaggacaattccaagag ccaagtttctcttaaaatgaacagtctccaagc taatgacacagccatatattactgtgccagaa attttggtaactacgctgtggactactggggtc aaggaacctcag | 16 |
| FHR-1.8E4 | amino acid | LC CDR1 | SSVRY | 17 |
| FHR-1.8E4 | amino acid | LC CDR2 | ATS | 18 |
| FHR-1.8E4 | amino acid | LC CDR3 | QQWGTKPPT | 19 |
| FHR-1.8E4 | amino acid | VL | QIVLSQSPAILSASPGEKVTMC RASSSVRYMHWYQQKAGSSPT AWIFATSNLASGVPPRFSGSGS GTSYSLTISRVEAEDAATYYCQ QWGTKPPTFGAGTKLELK | 20 |
| FHR-1.8E4 | amino acid | HC CDR1 | DFSLTNSG | 21 |
| FHR-1.8E4 | amino acid | HC CDR2 | IWSGGTT | 22 |
| FHR-1.8E4 | amino acid | HC CDR3 | ARNFGNYAVDY | 23 |
| FHR-1.8E4 | amino acid | VH | QVQLKQSGPGLVQPSQSLSITC TVSDFSLTNSGVHWVRQSPGK GLEWLGVIWSGGTTEYNAAFM SRLTITKDNSKSQVFFKMNSLL VDDTGIYYCARNFGNYAVDYW GQGTSVTVSS | 24 |
| FHR-1.8E4 | nucleic acid | VL | ccaattgttctctcccagtctccagcaatcctgt ctgcatctccaggggagaaggtcacaatgact tgcagggccagctcaagtgttaggtacatgca ctggtaccagcagaaggcaggatcctcccca cagcctggattttttgccacatccaacctggcttc tggagtccctcctcgcttcagtggcagtgggtct gggacctcttactctctcacaatcagcagagtg gaggctgaagatgctgccacttattactgcca gcagtggggtactaagccacccacgttcggtg ctgggaccaagctggagctgaaac | 28 |

TABLE 1-continued

Amino acid and nucleotide sequences of antibodies FH.07, FHR-1.8E3,
FHR-1.3B4, FHR-1.11E1, FHR-1.12F4 and FHR-1.14C4. (CDR numbering according to
the IMGT numbering system (Lefranc 1997, Lefranc 1999 and Lefranc et al. 2003).

| Antibody | Type | Identity | Sequence | SEQ ID NO |
|---|---|---|---|---|
| FHR-1.8E4 | nucleic acid | VH | caggtgcagctgaagcagtcaggacctggcct agtgcagccctcacagagcctgtccatcacctg cacagtctctgatttctcattaactaattctggt gtacactgggttcgccagtctccaggaaaggg tctggagtggctgggagtgatatggagtggtg gaaccacagagtataatgcagctttcatgtcc agactgaccatcaccaaggacaactccaaga gccaagtttctcttaaaatgaacagtctgctag ttgatgatacaggcatatattactgtgccaga aattttggtaattatgctgtggactactggggt caaggaacctcagtcaccgtctcctcag | 32 |
| FHR-1.3B4 | amino acid | LC CDR1 | SSVTY | 33 |
| FHR-1.3B4 | amino acid | LC CDR2 | ATS | 34 |
| FHR-1.3B4 | amino acid | LC CDR3 | QQRSSSNPLT | 35 |
| FHR-1.3B4 | amino acid | VL | QIVLSQSPTILSASPGEKVTMTC RASSSVTYMHWYQQKPGSSPK PWIYATSNLASGVPARFSGSGS GTSYSLTISRVEAEDAATYYCQ QRSSSNPLTFGAGTKLELK | 36 |
| FHR-1.3B4 | amino acid | HC CDR1 | GFSLTNYG | 37 |
| FHR-1.3B4 | amino acid | HC CDR2 | IWSGGTT | 38 |
| FHR-1.3B4 | amino acid | HC CDR3 | ARNFGNYAMDY | 39 |
| FHR-1.3B4 | amino acid | VH | QVQLRQSGPGLVQPSQSLSITCT VSGFSLTNYGVYWVRQSPGKG LEWLGVIWSGGTTDYSAAFISR LSISKDNSKSQVFFKMNSLQAD DTAIYYCARNFGNYAMDYWGQ GTSVTVSS | 40 |
| FHR-1.3B4 | nucleic acid | VL | caaattgttctctcccagtctccaacaatcctgt ctgcatctccaggggagaaggtcacaatgact tgcagggccagctcaagtgtaacttacatgca ctggtaccagcagaagccaggatcctccccca aaccctggatttatgccacatccaacctggctt ctggagtccctgctcgcttcagtggcagtgggt ctgggacctcttactctctcacaatcagcagag tggaggctgaagatgctgccacttattactgcc agcagcgcagtagtagtaacccgctcacgttc ggtgctgggaccaagctggagctgaaat | 44 |
| FHR-1.3B4 | nucleic acid | VH | caggtgcagctgaggcagtcaggacctggcct agtgcagccctcacagagcctgtccatcacctg cacagtctctggtttctcattaactaactatggt gtatattgggttcgccagtctccaggaaaggg tctggagtggctgggagtgatatggagtgga ggaaccactgactatagtgcagctttcatatcc agactgagcatcagcaaggacaactccaaga gccaagtttctcttaaaatgaacagtctgcaag ctgatgacacagccatatactactgtgccaga atttggcactacgctatggactacatggggtca aggaacctcacaccggtctccacag | 48 |
| FHR-1.11E1 | amino acid | LC CDR1 | QSLVHSNGNTY | 49 |
| FHR-1.11E1 | amino acid | LC CDR2 | KLS | 50 |
| FHR-1.11E1 | amino acid | LC CDR3 | SQSTHVPFT | 51 |

TABLE 1-continued

Amino acid and nucleotide sequences of antibodies FH.07, FHR-1.8E3,
FHR-1.3B4, FHR-1.11E1, FHR-1.12F4 and FHR-1.14C4. (CDR numbering according to
the IMGT numbering system (Lefranc 1997, Lefranc 1999 and Lefranc et al. 2003).

| Antibody | Type | Identity | Sequence | SEQ ID NO |
|---|---|---|---|---|
| FHR-1.11E1 | amino acid | VL | DVVMTQTPLSLPVSLGDQASIS CRSSQSLVHSNGNTYLHWYLQ KPGQSPKLLIYKLSNRFSGVPD RFSGSGSGTDFTLKISRVEAEDL GVYFCSQSTHVPFTFGSGTKLE IK | 52 |
| FHR-1.11E1 | amino acid | HC CDR1 | GFSLTNYG | 53 |
| FHR-1.11E1 | amino acid | HC CDR2 | IWSGGNT | 54 |
| FHR-1.11E1 | amino acid | HC CDR3 | AKNGDYGYTMDY | 55 |
| FHR-1.11E1 | amino acid | VH | QVQLKQSGPGLVQPSQSLSITC TVSGFSLTNYGVHWVRQPPGK GLEWLGVIWSGGNTDYNAAFIS RLSISKDNSKSQVFFKMNSLQA DDTAIYYCAKNGDYGYTMDYW GQGTSVTVSS | 56 |
| FHR-1.11E1 | nucleic acid | VL | gatgttgtgatgacccaaactccactctccctg cctgtcagtcttggagatcaagcctccatctctt gcagatctagtcagagccttgtacacagtaat ggaaacacctatttacattggtacctgcagaa gccaggccagtctccaaagctcctgatctacaa actttccaaccgattttctggggtcccagacag gttcagtggcagtggatcagggacagatttca cactcaagatcagcagagtggaggctgagga tctgggagtttatttctgctctcaaagtacacat gttccattcacgttcggctcggggacaaagttg gaaataaaac | 60 |
| FHR-1.11E1 | nucleic acid | VH | caggtgcagctgaagcagtcaggacctggcct agtgcagccctcacagagcctgtccatcacctg cacagtctctggttttttcattaactaactatggt gtacactgggttcgccagcctccaggaaaggg tctggagtggctgggagtgatatggagtggtg gaaacacagactataatgctgctttcatatcca gactgagcatcagcaaggacaactccaagag ccaagttttctttaaaatgaacagtctgcaagc tgatgacacagccatatactactgtgccaaaa atggggattacggctatactatggactactgg ggtcaaggaacctcagtcaccgtctcctcag | 64 |
| FHR-1.12F4 | amino acid | LC CDR1 | SSVNY | 65 |
| FHR-1.12F4 | amino acid | LC CDR2 | YTS | 66 |
| FHR-1.12F4 | amino acid | LC CDR3 | QQFTSSPLT | 67 |
| FHR-1.12F4 | amino acid | VL | ENVLTQSPAIMSASLGEKVTMS CRASSSVNYMYWYQQKSDASK LSWIYYTSNLAPGVPARFSGSG SGNSYSLTISSMEGEDAATYYC QQFTSSPLTFGAGTKLELK | 68 |
| FHR-1.12F4 | amino acid | HC CDR1 | GFSLTSYG | 69 |
| FHR-1.12F4 | amino acid | HC CDR2 | IWSGGST | 70 |
| FHR-1.12F4 | amino acid | HC CDR3 | ARNGGNYYFDY | 71 |

TABLE 1-continued

Amino acid and nucleotide sequences of antibodies FH.07, FHR-1.8E3,
FHR-1.3B4, FHR-1.11E1, FHR-1.12F4 and FHR-1.14C4. (CDR numbering according to
the IMGT numbering system (Lefranc 1997, Lefranc 1999 and Lefranc et al. 2003).

| Antibody | Type | Identity | Sequence | SEQ ID NO |
|---|---|---|---|---|
| FHR-1.12F4 | amino acid | VH | QVQLKQSGPGLVQPSQSLSITC TVSGFSLTSYGVHWVRQSPGKG LEWLGVIWSGGSTDYNAAFISR LSISKDNSKSQVFFKMNSLQAN DTAIYYCARNGGNYYFDYWGQ GTTLTVSS | 72 |
| FHR-1.12F4 | nucleic acid | VL | gaaaatgtgctcacccagtctccagcaatcat gtctgcatctctaggggagaaggtcaccatga gctgcagggccagctcaagtgtaaattacatg tactggtaccagcagaagtcagatgcctccccc aactcatggatttattacacatccaacctggct cctggagtcccagctcgcttcagtggcagtggg tctgggaactcttattctctcacaatcagcagc atggagggtgaagatgctgccacttattactg ccagcagtttactagttccccactcacgttcggt gctgggaccaagctggagctgaaac | 76 |
| FHR-1.12F4 | nucleic acid | VH | caggtgcagctgaagcagtcaggacctggcct agtgcagccctcacagagcctgtccatcacctg cacagtctctggtttctcattaactagctatggt gtacactgggttcgccagtctccaggaaaggg tctggagtggctgggagtgatatggagtggtg gaagcacagactataatgcagctttcatatcc agactgagcatcagcaaggacaattccaaga gccaagttttctttaaaatgaacagtctgcaag ctaatgacacagccatatattactgtgccaga aacggaggtaactactactttgactactgggg ccaaggcaccactctcacagtctcctcag | 80 |
| FHR-1.14C4 | amino acid | LC CDR1 | QSLFNSGNQKNY | 81 |
| FHR-1.14C4 | amino acid | LC CDR2 | WAS | 82 |
| FHR-1.14C4 | amino acid | LC CDR3 | QNDYSYPLT | 83 |
| FHR-1.14C4 | amino acid | VL | DIVMTQSPSSLTVTAGEKVTMS CKSSQSLFNSGNQKNYLTWYQ QKPGQPPKLLIYWASTRESGVP DRFTGSGSGTDFTLTISSVQAED LAVYYCQNDYSYPLTFGAGTKL ELK | 84 |
| FHR-1.14C4 | amino acid | HC CDR1 | GYSFTGYN | 85 |
| FHR-1.14C4 | amino acid | HC CDR2 | IDPYYGDT | 86 |
| FHR-1.14C4 | amino acid | HC CDR3 | ARAFYRDYALDY | 87 |
| FHR-1.14C4 | amino acid | VH | EVQLQQSGPELEKPGASVKISC KASGYSFTGYNMHWVKQSNGT SLEWIGKIDPYYGDTSYNQRFK GKATLTVDKSSSTAYMQLKSLT SEDSAVYYCARAFYRDYALDYW GRGTSVTVSS | 88 |
| FHR-1.14C4 | nucleic acid | VL | gacattgtgatgacacagtctccatcctccctg actgtgacagcaggagagaaggtcactatga gctgcaagtccagtcagagtctgtttaacagtg gaaatcaaaagaactacttgacctggtaccag cagaaaccagggcagcctcctaaactgttgat ctactgggcatccactagggaatctggggtccc tgatcgcttcacaggcagtggatctggaacag atttcactctcaccatcagcagtgtgcaggctg aagacctggcagtttattactgtcagaatgatt atagttatccgctcacgttcggtgctgggacca agctggagctgaaac | 89 |

TABLE 1-continued

Amino acid and nucleotide sequences of antibodies FH.07, FHR-1.8E3,
FHR-1.3B4, FHR-1.11E1, FHR-1.12F4 and FHR-1.14C4. (CDR numbering according to
the IMGT numbering system (Lefranc 1997, Lefranc 1999 and Lefranc et al. 2003).

| Antibody | Type | Identity | Sequence | SEQ ID NO |
|---|---|---|---|---|
| FHR-1.14C4 | nucleic acid | VH | gaggtccagctgcagcagtctggacctgagct ggagaagcctggcgcttcagtgaagatatcct gcaaggcttctggttactcattcactggctaca acatgcactgggtgaagcagagcaatggaac gagccttgagtggattggaaaaattgatcctt actatggtgatactagctacaaccagaggttc aagggcaaggccacattgactgtagacaaat cctccagcacagcctacatgcagctcaagagc ctgacatctgaggactctgcagtctattactgt gcaagagcgttctatagagactatgctttgga ctactggggtcgaggaacctcagtcaccgtctc ttcag | 90 |
| consensus sequence | amino acid | LC CDR1 | SSVXY X = R, T, N | 91 |
| consensus sequence | amino acid | LC CDR2 | X₁X₂S X₁ = A, K, Y X₂ = T, L | 92 |
| consensus sequence | amino acid | HC CDR1 | X₁FSLTX₂X₃G X₁ = D, G X₂ = N, S X₃ = S, Y | 93 |
| consensus sequence | amino acid | HC CDR2 | IWSGGXT x = T, N, S | 94 |
| consensus sequence | amino acid | HC CDR3 | ARNX₁GNYX₂X₃DY X₁ = F, G X₂ = A, Y X₃ =V, M, F | 95 |
| consensus sequence | amino acid | LC CDR1 | SSVXY X = R, T | 96 |
| consensus sequence | amino acid | LC CDR2 | ATS | 97 |
| consensus sequence | amino acid | HC CDR1 | X₁FSLTNX₂G X₁ = D, G X₂ = S, Y | 98 |
| consensus sequence | amino acid | HC CDR2 | IWSGGTT | 99 |
| consensus sequence | amino acid | HC CDR3 | ARNFGNYAXDY X = V, M | 100 |

LC = light chain,
HC = heavy chain,
CDR = Complementary-determining regions,
VH = heavy chain variable region,
VL = light chain variable region.

A) Binding of biotinylated FH (FH-bt) by each monoclonal antibody in the absence or presence of unlabelled full length FH or FH fragments was assessed by ELISA. Binding is expressed as percentage of the binding of FH-bt observed without any addition of unlabelled competitors (set to 100%, dashed line). B) Competition ELISA with FH-bt, using anti-FH and anti-FHR-1 mAbs as catching mAb (indicated on the X-axis) and anti-FH.07 or anti-FH.16 (as a control) as competitors. C) Competition ELISA with FH-bt as in B, but with only using anti-FH.07 as catching mAb and anti-FHR-1 mAbs (indicated on the X-axis) as competing mAbs.

Figure 2:
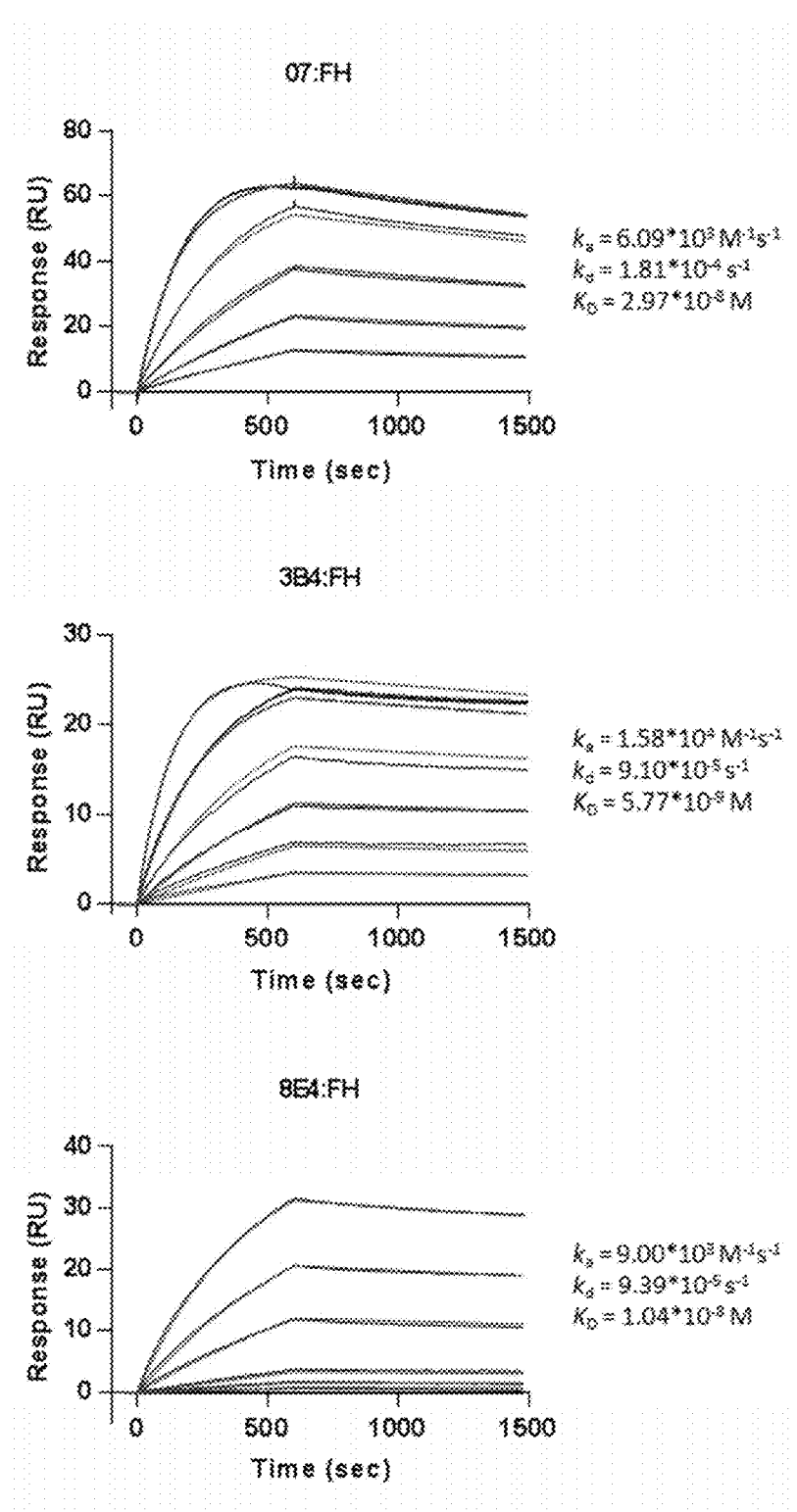
Figure 2:
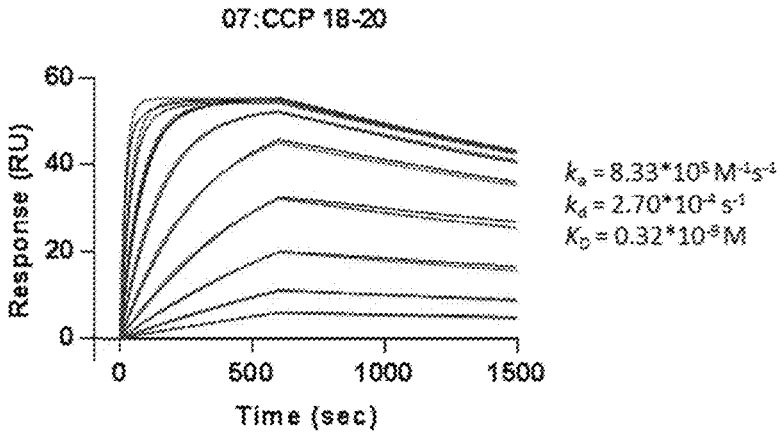
Figure 2:
Figure 2:
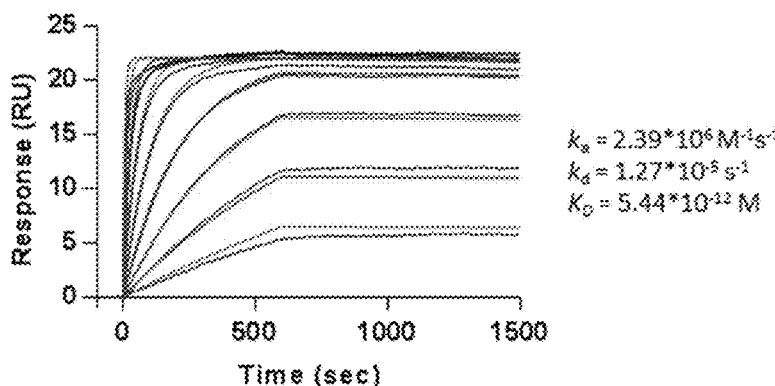
Figure 2:
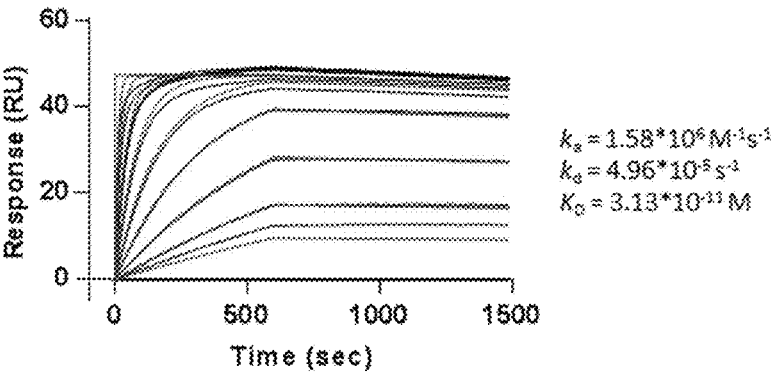
Figure 2:
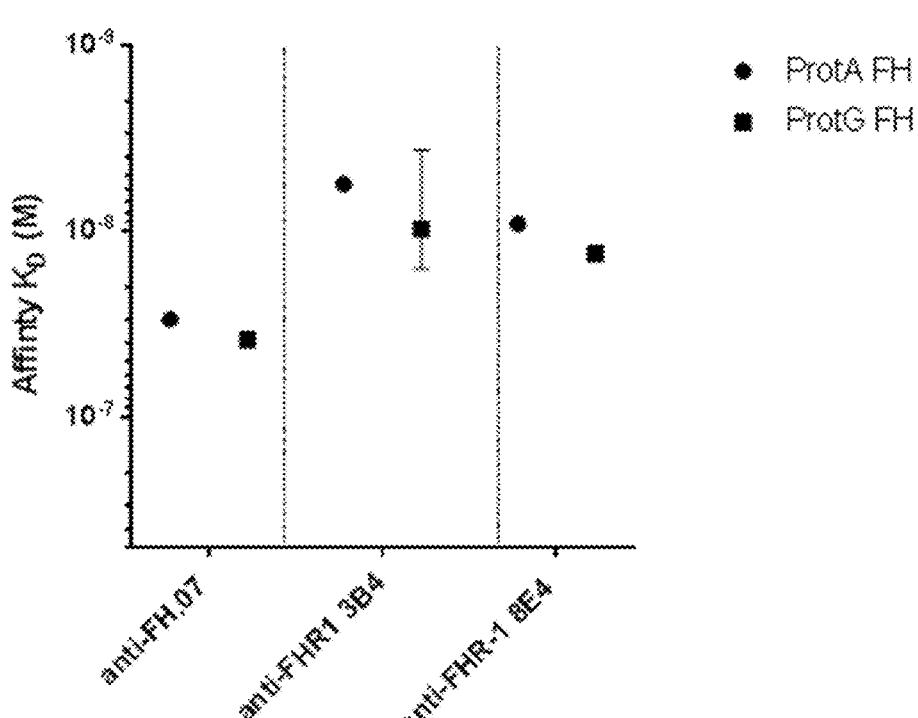
Figure 2:
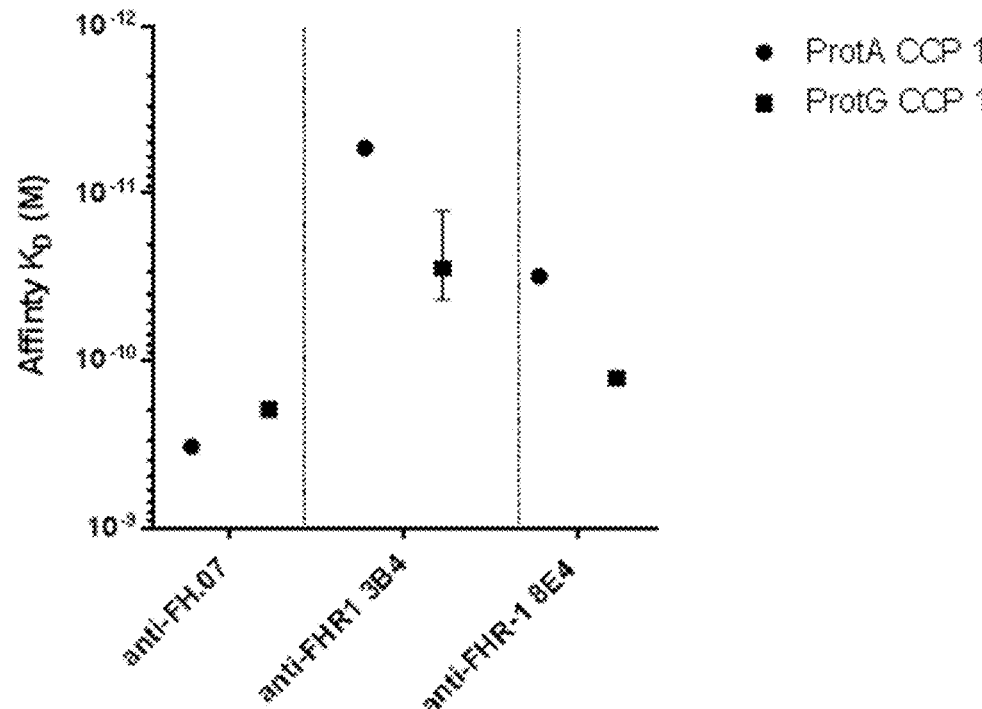

FIG. 2: SPR analysis of anti-FHR-1 mAbs to determine their affinity for FH. Affinity was determined by SPR on a ProtA or ProtG chip.

(A-B) Examples of sensorgrams of capturing the indicated monoclonal antibodies before flowing either full length FH (A) or a fragment of FH comprised of domain 18-20 (B) over the surface. Fitted plots (black lines) and corresponding results indicated next to each graph were obtained following a 1:1 binding model.

(C-D) Summary of all affinity analyses done using either ProtA or ProtG chip for full length (C), or CCP18-20 (D) for antibodies FH.07, 3B4 and 8E4.

Figure 3:
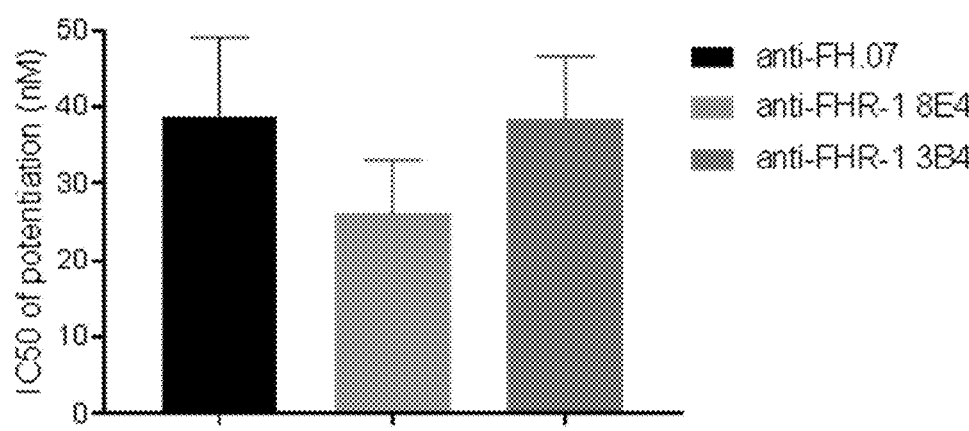
Figure 3:
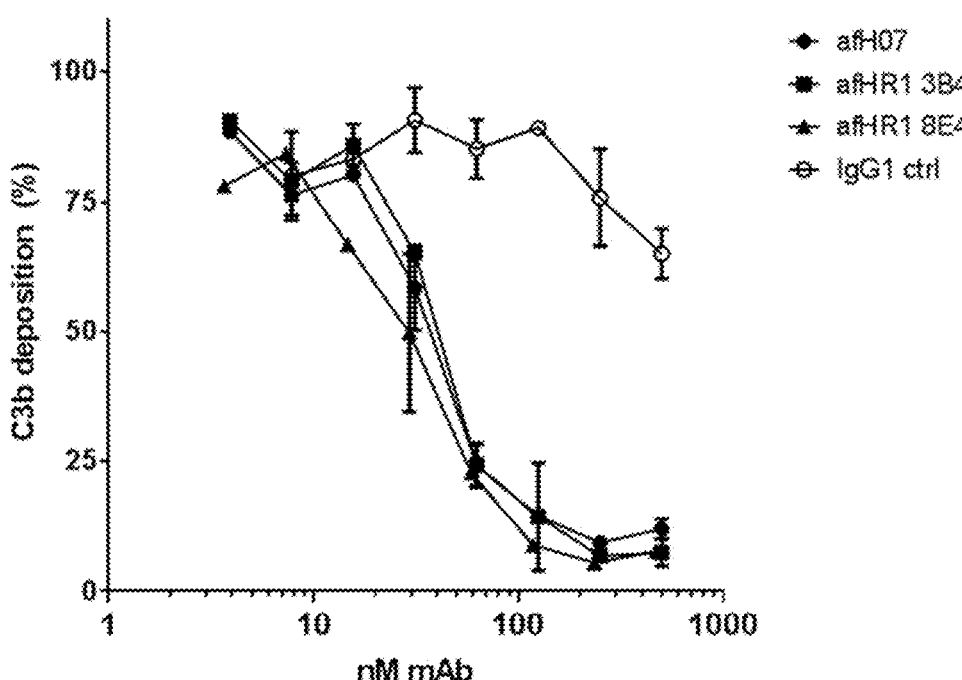
Figure 3:
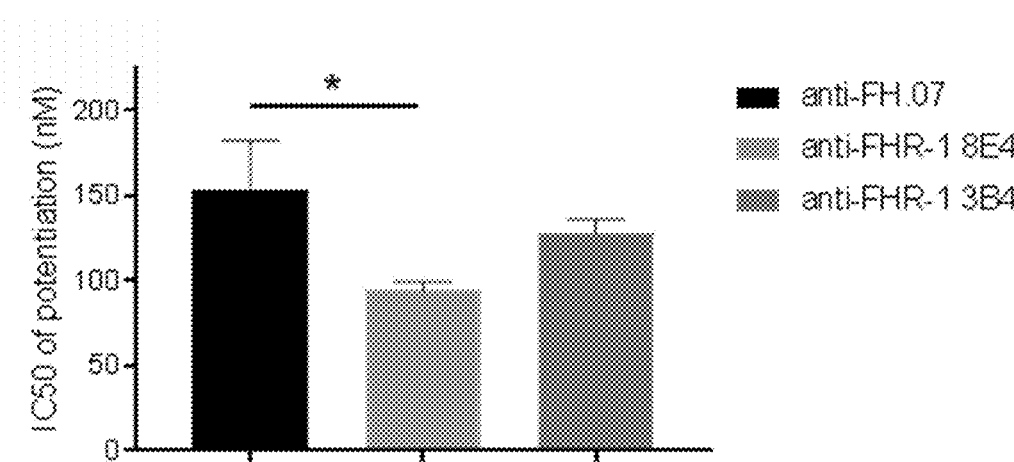

FIG. 3: Functional characterisation of anti-FHR-1 mAbs. A)

C3b deposition on LPS, using 10% (v/v) normal human serum, with addition of the indicated antibodies, determined by ELISA. Graphs are representative for multiple independent experiments, n=4.

Upper panel: $IC_{50}$ of potentiation of C3b deposition.

Lower panel: Representative figure for C3b deposition on LPS for increasing concentrations of FH.07, 3B4 and 8E4. C3b deposition in 10% (v/v) normal human serum without addition of any antibody was set to 100%. IgG1 ctrl is a negative control antibody.

Figure 4:
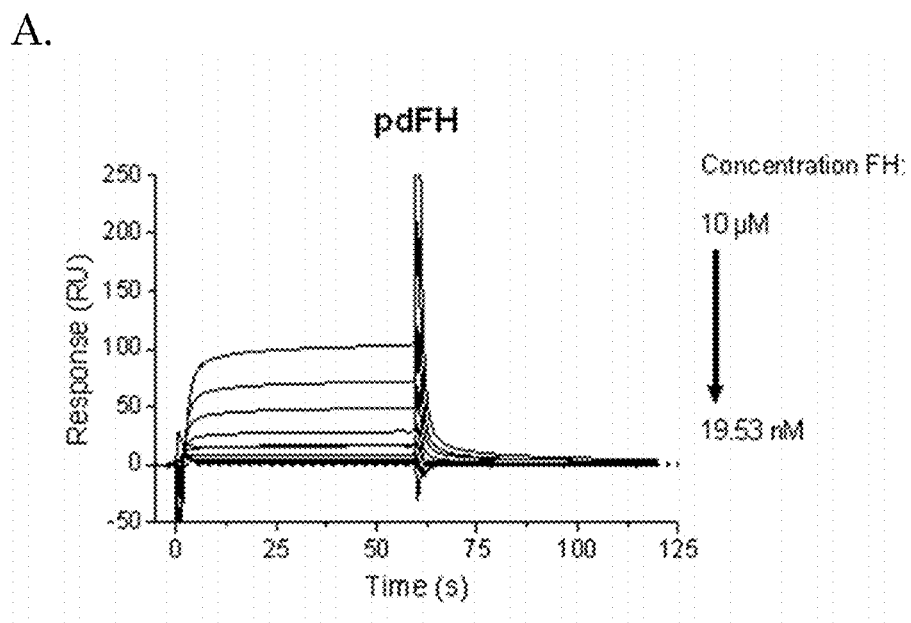
Figure 4:
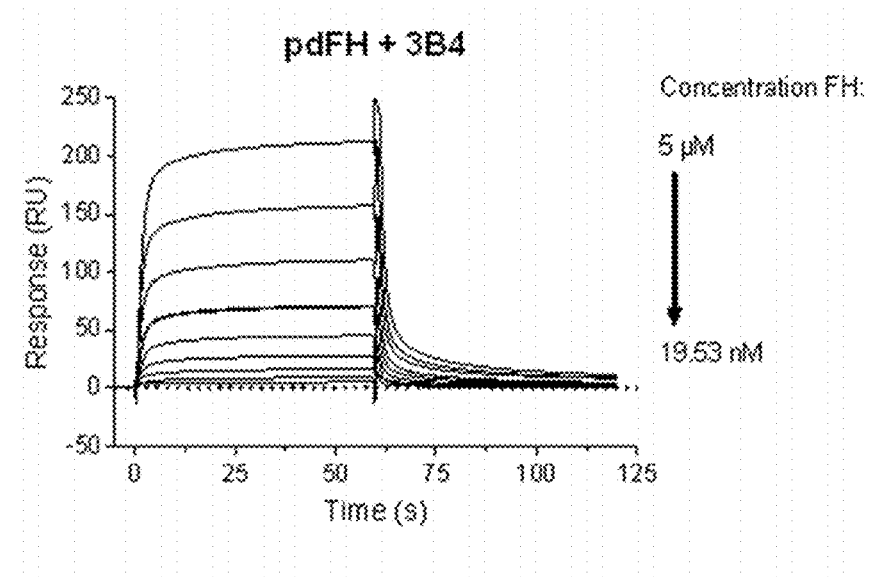
Figure 4:
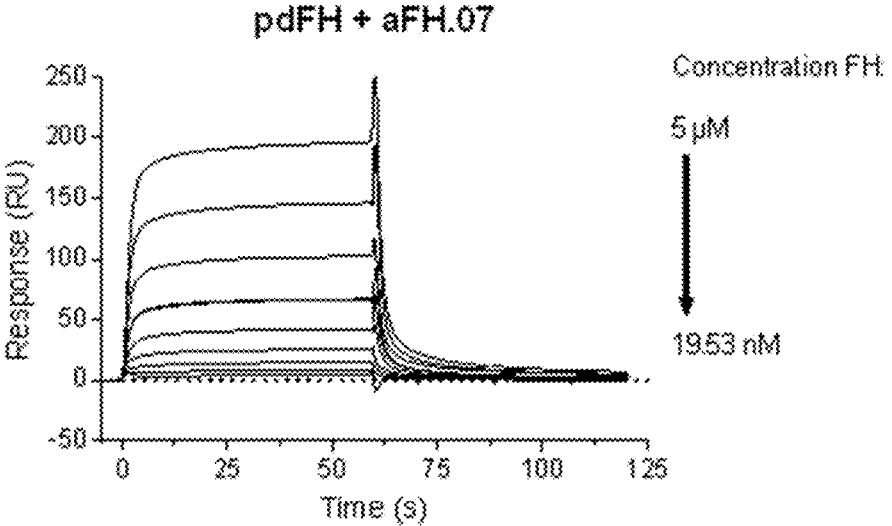
Figure 4:
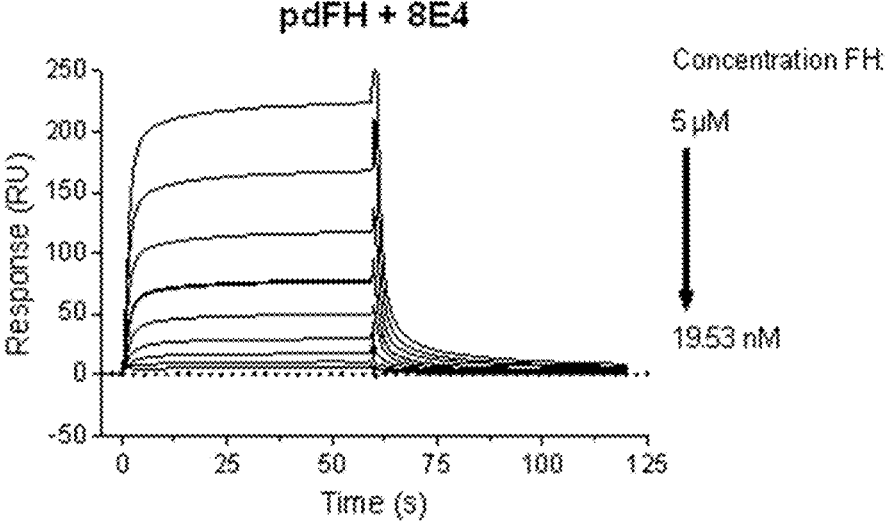
Figure 4:
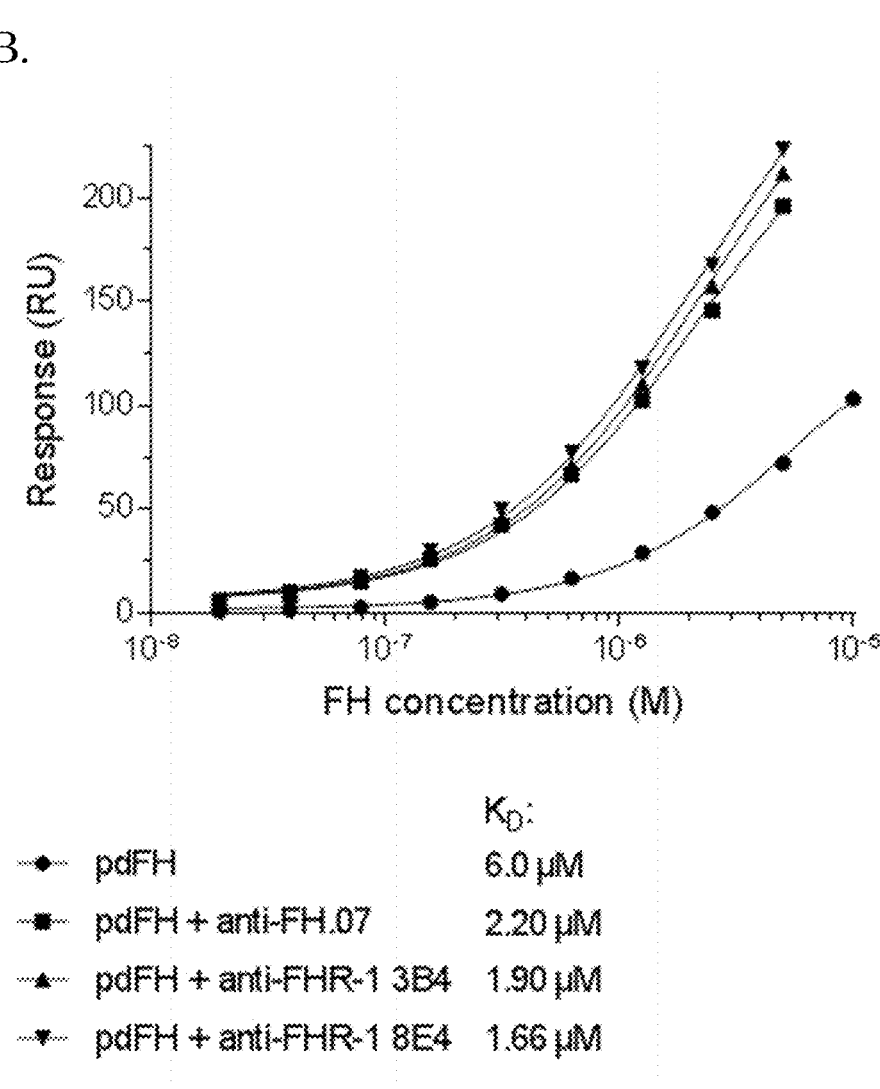

B) Hemolytic assay using sheep red blood cells (SRBC) and 10% (v/v) normal human serum. Hemolysis was induced by inhibiting FH with anti-FH.09 (Serum+FH Inh.), resulting in 89% lysis. Monoclonal antibodies against FH and FHR-1 were added as indicated $IC_{50}$ of hemolysis calculated from multiple experiments. n=2-4, statistical analysis was done using ordinary one-way ANOVA, * indicates $p \leq 0.05$ FIG. 4: A. Sensograms of SPR analysis of FH interactions with C3b with and without addition of anti-FH.07, anti-FHR-1 3B4 or anti-FHR-1 8E4 Fab' fragments as indicated. Addition of Fab' fragments increased the measured RU by at least 2-fold on all surfaces, reflecting increased FH binding. B. The equilibrium analysis of binding and estimated $K_D$ of interactions shows an increase in affinity of 2.7, 3.2 and 3.6 times, respectively for each Fab'.

EXAMPLES

Materials and Methods

Reagents

Human purified factor H was obtained from CompTech. (Tyler, Texas USA). Rat anti-mouse kappa (RM19) was obtained from Sanquin (Business Unit reagents, Sanquin, Amsterdam, the Netherlands). High Performance ELISA buffer (HPE) was obtained from Sanquin. Recombinant FH CCPs (CCP 15-18, CCP 15-19, CCP 18-20 or CCP 19-10) were a kind gift of dr. Christoph Schmidt and were produced as described before (Schmidt et al. 2008). Mouse monoclonal antibodies (mAbs) against human FH were made previously. Anti-FH.07 (murine IgG1) is directed against CCP 18, anti-FH.09 (murine IgG1) is directed against CCP 6 and anti-FH.16 (murine IgG1) is directed against CCP 16/17. Anti-IL-6.8 was use as irrelevant isotype control and was obtained from Sanquin. Anti-C3.19 reacts with an epitope on the C3d fragment of the molecule and has been described before (Wolbink et al. 1993).

Expression of rhFHR Proteins

Recombinant human factor H-related (rhFHR) proteins, containing a C-terminal 6×-histidine (6×His) tag, were produced and purified as previously described (Pouw et al. 2015). In short, proteins were expressed by transient transfection of pcDNA3.1 expression vectors in HEK293F cells, after which proteins were purified from the supernatant by $Ni^{2+}$ affinity chromatography using HisTrap™ High Performance 1 ml columns (GE Healthcare Life Sciences, Freiburg, Germany). rFHRs were filtrated and concentrated using Amicon® Ultra Centrifugal Filter Devices (Merck Millipore, Darmstadt, Germany).

Immunization and Hybridoma Generation

Mouse monoclonal antibodies to FHR-1 were generated by immunizing BALB/c mice intraperitoneally with 25 µg rhFHR-1 in montanide as adjuvans at four week intervals. Three days after the fourth booster immunization, spleen cells were fused with the myeloma cell line SP2/0. The presence of FHR-1 specific antibodies in the supernatants of the hybridomas was tested by ELISA. In short, microtiterplates were coated with a rat anti-mouse kappa moAb (RM19) to capture mouse IgG antibodies. Specificity of the antibodies was determined by biotinylated rhFHR-1. Binding of biotinylated rhFHR-1 was determined by incubation with 0.1% (v/v) streptavidin conjugated with HRP, in HPE for 30 min. The ELISA was further developed using 100 µg/mL 3,5,3',5'-tetramethylbenzidine (TMB) in 0.1 M sodium acetate containing 0.003% (v/v) $H_2O_2$, pH 5.5. Substrate conversion was stopped by addition of 100 µL $H_2SO_4$ and absorbance was measured at 450 nm and corrected for the absorbance at 540 nm with a Synergy 2 Multi-Mode plate reader (BioTek Instruments, Winooski, VT, USA). All ELISA steps were performed with a final volume of 100 µL per well.

Epitope Mapping mAbs and Competition Assay

The location of the epitope of anti-FHR-1 mAbs was determined using recombinant human FH fragments composed of multiple CCP domains (15-18, 15-19, 18-20 or 19-20). In short, anti-FHR-1 mAbs were captured on a RM-19 coated microtiterplate to assure optimal binding conformation. Next, biotinylated FH, mixed with a 100-fold higher concentration of the indicated unlabeled recombinant FH-fragments, was incubated on the plate for 1 hour. Binding of biotinylated FH was determined by incubation with 0.01% (v/v) streptavidin conjugated with poly-HRP, in HPE for 30 min. The ELISA was further developed as described above. To determine whether the anti-FHR-1 mAbs competed with anti-FH.07 for the binding of FH, a similar set-up was used. In short, mAbs were directly coated to the plate and binding of biotinylated FH (FH-bt) in the absence or presence of a 10-fold higher concentration of indicated mAbs was assessed by ELISA as described above.

C3 Deposition on LPS

Polysorp 96-wells microtiter plates (Nunc) were coated with *Salmonella* typhosa LPS (40 µg/mL, L-6386 Sigma-Aldrich) in PBS, 0/N at room temperature. LPS activates the alternative pathway of complement. After washing with PBS+0.1% (w/v) Tween-20, 10% (v/v) NHS was incubated in Veronal buffer (VB; 3 mM barbital, 1.8 mM sodium barbital, 145 mM NaCl, pH 7.4) containing 0.05% (w/v) gelatin, 5 mM $MgCl_2$, 10 mM EGTA and 0.1% (w/v) Tween-20 in the presence or absence of anti-FH/anti-FHR-1 mAbs, isotype controls or aIL6-8 AB as a negative control at indicated concentrations. C3b deposition was detected with biotinylated mAb anti-C3.19 (0.55 µg/mL in HPE) followed by incubation with 0.01% (v/v) streptavidin conjugated with poly-HRP, in HPE for 30 min. The ELISA was further developed as described above.

SRBC Hemolytic Assay

FH functionality was determined with a hemolytic assay as described previously by Sanchez-Corral et al. (2004) and Wouters et al. (2008), with some adjustments. Pre-diluted human serum (20%, v/v), containing 20 µg/ml anti-FH.09, was pre-incubated with the indicated mAbs and mixed in a 1-to-1 ratio with sheep red blood cells (SRBCs) to reach a final concentration of 10% (v/v) serum and $1.05 * 10^8$ cells/ml in VB with 5 mM $MgCl_2$ and 10 mM EGTA, or VB with 10 mM EDTA as blank, followed by incubation at 37° C. for 75 minutes while shaking. Lysis was stopped by adding 100 µl ice-cold VB with 20 mM EDTA followed by centrifugation (2.5 minutes, 1,800 RPM/471 RCF, 7° C.). Hemolysis was measured as absorbance of the supernatants at 412 nm, corrected for background absorbance measured at 690 nm, and expressed as percentage of the 100% lysis control (SRBCs incubated with 0.6% (w/v) Saponin). As negative control, SRBCs were incubated with serum diluted in VB supplemented with 10 mM EDTA to prevent complement activation.

Using graphpad prism 7.04, EC50 of hemolysis was calculated from multiple experiments and statistical comparisons were made by ordinary one-way ANOVA and Dunnett's multiple comparisons test.

Determining Binding Affinity (SPR)

Surface plasmon resonance (SPR) experiments were performed using a BiaCore T200 (GE Healthcare) and CM5 sensor chips (GE Healthcare) in accordance with the manufacturer's instructions. In short, to determine its affinity, anti-FH.07, anti-FHR-1 3B4 or anti-FHR-1 8E4 were captured onto a ProtA or ProtG coupled chip and either full length FH or a fragment of FH comprising domain 18-20 was flown over the captured moAB at decreasing concentrations.

Binding Affinity of Factor H to C3b

Figure 1:
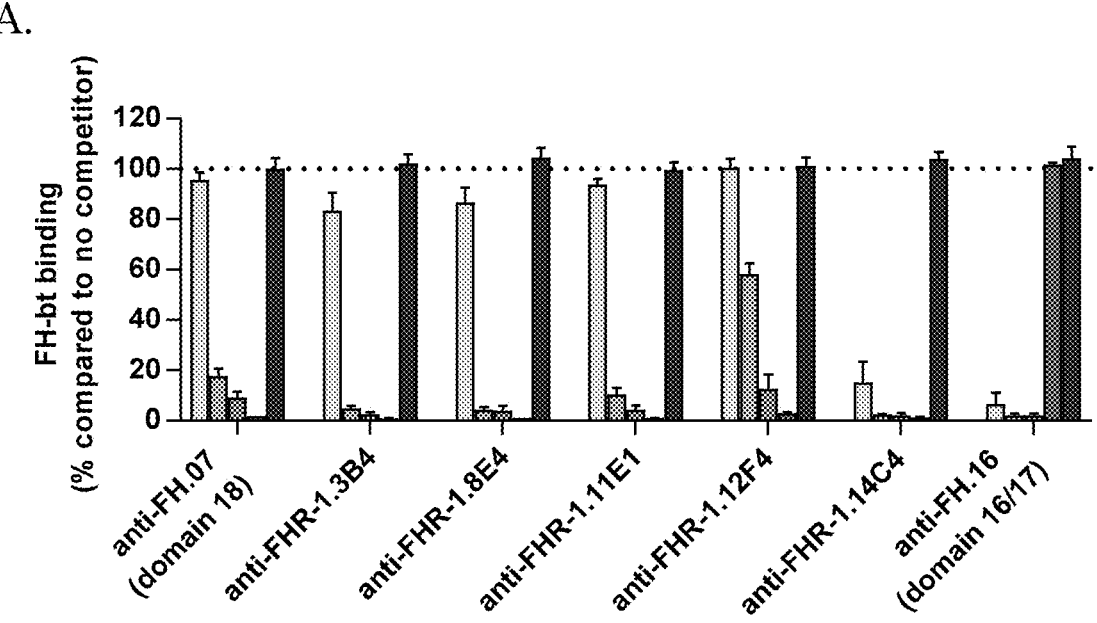
FIG. 1: Competition assays to map the epitope location of the anti-FHR-1 antibodies.
Figure 1:
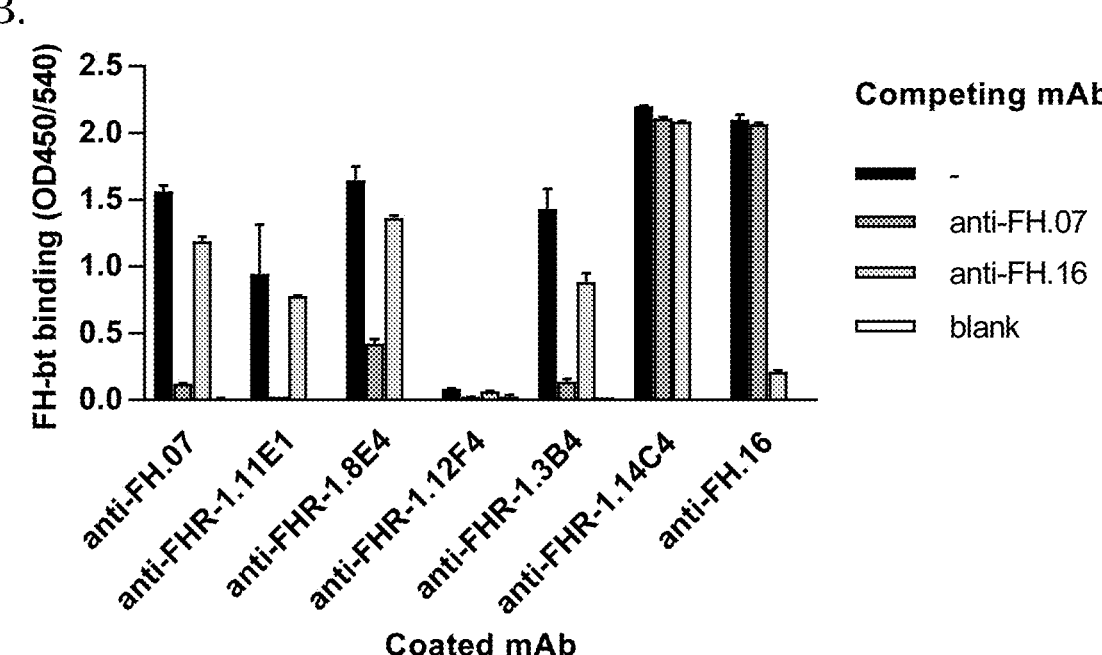
Figure 1:
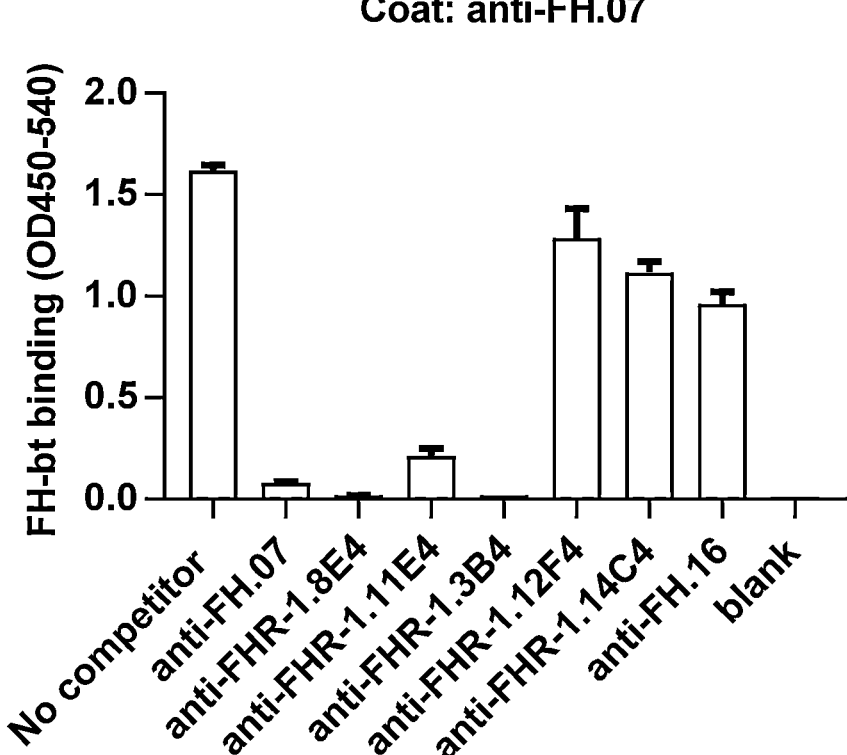

Binding of FH to C3b in the presence of the anti-FH moAbs was determined by surface plasmon resonance using a Biacore T200 instrument (GE Healthcare, Little Chalfont, UK). Purified C3b (Complement Technologies) was immobilized onto a flow cell of a CM5 Biacore Sensor Chip (GE Healthcare) using standard amine coupling. The remaining flow cell was used as reference surface and prepared by performing a coupling reaction without the addition of any protein. A response of 2000 response units (RUs) was obtained after coupling with C3b. SPR experiments were Mapping Binding Sites In order to map the binding site of the monoclonal antibodies, the reactivity of the moAbs was tested against recombinant FH fragments comprising varying CCP domains (CCP 15-18, CCP 15-19, CCP 18-20 and CCP 19-20) and full length human FH. As indicated in FIG. 1A, FHR-1.3B4, FHR-1.8E4, FHR-1.11E1, FHR-1.12F4 and FHR-1.14C4 bind to recombinant fragments CCP 15-18, CCP 15-19 and CCP 18-20 in varying degree, but not to CCP 19-20. This indicates that all antibodies are specific for CCP 18 of FH.

Epitope Mapping

Competition assay's were performed with agonistic anti-FH antibody FH.07. As shown in FIGS. 1B and 1C, binding of FHbt to coated anti-FH.07, 11E1, 8E4 and 3B4 is competed off by anti-FH.07, but not by 14C4 or the isotype control anti-FH.16. This indicates that anti-FH.07, 11E1, 8E4 and 3B4 are binding to identical or overlapping epitopes in CCP18, while 14C4 binds to another, non-overlapping epitope in CCP 18. Binding of 12F4 is also competed off by anti-FH.07 but to a lesser degree, indicating that this antibody binds to the same epitope, but possibly has a lower affinity.

Binding Affinity

All antibodies FH.07, 8E4 and 3B4 bind to human FH and CCP18-20 of FH with nanomolar or sub-nanomolar affinities. Both antibodies 8E4 and 3B4 have higher binding affinities than that of FH.07 for both full length FH and CCP18-20, see FIG. 2 and table 2.

TABLE 2

| | Binding kinetics for antibodies FH.07, 3B4 and 8E4. | | | | | |
|---|---|---|---|---|---|---|
| | FH | | | CCP18-20 | | |
| | ka $(M^{-1}s^{-1})$ | kd $(s^{-1})$ | KD × $10^{-8}$ (M) | ka $(M^{-1}s^{-1})$ | kd $(s^{-1})$ | KD × $10^{-9}$ (M) |
| FH.0.7 | 6.09 × $10^3$ | 1.81 × $10^{-4}$ | 2.97 | 8.33 × $10^5$ | 2.70 × $10^{-4}$ | 0.32 |
| 3B4 | 1.58 × $10^4$ | 9.10 × $10^{-5}$ | 0.58 | 2.39 × $10^6$ | 1.27 × $10^{-5}$ | 5.44 × $10^{-3}$ |
| 8E4 | 9.00 × $10^3$ | 9.39 × $10^{-5}$ | 1.04 | 1.58 × $10^6$ | 4.96 × $10^{-5}$ | 0.03 | performed at 37° C. using a flow rate of 10 μl/min and in phosphate buffered saline pH 7.4 (PBS, Orphi Farma) supplemented with 0.01% (w/v) Tween-20 (Merck) (PBS-T).

To determine the effect of the antibodies without interference of possible cross-linking via the moAb, recombinantly produced Fab' fragments of the moAbs were used. Fab' fragments were mixed with plasma purified FH (pdFH). FH was injected for 60 seconds at different concentrations (10-0.01953 μM for FH alone and 5-0.01953 μM for complexed with moAb Fab' fragments) over the chip in absence or presence of 10 μM (at least 2 fold molar ratio excess) of either anti-FH.07, anti-FHR-1 3B4 or anti-FHR-1 8E4 Fab' fragments. Each Fab' fragment was also injected without addition of FH to determine any interactions of the Fab' fragments with the surfaces. The pdFH injection was followed by a dissociation of 60 seconds and surface was regenerated between each cycle by a single injection of 1 M NaCl (Merck).

Data was analyzed using Scrubber 2 (Biologic Software) affinities were determined by equilibrium analysis.

Results

Monoclonal Antibodies

Monoclonal antibodies FHR-1.3B4, FHR-1.8E4, FHR-1.11E1, FHR-1.12F4 and FHR-1.14C4 were raised against recombinant human factor H-related protein 1 (FHR-1).

C3 Deposition on LPS

FH.07, 3B4, 8E4, 11E1 and 12F4 all decrease the C3b deposition on LPS (shown in FIG. 3A for FH.07, 3B4 and 8E4). In contrast, 14C4 increased C3b deposition on LPS. FIG. 3A shows C3 deposition on LPS for increasing concentrations of FH.07, 3B4 and 8E4. It is shown that 8E4 inhibits C3 deposition to a larger extent than FH.07.

Hence, all mAbs that compete with anti-FH.07 also potentiate the function of FH which results in a decreased complement activation. Remarkably, although also binding to CCP 18, the non-competing mAb (14C4) resulted in an opposite effect, which is inhibition of FH function, thus more C3b deposition. As shown in table 3, the $IC_{50}$ in the LPS deposition assay of 8E4 is lower than that of FH.07.

SRBC Hemolytic Activity

Anti-FH.07, 3B4, 8E4 and 11E1 decrease the induced SRBC hemolysis. 12F4 shows the same effect, but to a lesser degree. Hence, all mAbs that compete with anti-FH.07 also potentiate the function of FH on the SRBC surface, which results in a decreased complement mediated hemolysis. 3B4, 8E4 both have a higher effect in potentiating FH in this assay in higher concentrations. As shown in table 3 and FIG. 3B, the $IC_{50}$ in the hemolytic assay of both 8E4 and 3B4 are lower than that of FH.07.

TABLE 3

IC$_{50}$ values of the anti-FHR-1 mAbs in the LPS C3b deposition assay and the hemolytic assay, compared to anti-FH.07. For FH.07, 3B4 and 8E4 the values are based on multiple experiments.

| | LPS C3b dep. assay | | Hemolytic assay | |
|---|---|---|---|---|
| mAb | IC$_{50}$ (nM) | Relative | IC$_{50}$ (nM) | Relative |
| Anti-FH.07 | 38.8 | 1.00 | 152.7 | 1.00 |
| Anti-FHR.1.3B4 | 38.4 | 0.99 | 94.0 | 0.83 |
| Anti-FHR-1.8E4 | 26.3 | 0.68 | 127.5 | 0.62 |
| Anti-FHR-1.11E1 | 25.04 | | n.d. | — |
| Anti-FHR-1.12F4 | 345.20 | | n.d. | — |

Binding Affinity of Factor H to C3b

Under normal conditions FH shows interaction with C3b with an estimated K-D of 6.0 µM. However, the addition of Fab' fragments of anti-FH/07, aFHR-1 3B4 or aFHR-1 8E4 increases the response on the C3b coated surface (FIG. 4A) and is represented in an increased estimated affinities of 2.20 µM, 1.90 µM and 1.66 µM respectively (FIG. 4B).

REFERENCES

Almagro J C, Fransson J. 2008. Humanization of antibodies. Frontiers in Bioscience 13: 1619-33.

Carter P, Presta L, Gorman C M, Ridgway J B, Henner D, Wong W L, Rowland A M, Kotts C, Carver M E, Shepard H M. 1992. Humanization of an anti-p185HER2 antibody for human cancer therapy. Proc. Natl. Acad. Sci. U.S.A. 89(10):4285-9.

Chen Y, Wiesmann C, Fuh G, Li B, Christinger H W, McKay P, de Vos A M, Lowman H B. Selection and analysis of an optimized anti-VEGF antibody: crystal structure of an affinity-matured Fab in complex with antigen. J Mol Biol. 1999; 293(4):865-81.

Cheng Z Z, Corey M J, Parepalo M, Majno S, Hellwage J, Zipfel P F, Kinders R J, Raitanen M, Meri S, Jokiranta T S. Complement factor H as a marker for detection of bladder cancer. Clin Chem. 2005; 51(5): 856-63.

Corey M J, Kinders R J, Poduje C M, Bruce C L, Rowley H, Brown L G, Hass G M, Vessella R L. Mechanistic studies of the effects of anti-factor H antibodies on complement-mediated lysis. J Biol Chem. 2000; 275 (17):12917-25.

Lazar G A1, Desjarlais J R, Jacinto J, Karki S, Hammond P W. 2007. A molecular immunology approach to antibody humanization and functional optimization. Mol. Immunol., 44(8):1986-98.

Lefranc M P, "Unique database numbering system for immunogenetic analysis" Immunology Today, 18, 509 (1997). PMID: 9386342.

Lefranc M P, "The IMGT unique numbering for immunoglobulins, T cell Receptors and Ig-like domains", The Immunologist. 1999; 7, 132-136.

Lefranc M P, Pommié C, Ruiz M, Giudicelli V, Foulquier E, Truong L, Thouvenin-Contet V, and Lefranc G, "IMGT unique numbering for immunoglobulin and T cell receptor variable domains and Ig superfamily V-like domains" Dev. Comp. Immunol., 27, 55-77 (2003). PMID 12477501.

Padlan, E A. 1991. A possible procedure for reducing the immunogenicity of antibody variable domains while preserving their ligand-binding properties. Mol. Immunol., 28(4-5):489-98.

Pouw, Richard B, Mieke C Brouwer, Judy Geissler, Laurens V van Herpen, Sacha S Zeerleder, Walter A Wuillemin, Diana Wouters, and Taco W Kuijpers. 2016. "Complement Factor H-Related Protein 3 Serum Levels Are Low Compared to Factor H and Mainly Determined by Gene Copy Number Variation in CFHR3." PLoS ONE 11 (3): e0152164.

Queen C, Schneider W P, Selick H E, Payne P W, Landolfi N F, Duncan J F, Avdalovic N M, Levitt M, Junghans R P, Waldmann T A. 1989. A humanized antibody that binds to the interleukin 2 receptor. Proc. Natl. Acad. Sci. U.S.A. 86(24):10029-33.

Sánchez-Corral, Pilar, C González-Rubio, Santiago Rodríguez de Córdoba, and Margarita López-Trascasa. 2004. "Functional Analysis in Serum from Atypical Hemolytic Uremic Syndrome Patients Reveals Impaired Protection of Host Cells Associated with Mutations in Factor H." Molecular Immunology 41 (1): 81-84.

Schmidt, Christoph Q, Andrew P Herbert, Henry G Hocking, D Uhrin, and Paul N Barlow. 2008. "Translational Mini-Review Series on Complement Factor H: Structural and Functional Correlations for Factor H." Clinical and Experimental Immunology 151 (1): 14-24.

Tan P, Mitchell D A, Buss T N, Holmes M A, Anasetti C, Foote J. 2002. "Superhumanized" antibodies: reduction of immunogenic potential by complementarity-determining region grafting with human germline sequences: application to an anti-CD28. J. Immunol., 169(2):1119-25.

Wolbink, G J, J Bollen, J W Baars, R J ten Berge, a J Swaak, J Paardekooper, and C Erik Hack. 1993. "Application of a Monoclonal Antibody against a Neoepitope on Activated C4 in an ELISA for the Quantification of Complement Activation via the Classical Pathway." Journal of Immunological Methods 163 (1): 67-76.

Wouters, Diana, Mieke C Brouwer, Mohamed R Daha, and C Erik Hack. 2008. "Studies on the Haemolytic Activity of Circulating C1q-C3/C4 Complexes." Molecular Immunology 45 (7): 1893-99.

The invention claimed is:

1. A method of identifying an antibody or a fragment thereof that binds Complement Factor H (FH) and potentiates FH activity, the method comprising:

(a) providing a test antibody or an antigen-binding fragment thereof that specifically binds human FH wherein the test antibody or antigen-binding fragment is obtained from immunizing an animal with an antigen protein that comprises the amino acid sequence of human FH-related 1 (FHR-1);

(b) assessing competition of the test antibody or the fragment thereof with a reference antibody, or a corresponding fragment thereof, for binding CCP18 of FH in a competition binding assay; and (c) assessing an FH activity in the presence and absence of the test antibody or the fragment thereof, wherein the reference antibody comprises a light chain CDR1, a light chain CDR2, a light chain CDR3, a heavy chain CDR1, a heavy chain CDR2, and a heavy chain CDR3 comprising the amino acid sequences of SEQ ID NOs: 33, 34, 35, 37, 38, and 39; 17, 18, 19, 21, 22, and 23; 49, 50, 51, 53, 54, and 55; 65, 66, 67, 69, 70, and 71; or 1, 2, 3, 5, 6, and 7, respectively.

2. The method of claim 1, wherein the reference antibody comprises:

(i) a light chain variable region comprising an amino acid sequence at least 90% identical to SEQ ID NO: 36 and a heavy chain variable region comprising an amino acid sequence at least 90% identical to SEQ ID NO: 40;

(ii) a light chain variable region comprising an amino acid sequence at least 90% identical to SEQ ID NO: 20 and a heavy chain variable region comprising an amino acid sequence at least 90% identical to SEQ ID NO: 24;

(iii) a light chain variable region comprising an amino acid sequence at least 90% identical to SEQ ID NO: 52 and a heavy chain variable region comprising an amino acid sequence at least 90% identical to SEQ ID NO: 56;

(iv) a light chain variable region comprising an amino acid sequence at least 90% identical to SEQ ID NO: 68 and a heavy chain variable region comprising an amino acid sequence at least 90% identical to SEQ ID NO: 71; or (v) a light chain variable region comprising an amino acid sequence at least 90% identical to SEQ ID NO: 4 and a heavy chain variable region comprising an amino acid sequence at least 90% identical to SEQ ID NO: 8.

3. The method of claim 1, wherein the reference antibody comprises a light chain CDR1, a light chain CDR2, a light chain CDR3, a heavy chain CDR1, a heavy chain CDR2, and a heavy chain CDR3 comprising the amino acid sequences of SEQ ID NOs: 33, 34, 35, 37, 38, and 39; 17, 18, 19, 21, 22, and 23; 49, 50, 51, 53, 54, and 55; or 65, 66, 67, 69, 70, and 71, respectively.

4. The method of claim 3, wherein the reference antibody comprises:

(i) a light chain variable region comprising an amino acid sequence at least 90% identical to SEQ ID NO: 36 and a heavy chain variable region comprising an amino acid sequence at least 90% identical to SEQ ID NO: 40;

(ii) a light chain variable region comprising an amino acid sequence at least 90% identical to SEQ ID NO: 20 and a heavy chain variable region comprising an amino acid sequence at least 90% identical to SEQ ID NO: 24;

(iii) a light chain variable region comprising an amino acid sequence at least 90% identical to SEQ ID NO: 52 and a heavy chain variable region comprising an amino acid sequence at least 90% identical to SEQ ID NO: 56; or (iv) a light chain variable region comprising an amino acid sequence at least 90% identical to SEQ ID NO: 68 and a heavy chain variable region comprising an amino acid sequence at least 90% identical to SEQ ID NO: 71.

5. The method of claim 1, wherein the animal is a rodent.

6. The method of claim 5, wherein the rodent is a mouse.

7. The method of claim 6, wherein the mouse is a BALB/c mouse.

8. The method of claim 1, further comprising producing the test antibody or the fragment thereof, wherein the test antibody or the fragment thereof has greater binding affinity for human FH than FH.07.

9. The method of claim 1, further comprising humanizing the test antibody or the fragment thereof and producing the humanized antibody or an antigen-binding fragment thereof, wherein the humanized antibody or the fragment thereof has greater binding affinity for human FH than FH.07.

10. The method of claim 9, wherein the humanized antibody or fragment thereof comprises human framework regions in the heavy and light chain variable regions.

11. The method of claim 9, wherein the humanized antibody or the fragment thereof binds human FH with a $K_D$ of $2.5\times10^{-8}$ M or less and/or binds a human FH fragment comprised of CCP18-20 with a $K_D$ of $1\times10^{-10}$ M or less.

12. The method of claim 9, wherein the humanized antibody or the fragment thereof binds human FH with a $K_D$ of $6\times10^{-9}$ M or less and/or binds a human FH fragment comprised of CCP18-20 with a $K_D$ of $6\times10^{-12}$ M or less.

13. The method of claim 9, wherein the humanized antibody or the fragment thereof does not compete with a second reference antibody for binding CCP18 of FH in a competition binding assay, wherein the second reference antibody comprises a light chain variable region comprising the amino acid sequence of SEQ ID NO: 84 and a heavy chain variable region comprising the amino acid sequence of SEQ ID NO: 88.

14. The method of claim 9, wherein the humanized antibody or the fragment thereof:

(a) inhibits C3 deposition on LPS in vitro with an $IC_{50}$ value of 38 nM or less;

(b) inhibits hemolytic activity in vitro with an $IC_{50}$ value of 150 nM or less, and/or (c) increases binding affinity of FH for C3b in vitro to a K$_D$ value of at most 2 μM and/or increases binding affinity of FH for C3b in vitro by at least 3 fold.

15. The method of claim 9, wherein producing the humanized antibody or the fragment thereof comprises:

(i) providing a cell with a nucleic acid encoding the humanized antibody or fragment thereof, or a vector comprising the nucleic acid; and (ii) allowing the cell to translate the sequence of the nucleic acid.

16. The method of claim 15, wherein producing the humanized antibody or the fragment thereof further comprises harvesting and purifying the humanized antibody or fragment thereof.

17. The method of claim 14, wherein the humanized antibody or the fragment thereof:

(a) inhibits C3 deposition on LPS in vitro with an C$_{50}$ value of 30 nM or less; and/or (b) inhibits hemolytic activity in vitro with an IC$_{50}$ value of 130 nM or less.

* * * * *